United States Patent
Oomine et al.

(10) Patent No.: US 12,147,515 B2
(45) Date of Patent: Nov. 19, 2024

(54) AUTHENTICATION SYSTEM AND IMAGING APPARATUS

(71) Applicants: NEC Corporation, Tokyo (JP); NEC Platforms, Ltd., Kawasaki (JP)

(72) Inventors: Masahiro Oomine, Kanagawa (JP); Daisuke Shimada, Kanagawa (JP); Daisuke Okamoto, Kanagawa (JP); Katsumi Kayama, Kanagawa (JP); Shuya Gonda, Kanagawa (JP)

(73) Assignees: NEC CORPORATION, Tokyo (JP); NEC Platforms, Ltd., Kanagawa (JP)

( * ) Notice: Subject to any disclaimer, the term of this patent is extended or adjusted under 35 U.S.C. 154(b) by 0 days.

(21) Appl. No.: 17/639,968

(22) PCT Filed: Jul. 30, 2021

(86) PCT No.: PCT/JP2021/028404
§ 371 (c)(1),
(2) Date: Mar. 3, 2022

(87) PCT Pub. No.: WO2023/007714
PCT Pub. Date: Feb. 2, 2023

(65) Prior Publication Data
US 2024/0045936 A1 Feb. 8, 2024

(51) Int. Cl.
*G06F 21/32* (2013.01)
*G06V 40/19* (2022.01)
*G07C 9/37* (2020.01)

(52) U.S. Cl.
CPC .............. *G06F 21/32* (2013.01); *G06V 40/19* (2022.01); *G07C 9/37* (2020.01)

(58) Field of Classification Search
CPC ........ G06F 21/32; G06V 40/19; G06V 40/18; G06V 40/193; G06V 40/197; G06V 40/20; G07C 9/37
See application file for complete search history.

(56) References Cited

U.S. PATENT DOCUMENTS

2002/0130961 A1* 9/2002 Lee .......................... G07C 9/37
348/333.03
2016/0012279 A1 1/2016 Bludau et al.
(Continued)

FOREIGN PATENT DOCUMENTS

JP 2000-220333 A 8/2000
JP 2000-237169 A 9/2000
(Continued)

OTHER PUBLICATIONS

International Search Report for PCT Application No. PCT/JP2021/028404, mailed on Oct. 12, 2021.

*Primary Examiner* — Quazi Farooqui
(74) *Attorney, Agent, or Firm* — Sughrue Mion, PLLC

(57) ABSTRACT

An authentication system SYS comprises: an imaging unit 12 capable of generating an iris image IMG_I by capturing an image of an iris of an target P; and a display unit 15 capable of displaying information related to authentication of the target using the iris image, wherein at least a part of the imaging unit is disposed in a space SP2 adjacent to a back surface 152 of the display unit, the back surface being located opposite a display surface 151 for displaying the information, and the imaging unit is oriented in a direction different from a direction in which the target is present.

15 Claims, 42 Drawing Sheets

(56) References Cited

U.S. PATENT DOCUMENTS

| | | |
|---|---|---|
| 2019/0188470 A1 | 6/2019 | Su et al. |
| 2020/0065461 A1* | 2/2020 | Mori .......................... G06F 3/01 |
| 2022/0141372 A1 | 5/2022 | Chono et al. |
| 2022/0270380 A1* | 8/2022 | Nakamura ............. G06V 40/19 |

FOREIGN PATENT DOCUMENTS

| | | |
|---|---|---|
| JP | 2017-062756 A | 3/2017 |
| JP | 2019-219698 A | 12/2019 |
| JP | 2020-194599 A | 12/2020 |
| WO | 2018/038158 A1 | 3/2018 |
| WO | 2020/170914 A1 | 8/2020 |
| WO | 2021/059526 A1 | 4/2021 |

* cited by examiner

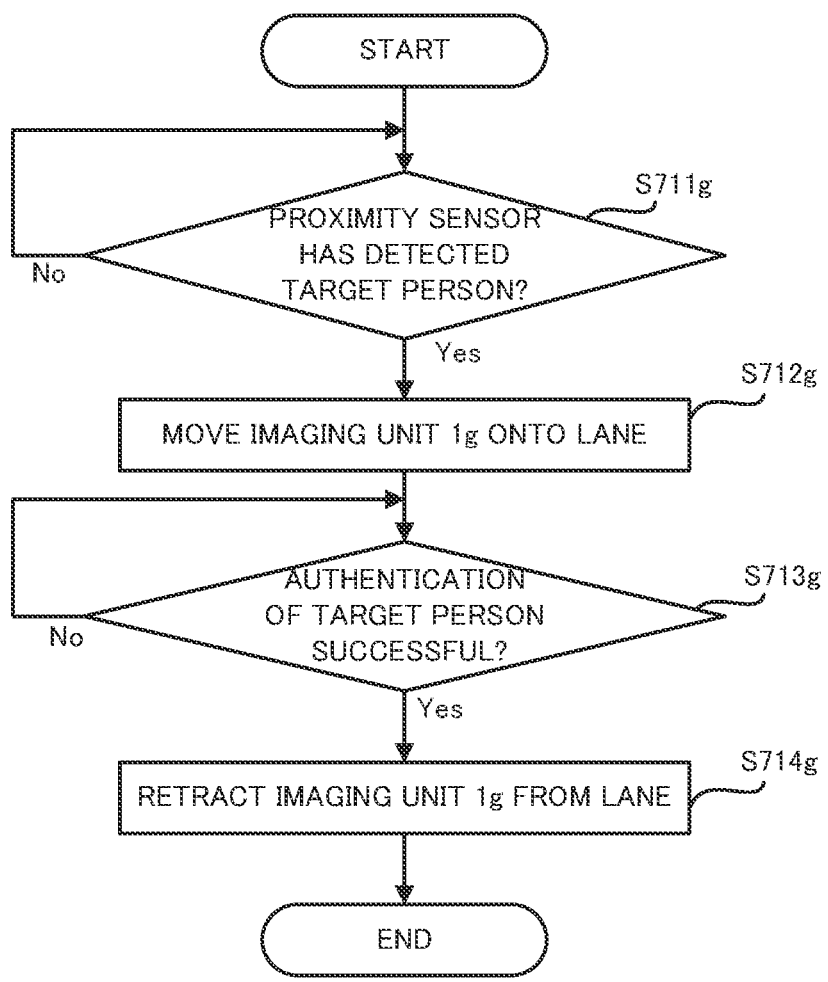

AUTHENTICATION SYSTEM AND IMAGING APPARATUS

This application is a National Stage Entry of PCT/JP2021/028404 filed on Jul. 30, 2021, the contents of all of which are incorporated herein by reference, in their entirety.

TECHNICAL FIELD

This disclosure relates to, for example, a technical field of an authentication system capable of authenticating a target using an iris image generated by capturing an image of a target's iris, and a technical field of an imaging apparatus available in an authentication system.

BACKGROUND ART

An example of an authentication system capable of authenticating a target using an iris image generated by capturing an image of the iris of the target is described in Patent Document 1. In addition, as prior art documents related to this disclosure, there are from Patent Document 2 to Patent Document 6.

CITATION LIST

Patent Document

Patent Document 1: WO 2018/038158 A1
Patent Document 2: JP 2000-237169 A
Patent Document 3: JP 2000-220333 A
Patent Document 4: WO 2021/059526 A1
Patent Document 5: WO 2020/170914 A1
Patent Document 6: JP 2020-194599 A

SUMMARY

Technical Problem

The present disclosure aims to provide an authentication system and an imaging apparatus for improving the techniques described in the prior art documents.

Solution to Problem

One aspect of the authentication system comprises: an imaging unit that is capable of generating an iris image by capturing an image of an iris of an target; and a display unit that is capable of displaying information related to authentication of the target using the iris image, wherein at least a part of the imaging unit is disposed in a space adjacent to a back surface of the display unit, the back surface being located opposite a display surface for displaying the information, and the imaging unit is oriented in a direction different from a direction in which the target is present.

One aspect of the imaging apparatus comprises: an imaging unit that is capable of generating an iris image by capturing an image of an iris of an target; and a display unit that is capable of displaying information related to authentication of the target using the iris image, wherein at least a part of the imaging unit is disposed in a space adjacent to a back surface of the display unit, the back surface being located opposite a display surface for displaying the information, and the imaging unit is oriented in a direction different from a direction in which the target is present.

BRIEF DESCRIPTION OF DRAWINGS

FIG. 46 is a flowchart showing a flow of operation to move the imaging unit.

DESCRIPTION OF EXAMPLE EMBODIMENTS

Hereinafter, example embodiments of the authentication system will be described with reference to the drawings.

(1) First Example Embodiment

Figure 1:
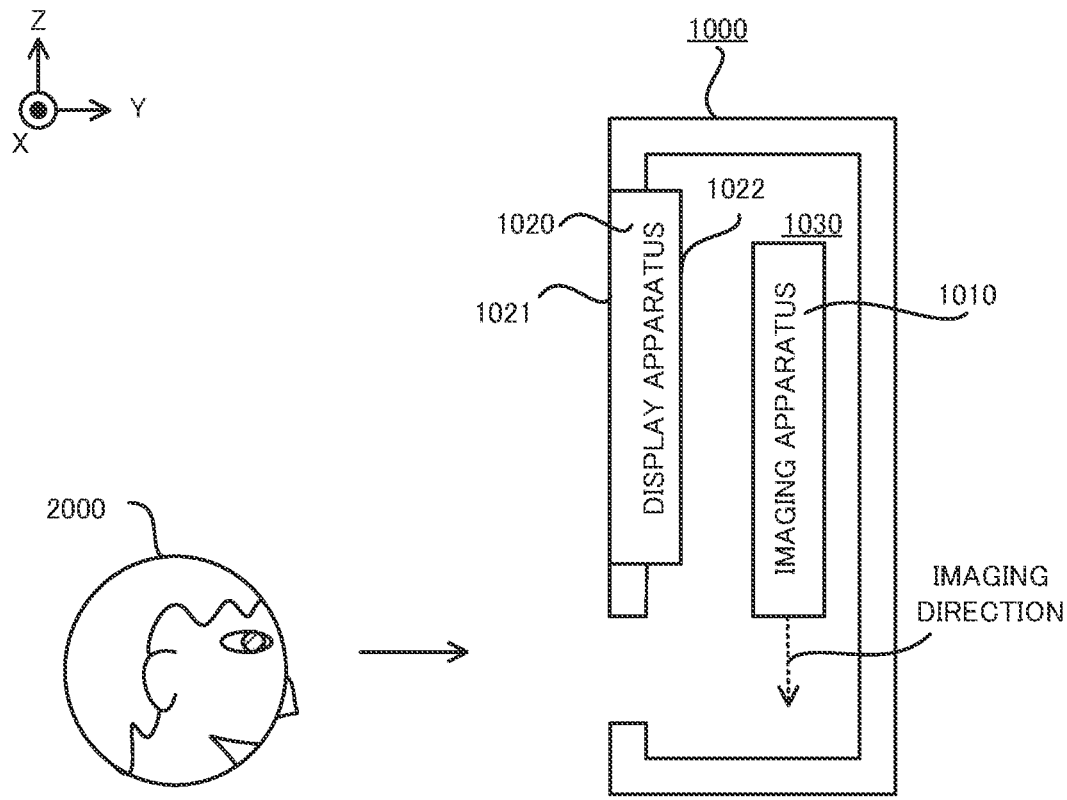
FIG. 1 is a cross-sectional view showing a configuration of an authentication system in the first example embodiment.

First, a description will be given of a first example embodiment of an authentication system and an imaging apparatus. Referring now to FIG. 1, a description will be given of an authentication system 1000 in which the first example embodiment of the authentication system and the imaging apparatus is applied. FIG. 1 is a cross-sectional view showing the configuration of the authentication system 1000 in the first example embodiment. In FIG. 1, using a three-dimensional coordinate system composed of the X-axis, the Y-axis and the Z-axis orthogonal to each other, the positional relationship of components constituting the authentication system 1000 will be described. Each of the X-axis and Y-axis is an axis along the horizontal plane (i.e., an axis extending in the horizontal direction), the Z-axis is an axis perpendicular to the horizontal plane (i.e., an axis extending in the vertical direction).

As shown in FIG. 1, the authentication system 1000 includes an imaging apparatus 1010 which is a specific example of the "imaging unit" in the supplementary notes to be described later, and a display apparatus 1020 which is a specific example of the "display unit" in the supplementary notes to be described later. The imaging apparatus 1010 is capable of generating iris images by capturing an image of the iris of the target 2000. The displaying apparatus 1020 is capable of displaying information (e.g., information about authentication results) related to the authentication of the target 2000 using iris images. In the first example embodiment, the authentication system 1000 may or may not include an authentication apparatus for authenticating the target 2000 using iris images. If the authentication system 1000 is not provided with the authentication apparatus, the authentication system 1000 may be referred to as an imaging system or imaging apparatus, or display system or display apparatus.

At least a part of the imaging apparatus 1010 is disposed in a space 1030 adjacent to the display apparatus 1020. Specifically, the display apparatus 1020 includes a display surface 1021 for displaying information about the authentication of the target 2000 using an iris image. At least a part of the imaging apparatus 1010 is disposed in a space 1030 adjacent to the back surface 1022 of the display apparatus 1020 located opposite the display surface 1021.

In the space 1030, the imaging apparatus 1010 is oriented in a direction different from a direction in which the target 2000 is present. In the example shown in FIG. 1, the target 2000 is positioned in a lateral direction (e.g., the Y-axis direction, as an example, horizontally) as viewed from the imaging apparatus 1010. That is, the target 2000 is located at a position along the lateral direction at a distance as viewed from the imaging apparatus 1010. In this case, the imaging apparatus 1010 faces in a direction different from the lateral direction. For example, the imaging apparatus 1010 may face in a direction intersecting the lateral direction (e.g., a longitudinal direction). As one example, the imaging apparatus 1010 may face in a direction orthogonal to the lateral direction (e.g., in the Z-axis direction and in the vertical direction).

The "direction in which the imaging apparatus 1010 faces" may mean, for example, a direction in which the imaging apparatus 1010 captures an image. The "direction in which the imaging apparatus 1010 faces" may mean, for example, a direction in which the imaging range of the imaging apparatus 1010 is extended when viewed from the imaging apparatus 1010. The "direction in which the imaging apparatus 1010 faces" may mean, for example, a direction in which the optical system of the imaging apparatus 1010 (e.g., the optical system including a lens or the like) is oriented. The "direction in which the imaging apparatus 1010 faces" may mean, for example, a direction in which the optical axis of the optical system of the imaging apparatus 1010 extends.

The authentication system 1000 of such a first example embodiment can perform the effect that the size of the authentication system 1000 can be reduced. In other words, the authentication system 1000 according to the first example embodiment can appropriately solve the technical problem that the size of the authentication system becomes too large.

(2) Second Example Embodiment

Subsequently, a description will be given of a second example embodiment of the authentication system and the imaging apparatus. Hereinafter, referring to FIG. 2, the authentication system SYS second example embodiment with respect to the authentication system and the imaging apparatus is applied will be described. In the following description, using a three-dimensional coordinate system composed of the X-axis, the Y-axis and the Z-axis orthogonal to each other, the positional relationship of components constituting the authentication system SYS will be described. Each of the X-axis and Y-axis is an axis along the horizontal plane (i.e., an axis extending in the horizontal direction), the Z-axis is an axis perpendicular to the horizontal plane (i.e., an axis extending in the vertical direction).

(2-1) Overall Configuration of Authentication System SYS

Figure 2:
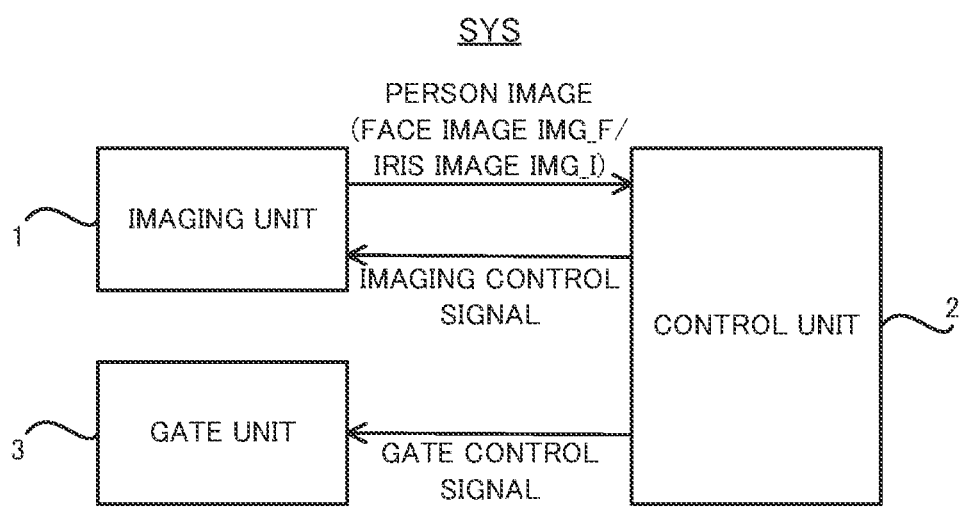
FIG. 2 is a block diagram showing a configuration of an authentication system in the second example embodiment.

First, an overall configuration of the authentication system SYS according to the second example embodiment will be described with reference to FIG. 2. FIG. 2 is a block diagram showing the overall configuration of the authentication system SYS in the second example embodiment.

As shown in FIG. 2, the authentication system SYS includes an imaging unit 1, a control unit 2, and a gate unit 3. The imaging unit 1, the control unit 2 and the gate unit 3 may be referred to as an imaging apparatus, a control apparatus and a gate apparatus respectively.

Figure 3A:
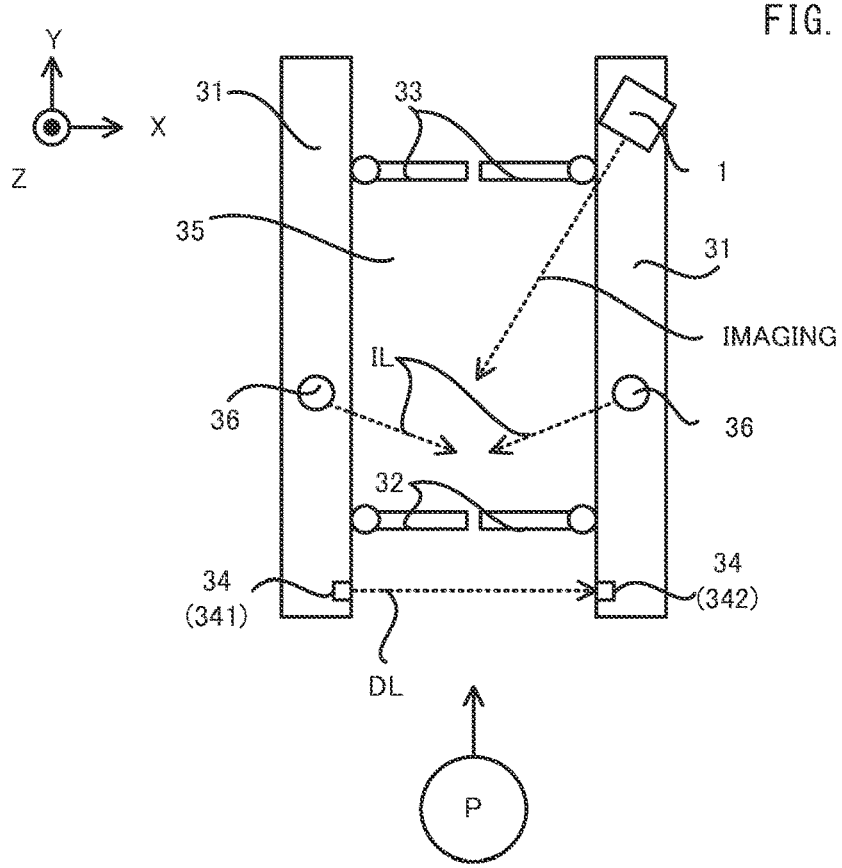
FIG. 3A is a top view showing an example of a configuration of a gate unit in the second example embodiment.

The imaging unit 1 is capable of imaging at least a part of a target (see FIG. 3A). The target may include, for example, a person. The target may include animals that are different from humans (e.g., mammals such as dogs and cats, birds such as sparrows, reptiles such as snakes, amphibians such as frogs, and fish such as goldfish). The target may include an inanimate object. The inanimate object may include a robot that takes after a person or an animal. In the following description, an example will be described in which the target is a person (hereinafter, referred to as "the target person P").

The imaging unit 1 is, by capturing an image of at least a part of the target person P, capable of generating a person image IMG in which at least a part of the target person P is captured. Specifically, as will be described in detail later, the imaging unit 1 is capable of generating an iris image IMG_I in which the iris of the target person P is captured as the person image IMG by capturing the image of the iris of the target person P. Further, the imaging unit 1 may be capable of generating a face image IMG_F in which the face of the target person P is captured as the person image IMG by capturing the image of the face of the target person P.

A portion of the target person P, which is different from the iris, may be captured in the iris image IMG_I. Even in this case, the target person P is authenticated using the iris of the target person P included in the iris image IMG_I as will be described in detail later. Therefore, even if the portion of the target person P different from the iris is included in the iris image IMG_I, problems will not occur. Alternatively, when the portion of the target person P that is different from the iris is captured in the iris image IMG_I but the iris of the target person P is not captured, as will be described in detail later, the imaging unit 1 may generate the iris image IMG_I in which the iris of the target person P is captured by rotating a rotation mirror 13 and/or adjusting the position of an iris camera 12. Similarly, the portion of the target person P that is different from the face may be captured in the face image IMG_F. Even in this case, as will be described in detail later, the position of the eyes of the target person P is specified using the face of the target person P captured in the face image IMG_F. Therefore, even if the portion of the target person P that is different from the face is captured in the face image IMG_F, problems will not occur. Alternatively, when the portion of the target person P that is different from the face is captured in the face image IMG_F but the face of the target person P is not captured, as will be described in detail later, the imaging unit 1 may generate the face image IMG_F in which the face of the target person P is captured by adjusting the position of the face camera 11.

The control unit 2 acquires the person image IMG from the imaging unit 1 and performs an authentication operation for authenticating the target person P using the person image IMG. In the second example embodiment, the control unit 2 acquires the iris image IMG_I from the imaging unit 1 and performs an authentication operation for authenticating the target person P using the iris image IMG_I. In other words, the control unit 2 performs the authentication operation related to the iris authentication. Specifically, based on the pattern of the iris of the target person P captured in the acquired iris image IMG_I, the control unit 2 determines whether or not the target person P captured in the acquired iris image IMG_I is the same as the person registered in advance (hereinafter, referred to as "the registered person"). When it is determined that the target person P captured in the iris image IMG_I is the same as the registered person, it is determined that the authentication of the target person P has succeeded. On the other hand, when it is determined that the target person P captured in the iris image IMG_I is not the same as the registered person, it is determined that the authentication of the target person P has failed.

The control unit 2, as at least a part of the authentication operation, may perform an operation to control the imaging unit 1 so as to capture the image of at least a part of the target person P. For example, the control unit 2 may control the imaging unit 1 by outputting to the imaging unit 1 an imaging control signal for controlling the imaging unit 1 so as to capture the image of at least a part of the target person P.

Figure 3B:
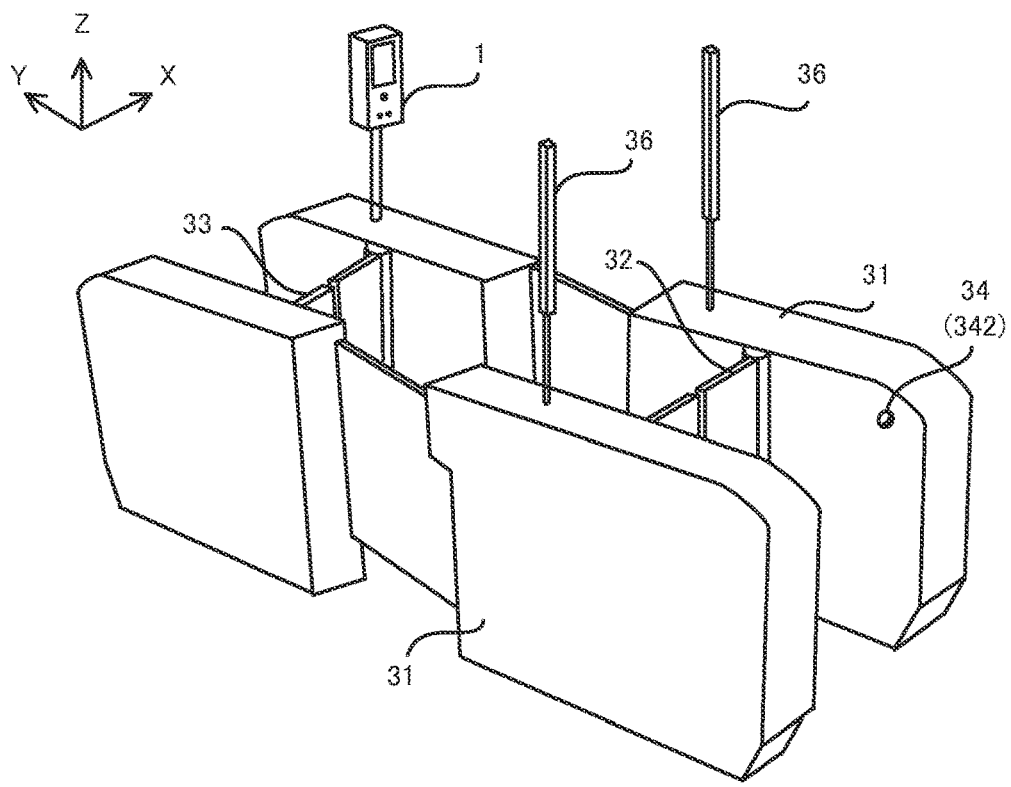
FIG. 3B is a perspective view showing an example of the configuration of the gate unit in the second example embodiment.

The gate unit 3 is an apparatus capable of controlling pass of the target person P. An example of the configuration of the gate unit 3 is shown in FIG. 3A and FIG. 3B. FIG. 3A is a top view showing an example of the configuration of the gate unit 3, and FIG. 3B is a perspective view showing an example of the configuration of the gate unit 3. As shown in FIG. 3A and FIG. 3B, the gate unit 3 includes a pair of guide walls 31, a first flapper gate 32, a second flapper gate 33, a proximity sensor 34, and at least one illumination apparatus 36. However, the configuration of the gate unit 3 is not limited to the configuration shown in FIG. 3A and FIG. 3B. Alternatively, originally, the authentication system SYS may not include a gate unit 3.

A pair of guide walls 31 forms, between the pair of guide walls 31, a lane 35 which allows the target person P to go therethrough. Therefore, the pair of guide walls 31 each extend along a direction in which the lane 35 extends (in the example shown in FIG. 3A and FIG. 3B, the Y-axis direction).

The first flapper gate 32 is a plate-shaped member capable of controlling pass of the target person P. In addition to or in place of the first flapper gate 32, a gate bar may be used, the gate bar being a rod-shaped member capable of controlling the pass of the target person P. The state of the first flapper gate 32 is controlled by the control unit 2 based on the detection result of the target person P by the proximity sensor 34. Specifically, when the proximity sensor 34 has detected the target person P, the state of the first flapper gate 32 is controlled by the control unit 2 so as to become an open state that allows the target person P to pass through the first flapper gate 32. On the other hand, when the proximity sensor 34 does not detect the target person P, the state of the first flapper gate 32 is controlled by the control unit 2 so as to become a closed state that makes the target person P impossible to pass through the first flapper gate 32. However, the state of the first flapper gate 32 may be controlled based on the detection result of the target person P by the proximity sensor 34, independently from the control by the control unit 2.

The second flapper gate 33 is a plate-shaped member capable of controlling pass of the target person P. In addition to or in place of the second flapper gate 33, a gate bar may be used, the gate bar being a rod-shaped member capable of controlling the pass of the target person P. The state of the second flapper gate 33 is controlled by the control unit 2 based on the authentication result of the target person P by the control unit 2. Specifically, when the authentication of the target person P by the control unit 2 is successful (that is, it is determined that the target person P matches the registered person), the state of the second flapper gate 33 is controlled by the control unit 2 so as to become an open state that allows the target person P to pass through the second flapper gate 33. On the other hand, when the authentication of the target person P by the control unit 2 fails (that is, it is determined that the target person P does not match the registered person), the state of the second flapper gate 33 is controlled by the control unit 2 so as to become a closed state that makes the target person impossible to pass through the second flapper gate 33. However, the state of the first flapper gate 32 may be controlled based on the authentication result of the target person P by the control unit 2, independently from the control by the control unit 2.

The proximity sensor 34 is a detection apparatus capable of detecting the target person P. The proximity sensor 34 may be capable of detecting the target person P approaching the gate unit 3. The proximity sensor 34 may be capable of detecting the target person P entering the lane 35 which the gate unit 3 forms. The proximity sensor 34 may be capable of detecting the target person P who is going to enter the lane 35 which the gate unit 3 forms.

In the example shown in FIG. 3A and FIG. 3B, the proximity sensor 34 is capable of optically detecting the target person P. Specifically, the proximity sensor 34 includes a light emitting device 341 and a light receiving device 342 disposed respectively on the pair of guide walls 31. The light emitting device 341 is capable of emitting a detecting light DL propagating across the lane 35. The light receiving device 342 is capable of receiving the detection light DL emitted by the light emitting device 341. When the target person P does not enter the lanes 35, the detection light DL emitted by the light emitting device 341 is not blocked by the target person P, and therefore the light receiving device 342 receives the detection light DL emitted by the light emitting device 341. On the other hand, when the target person P enters the lane 35 (particularly, enters the optical path of the detection light DL), the detection light DL emitted by the light emitting device 341 is blocked by the target person P, and therefore the light receiving device 342 does not receive the detection light DL emitted by the light emitting device 341. Therefore, the light reception result by the light receiving device 342 indicates the detection result of the target person P.

The imaging unit 1 described above captures the image of the target person P located in the lane 35 which the gate unit 3 forms. Therefore, the imaging unit 1 may be disposed in the gate unit 3. For example, as shown in FIG. 3A and FIG. 3B, the imaging unit 1 may be disposed on the guide wall 31. However, the disposed position of the imaging unit 1 is not limited to the position shown in FIG. 3A and FIG. 3B. The imaging unit 1 may not be disposed in the gate unit 3. The imaging unit 1 may not be disposed on a different member from the gate unit 3. For example, the imaging unit 1 may be mounted to a support member (e.g., a wall member, a pole member or the like) disposed in the vicinity of the gate unit 3.

The illumination apparatus 36 may, for example, be disposed on the guide wall 31. The illumination apparatus 36, when the imaging unit 1 (in particular, the iris camera 12 to be described later) captures the image of the target person P located in the lane 35, illuminates the target person P (in particular, his/her eyes) with illumination light IL. As will be described in detail below, the iris camera 12 captures the image of the iris of the target person P located between the first flapper gate 32 and the second flapper gate 33. Therefore, the illumination apparatus 36 may be disposed in a position capable of illuminating with the illumination light IL the iris of the target person P located between the first flapper gate 32 and the second flapper gate 33. Although FIG. 3B shows an example in which the illumination apparatus 36 has a vertically long shape, the shape of the illumination apparatus 36 is not limited to the shape shown in FIG. 3B.

The imaging unit 1 may image the target person P that is moving along the lane 35 (e.g., the target person P that moves without being stationary in front of the imaging unit 1). Alternatively, the imaging unit 1 may image the target person P that is stationary in the lane 35 (e.g., the target person P that is stationary in front of the imaging unit 1).

Again in FIG. 2, the control unit 2, as at least a part of the authentication operation, may perform an operation of controlling the gate unit 3 based on the authentication result. For example, the control unit 2 may control the gate unit 3 by outputting to the gate unit 3 a gate control signal for switching the state of the first flapper gate 32 between the open state and the closed state. For example, the control unit 2 may control the gate unit 3 by outputting to the gate unit 3 a gate control signal for switching the state of the second flapper gate 33 between the open state and the closed state.

(2-2) Configuration of the Imaging Unit 1

Figure 4:
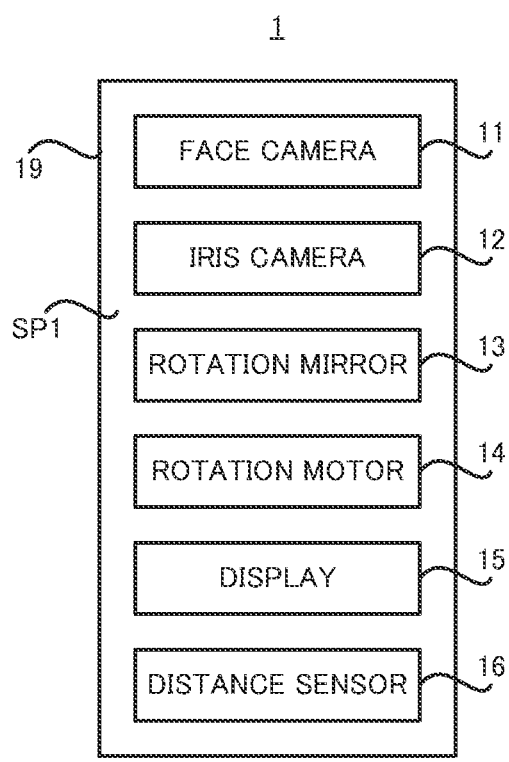
FIG. 4 is a block diagram showing a configuration of an imaging unit in the second example embodiment.
Figure 5:
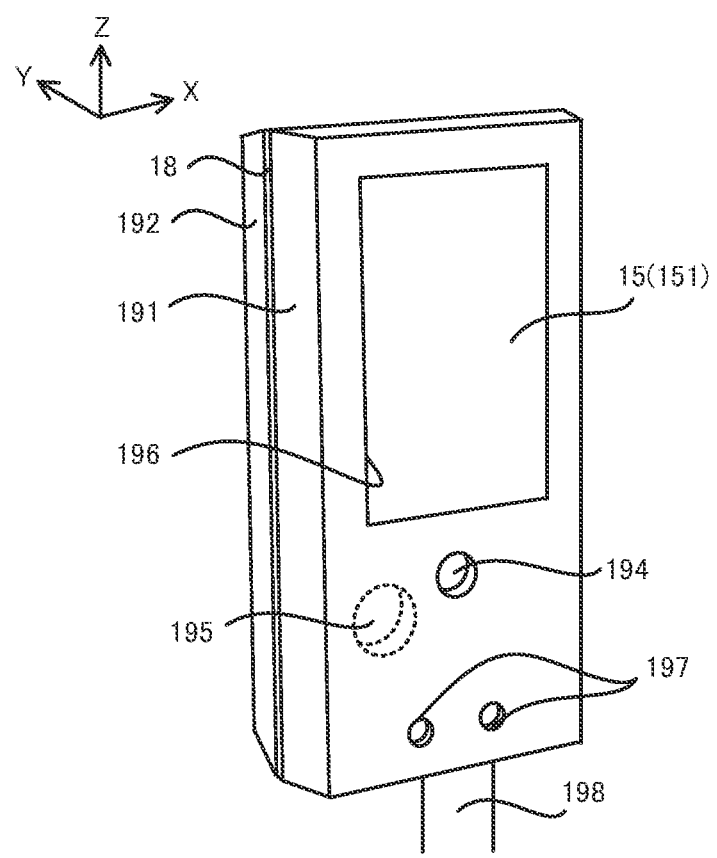
FIG. 5 is a perspective view showing an appearance of the imaging unit in the second example embodiment.

Subsequently, with reference to FIGS. 4 to 5, a description will be given of the configuration of the imaging unit 1. FIG. 4 is a block diagram showing the configuration of the imaging unit 1. FIG. 5 is a perspective view showing an appearance of the imaging unit 1.

As shown in FIGS. 4 and 5, the imaging unit 1 includes a face camera 11, an iris camera 12 which is a specific example of the "imaging unit" in the supplementary notes to be described later, a rotation mirror 13 which is a specific example of each of the "reflective unit" and the "first reflective unit" in the supplementary notes to be described later, a rotation motor 14 which is a specific example of the "rotation driving unit" in the supplementary notes to be described later, a display 15 which is a specific example of the "display unit" in the supplementary notes to be described later, and a distance sensor 16.

The face camera 11 is an imaging apparatus capable of imaging the face of the target person P. The face camera 11 is typically capable of imaging at least a part of the target person P including the face of the target person P. The face camera 11 is capable of generating the face image IMG_F in which the face of the target person P is captured by capturing the image of the face of the target person P.

The iris camera 12 is an imaging apparatus capable of at least imaging the iris of the target person P. The iris camera 12 is typically capable of imaging at least a part of the target person P including the iris of the target person P. The iris camera 12 is capable of generating the iris image IMG_I in which the iris of the target person P is captured by capturing the image of the iris of the target person P.

The rotation mirror 13 is an optical element that reflects light from the target person P toward the iris camera 12. For this reason, the iris camera 12 captures the image of the iris of the target person P through the rotation mirror 13. Specifically, as described above, when the iris camera 12 captures the image of the iris of the target person P, the iris of the target person P is illuminated by the illumination light IL from the illumination apparatus 36. The illumination light IL may include, for example, near-infrared light (i.e., light having a wavelength included in the wavelength band of near-infrared light). From the iris illuminated by the illumination light, reflected light of the illumination light (or scattered light in addition to or in place of the reflected light) is emitted. Thus, the light from the target person P reflected on the rotation mirror 13 toward the iris camera 12 may include at least one of the reflected light and the scattered light with respect to the illumination light emitted from the iris. The iris camera 12 receives the light from the target person P using an image pickup device 122 (see FIG. 7 to be described later), such as a CCD (Charge Coupled Device) or a CMOS (Complementary Metal Oxide Semiconductor), to capture the image of the iris of the target person P. The technical reason why the iris camera 12 captures the image of the iris of the target person P through the rotation mirror 13 will be described later with the description about the arrangement of the iris camera 12.

The rotation motor 14 is a drive apparatus for rotating under the control of the control unit 2, the rotation mirror 13 around a predetermined rotational axis. The technical reason for the rotatory motor 14 to rotate the rotation mirror 13 will be described later with the description about the arrangement of the iris camera 12.

The display 15 is a display apparatus capable of displaying desired information. For example, the display 15 may be capable of displaying information about the authentication of the target person P where the iris image IMG_I is used. The information about the authentication of the target person P may include information about the authentication result of the target person P. The information about the authentication of the target person P may include information to be notified to the target person P who has succeeded in authentication (e.g., information for notice of allowing the pass of the second flapper gate 33). The information about the authentication of the target person P may include information to be notified to the target person P that has failed in authentication (e.g., information for notice of the next operation which the target person P should perform because the authentication has failed).

The imaging unit 1 may include any output apparatus capable of outputting desired information in addition to or in place of the display 15. For example, the imaging unit 1 may include an audio output apparatus (e.g., a speaker) capable of outputting desired information as audio. For example, the imaging unit 1 may include a paper output apparatus (e.g., a printer) capable of outputting a paper on which desired information is described.

The distance sensor 16 is a measurement apparatus capable of measuring a distance from the imaging unit 1 to the target person P. The distance sensor 16 may be capable of optically measuring the distance from the imaging unit 1 to the target person P. A TOF (Time Of Flight) type sensor, a triangulation type sensor, a LiDAR (Light Detection and Ranging) and/or a stereo camera can be one example of the distance sensor 16 capable of optically measuring a distance. However, the imaging unit 1 may not include the distance sensor 16.

The face camera 11, the iris camera 12, the rotation mirror 13, the rotation motor 14, the display 15 and the distance sensor 16 are disposed in a housing 19. That is, the face camera 11, the iris camera 12, the rotation mirror 13, the rotation motor 14, the display 15 and the distance sensor 16 are arranged in the housing space SP1 in the housing 19 (see FIGS. 6 and 7 to be described later). The housing 19 comprises, as shown in FIG. 5, a front housing 191 and a rear housing 192. By combining the front housing 191 and the rear housing 192, the housing space SP1 is formed between the front housing 191 and the rear housing 192. The face camera 11, the iris camera 12, the rotation mirror 13, the rotation motor 14, the display 15 and the distance sensor 16 are disposed in the housing space SP1.

Figure 6:
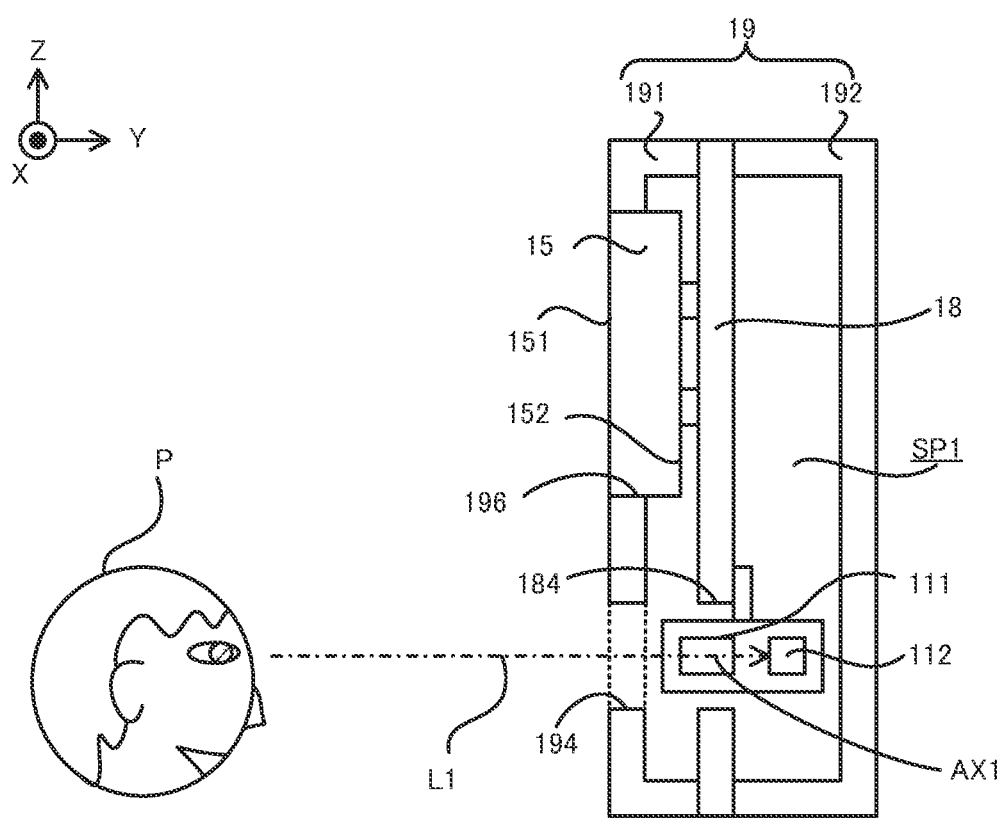
FIG. 6 is a cross-sectional view showing a cross-section of the imaging unit in the second example embodiment (in particular, a cross-section including a face camera, a display and a housing).
Figure 7:
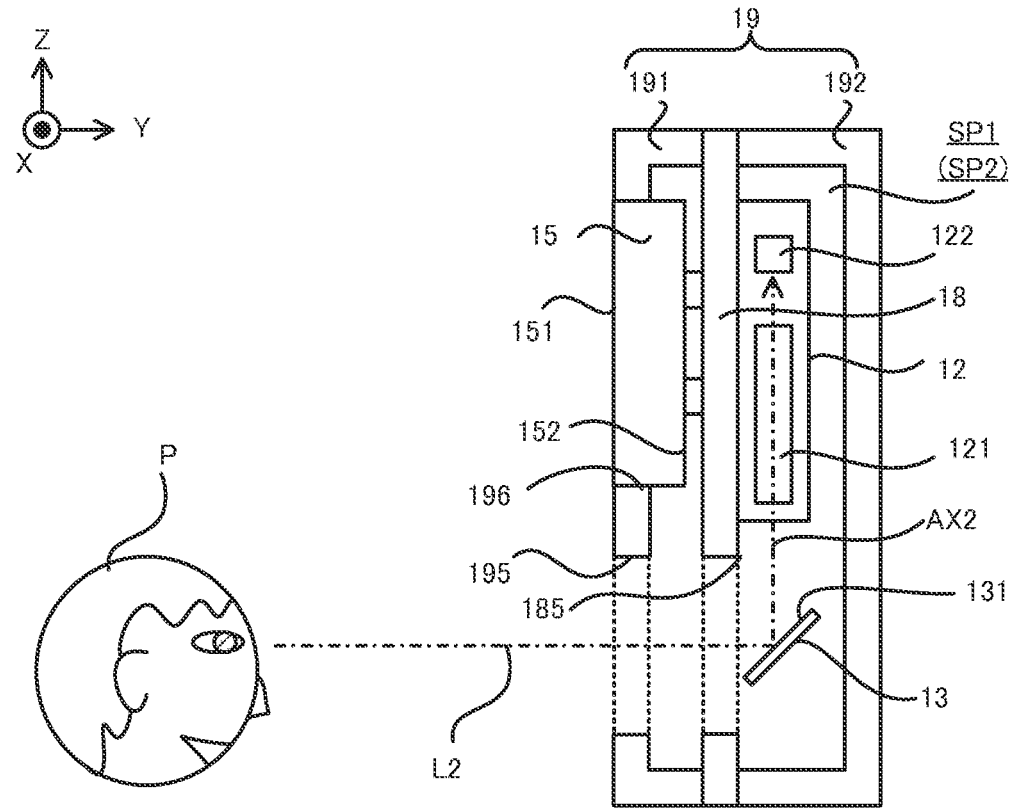
FIG. 7 is a cross-sectional view showing a cross-section of the imaging unit in the second example embodiment (in particular, the cross-section including an iris camera, a mirror, the display, and the housing).

Referring now to FIGS. 6 and 7, a method of placing the face camera 11, the iris camera 12, the rotation mirror 13, and the display 15 in the housing 19 will be described. FIG. 6 is a cross-sectional view showing a cross-section of the imaging unit 1 (in particular, the cross-section including the face camera 11, the display 15 and the housing 19). FIG. 7 is a cross-sectional view showing a cross-section of the imaging unit 1 (in particular, the cross-section including the iris camera 12, the rotation mirror 13, the display 15 and the housing 19).

As shown in FIGS. 6 and 7, within the housing 19, the face camera 11, the iris camera 12, and the display 15 may be supported by a support plate 18. That is, the face camera 11, the iris camera 12, and the display 15 may be housed in the housing 19 in a state that the face camera 11, the iris camera 12, and the display 15 are mounted to the support plate 18. In the example shown in FIGS. 6 and 7, though the support plate 18 is a plate-shaped member along the XZ plane, the shape is not limited to the shape shown in FIGS. 6 and 7. However, at least one of the face camera 11, the iris camera 12, and the display 15 may not be supported by the support plate 18. In addition to or in place of at least one of the face camera 11, the iris camera 12, and the display 15, at least one of the rotation mirror 13, the rotation motor 14, and the distance sensor 16 may be supported by the support plate 18.

At least a part of the support plate 18 may be exposed to the outside of the housing 19. For example, in the example shown in FIGS. 6 and 7 (further, in FIG. 5), the support plate 18 is housed in the housing 19 so as to be sandwiched by the front housing 191 and rear housing 192. In this case, as shown in FIGS. 6 and 7 (further, in FIG. 5), at least a part of the outer edge of the support plate 18 may be exposed to the outside of the housing 19. As a result of that, the heat generated by the face camera 11, the iris camera 12, and the display 15 can be released to the outside of the housing 19 through the support plate 18. Thus, the effect of heat on the operation of the face camera 11, the iris camera 12, and the display 15 is reduced. When the heat generated by the face camera 11, the iris camera 12, and the display 15 is released to the outside of the housing 19 through the support plate 18, the support plate 18 may be a member (e.g., a metal member) capable of promoting heat release. However, the support plate 18 may not be exposed to the outside of the housing 19.

A different member from the support plate 18 may be used as a member for discharging heat generated in the housing 19 to the outside of the housing 19. For example, as shown in FIG. 5, when the imaging unit 1 is mounted to the gate unit 3 via a connecting member 198, the connecting member 198 may be used as the member for discharging heat generated in the housing 19 to the outside of the housing 19. Further, in order to further promote heat release, the imaging unit 1 may be provided with a heat releasing fan. The heat releasing fan may be driven to release heat generated in the housing 19 to the outside of the housing 19. For example, the heat releasing fan may be driven so as to discharge the heat generated in the housing 19 to the outside of the housing 19 through an opening formed in the housing 19 (e.g., at least one of the openings 194, 195 and 197 to be described later).

As shown in FIG. 6, the face camera 11 may be arranged so as to face a direction in which the target person P is present. Here, the "direction in which the face camera 11 faces" may mean, for example, a direction in which the face camera 11 takes an image. In this case, in the housing 19, the face camera 11 may be arranged so as to capture the image of a space present in the direction in which the target person P is present. The "direction in which the face camera 11 faces" may mean, for example, a direction in which the imaging range of the face camera 11 extends when viewed from the face camera 11. In this case, in the housing 19, the face camera 11 may be arranged so that the imaging range extends in the direction in which the target person P is present. The "direction in which the face camera 11 faces" may mean, for example, a direction in which an optical system 111 of the face camera 11 (for example, the optical system including a lens or the like) is oriented. In this case, in the housing 19, the face camera 11 may be disposed so that the optical system 111 faces the direction in which the target person P is present. The "direction in which the face camera 11 faces" may mean, for example, a direction in which the optical axis AX1 of the optical system 111 of the face camera 11 extends. In this case, in the housing 19, the face camera 11 may be disposed so that the optical axis AX1 extends in the direction in which the target person P is present.

In the example shown in FIG. 6, the target person P is positioned laterally when viewed from the face camera 11 (for example, in the Y-axis direction and horizontally as an example). That is, the target person P is positioned at a distance along the lateral direction as viewed from the face camera 11. In this case, the face camera 11 may be arranged to face laterally. For example, the face camera 11 may be arranged such that the imaging range of the face camera 11 as viewed from the face camera 11 extends in the lateral direction of the face camera 11. For example, the face camera 11 may be arranged such that the optical axis AX1 of the optical system 111 of the face camera 11 extends along the lateral direction (e.g., the direction along the XY plane, and as an example, the horizontal direction).

The face camera 11 captures the image of the target person P by receiving, using the image pickup device 112, the light from the target person P (e.g., the light from the face of the target person P) L1 via the optical system 111. The light L1 enters the face camera 11 (particularly, the optical system 111) through the opening 194 (see FIGS. 5 and 6) formed in the housing 19 (particularly, the front housing 191). Furthermore, when the face camera 11 is supported by the support plate 18, the light L1 may enter the face camera 11 (in particular, the optical system 111) through the opening 184 formed in the support plate 18. Alternatively, the face camera 11 may be disposed such that at least a part of the face camera 11 is disposed within the opening 184 formed in the support plate 18. As a result of that, the face camera 11 housed in the housing 19 is capable of generating the face image IMG_F by capturing the image of the target person P located outside the housing 19.

On the other hand, as shown in FIG. 7, the iris camera 12 may be arranged so as to face a direction different from the direction in which the target person P is present. Here, the "direction in which the iris camera 12 faces" may mean, for example, a direction in which the iris camera takes an image. In this case, in the housing 19, the iris camera 12 may be disposed so as to capture the image of a space that is present in a direction different from the direction in which the target person P is present. The "direction in which the iris camera 12 faces" may mean, for example, a direction in which the imaging range of the iris camera 12 extends when viewed from the iris camera 12. In this case, in the housing 19, the iris camera 12 may be arranged so that the imaging range extends in a direction different from the direction in which the target person P is present. The "direction in which the iris camera 12 faces" may mean, for example, a direction in which the optical system 121 (for example, the optical system including a lens or the like) of the iris camera 12 is oriented. In this case, in the housing 19, the iris camera 12 may be disposed so that the optical system 121 faces a direction different from the direction in which the target person P is present. The "direction in which the iris camera 12 faces" may mean, for example, a direction in which the optical axis AX2 of the optical system 121 of the iris camera 12 extends. In this case, in the housing 19, the iris camera 12 may be disposed so that the optical axis AX2 extends in a direction different from the direction in which the target person P is present.

In the example shown in FIG. 7, the target person P is positioned in the lateral direction (for example, in the Y-axis direction and horizontally as an example) when viewed from the iris camera 12. That is, the target person P is positioned at a distance along the lateral direction as viewed from the iris camera 12. In this case, the iris camera 12 may be arranged to face in a direction different from the lateral direction. As an example, the iris camera 12 may be arranged to face the longitudinal direction different from the lateral direction (e.g., in the Z-axis direction and as an example in the vertical direction). For example, the iris camera 12 may be positioned such that the imaging range of the iris camera 12 extends in the longitudinal direction of the iris camera 12 when viewed from the iris camera 12. For example, the iris camera 12 may be arranged such that the optical axis AX2 of the optical system 121 of the iris camera 12 extends along the longitudinal direction. As an example, the iris camera 12 may be arranged such that the optical axis AX2 extends along a direction intersecting the XY plane (as an example, the vertical direction or the Z-axis direction).

The iris camera 12 receives using the image pickup device 122, the light (e.g., the light from the iris of the target person P) L2 from the target person P via the optical system 121 to capture the image of the target person P. However, the light L2 from the target person P is difficult to directly enter the optical system 121 of the iris camera 12 which faces in a direction different from the direction in which the target person P is present. Therefore, in the second example embodiment, the iris camera 12 receives the light L2 via the rotation mirror 13. In other words, the light L2 enters the optical system 121 of the iris camera 12 via the rotation mirror 13. Specifically, the rotation mirror 13 is disposed on the optical path of the light L2. The light L2 is incident on a reflecting surface 131 of the rotation mirror 13. The light L2 incident on the reflective surface 131 is reflected by the reflective surface 131. The reflective surface 131 reflects the light L2 toward the iris camera 12 (in particular, toward the optical system 121). As a result of that, even when the iris camera 12 faces the direction different from the direction in which the target person P exists, the iris camera 12 is capable of imaging the target person P.

The light L2 enters the iris camera 12 (in particular, the optical system 121) through the opening 195 (see FIGS. 5 and 7) formed in the housing 19 (in particular, the front housing 191). Further, when the iris camera 12 is supported by the support plate 18, the light from the target person P may enter the iris camera 12 (in particular, the optical system 121) through an opening 185 formed in the support plate 18. As a result of that, the iris camera 12 housed in the housing 19 can generate the iris image IMG_I by capturing the image of the target person P positioned outside the housing 19.

It is as described above that the light L2 reflected on the rotation mirror 13 toward the iris camera 12 may include at least one (e.g., near-infrared light) of the reflected light and the scattered light with respect to the illumination light emitted from the iris. In this case. In this case, the opening 195 may be filled with a member which absorbs or reflects a part of visible light while allowing near-infrared light to pass therethrough. The opening 195 may be filled with a member which exhibits a desired color with respect to visible light while allowing near-infrared light to pass therethrough. As a result of that, the design of the appearance of the housing 19 (i.e., the design of the appearance of the imaging unit 1) is improved. Furthermore, since the design could make the target person P difficult to recognize through the opening 195 the internal structure of the imaging unit 1, it is easy to guide the line of sight of the target person P to the display which is exposed to the outside of the imaging unit 1.

Figure 8:
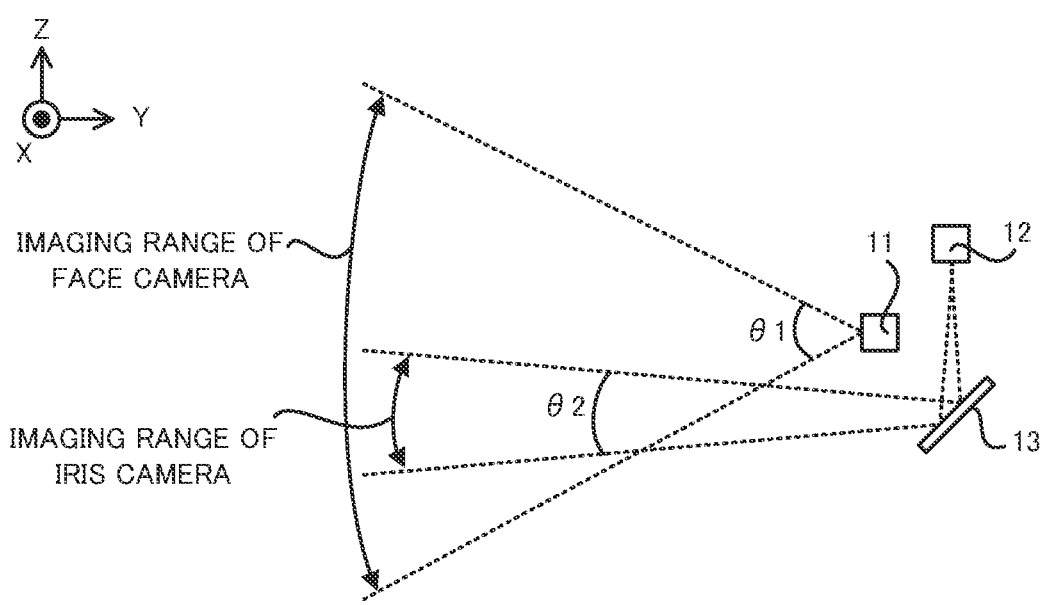
FIG. 8 is a cross-sectional view showing an imaging range of the face camera and an imaging range of the iris camera.
Figure 9:
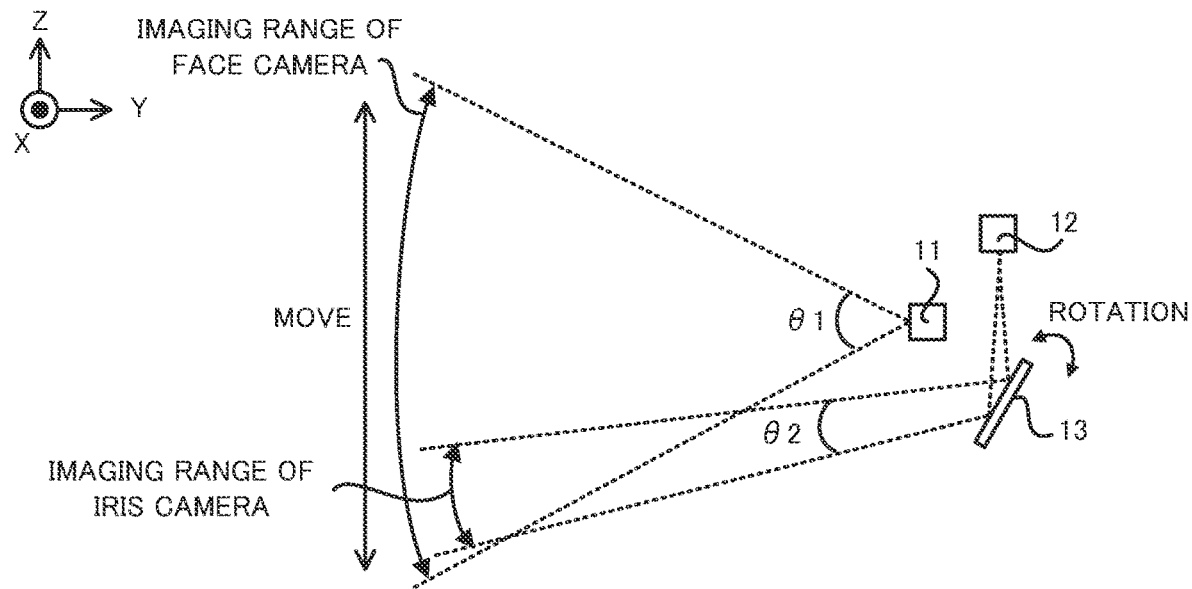
FIG. 9 is a cross-sectional view showing an imaging range of the face camera and an imaging range of the iris camera.

The size of the imaging range of the face camera 11 may be different from the size of the imaging range of the iris camera 12. Specifically, as shown in FIG. 8, the imaging range of the face camera 11 may be wider than that of the iris camera 12. That is, the angle of view θ1 of the face camera 11 may be larger than the angle of view θ2 of the iris camera 12. In this case, due to the difference in the height of the target person P or the like, the eyes of the target person P are not always positioned at a particular position within the imaging range of the face camera 11. For example, while the eyes of a first target person P having a first height is positioned in a first position in the imaging range of the face camera 11, and the eyes of a second target person P having a second height lower than the first height may be positioned in a second position lower than the first position in the imaging range of the face camera 11. However, since the angle of view θ2 of the iris camera 12 is relatively small, the imaging range of the iris camera 12 does not always include both the eyes of the first target person P and the eyes of the second target person P. Therefore, in the second example embodiment, the imaging unit 1 may move the imaging range of the iris camera 12 by rotating the rotation mirror 13 using the rotation motor 14. That is, the imaging unit 1 may move the imaging range of the iris camera 12 by changing the orientation of the rotation mirror 13 using the rotation motor 14. For example, the imaging unit 1 may move the imaging range of the iris camera 12 along the longitudinal direction (in other words, the vertical direction, for example, the Z-axis direction) by rotating the rotation mirror 13, as shown in FIG. 9. Specifically, the imaging unit 1 may move the imaging range of the iris camera 12 along the longitudinal direction by rotating the rotation mirror 13 about an axis of rotation, the axis intersecting the direction in which the imaging range of the iris camera 12 is moved (for example, the axis of rotation extending along the horizontal direction). As an example, the imaging unit 1 may move the imaging range of the iris camera 12 along the longitudinal direction (e.g., the axis of rotation extending along the X-axis) by rotating the rotation mirror 13 about the axis of rotation, the axis intersecting both directions: the direction in which the imaging range of the iris camera 12 is moved (e.g., the Z-axis direction) and the direction in which the target person P is present (e.g., the Y-axis direction).

Figure 10:
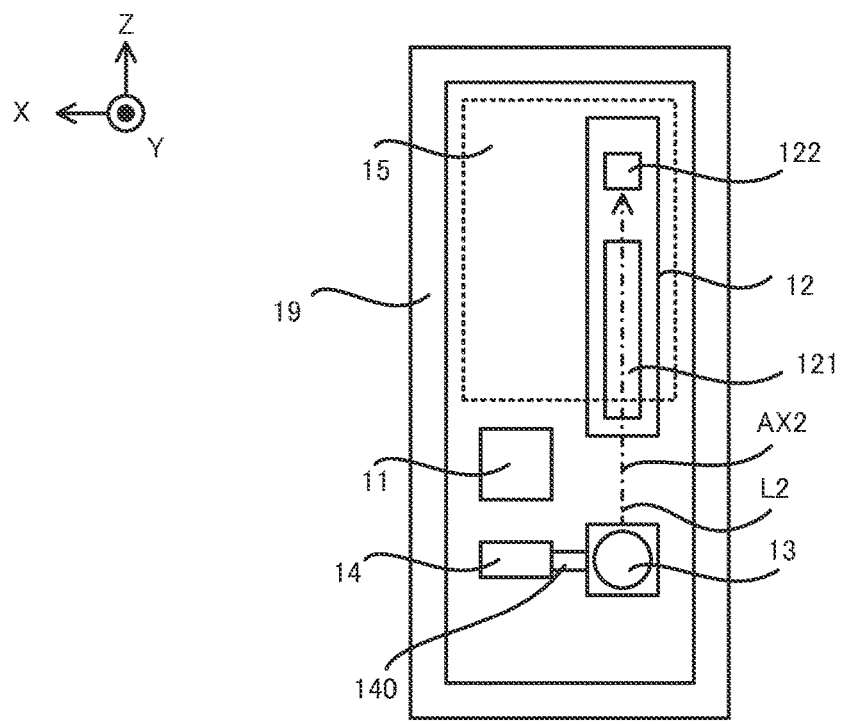
FIG. 10 is a cross-sectional view showing a cross-section of the imaging unit in the second example embodiment (in particular, a cross-section including a rotation motor).

If the rotation mirror 13 is rotated around the axis of rotation along the horizontal direction, as shown in FIG. 10, the rotation motor 14 for rotating the rotation mirror 13 may be disposed in the housing 19 so that the motor shaft 140 of the rotation motor 14 extends along the horizontal direction. In this case, the horizontal size of the rotation motor 14 (i.e., the size with respect to the direction in which the motor shaft 140 extends) is one element that determines the horizontal size of the imaging unit 1. Specifically, the horizontal size of the imaging unit 1 is larger than the horizontal size of the rotation motor 14. However, since the horizontal size of the rotation motor 14 does not become excessively large, the horizontal size of the imaging unit 1 does not become excessively large.

Again in FIGS. 6 and 7, the display 15 is housed in the housing 19 so that the display surface 151 capable of displaying information is exposed to the outside of the housing 19. Specifically, the display 15 is housed in the housing 19 so that the display surface 151 is exposed to the outside of the housing 19 through an opening 196 (see from FIG. 5 to FIG. 7) formed in the housing 19 (in particular, the front housing 191). That is, the display 15 is housed in the housing 19 so that the display surface 151 is recognized through the opening 196 from the outside of the housing 19.

Within the housing space SP1, the space SP2 (see FIG. 7) adjacent to the display 15 may be used as a space for housing at least a part of the iris camera 12. That is, at least a part of the iris camera 12 may be disposed in the space SP2 adjacent to the display 15. Specifically, at least a part of the iris camera 12 may be disposed in the space SP2 adjacent to the back surface 152 of the display 15 located opposite the display surface 151.

The distance sensor 16 is housed in the housing 19 so as to so as to measure a distance from the imaging unit 1 to the target person P through the opening 197 (see FIG. 5) formed in the housing 19 (in particular, the front housing 191). For example, if the distance sensor 16 capable of optically measuring the distance from the imaging unit 1 to the target person P is housed in the housing 19, the distance sensor 16 may be housed in the housing 19 so as to emit a measurement light through the opening 197 (e.g., to irradiate the measurement light to the target person P).

(2-3) Configuration of Control Unit 2

Figure 11:
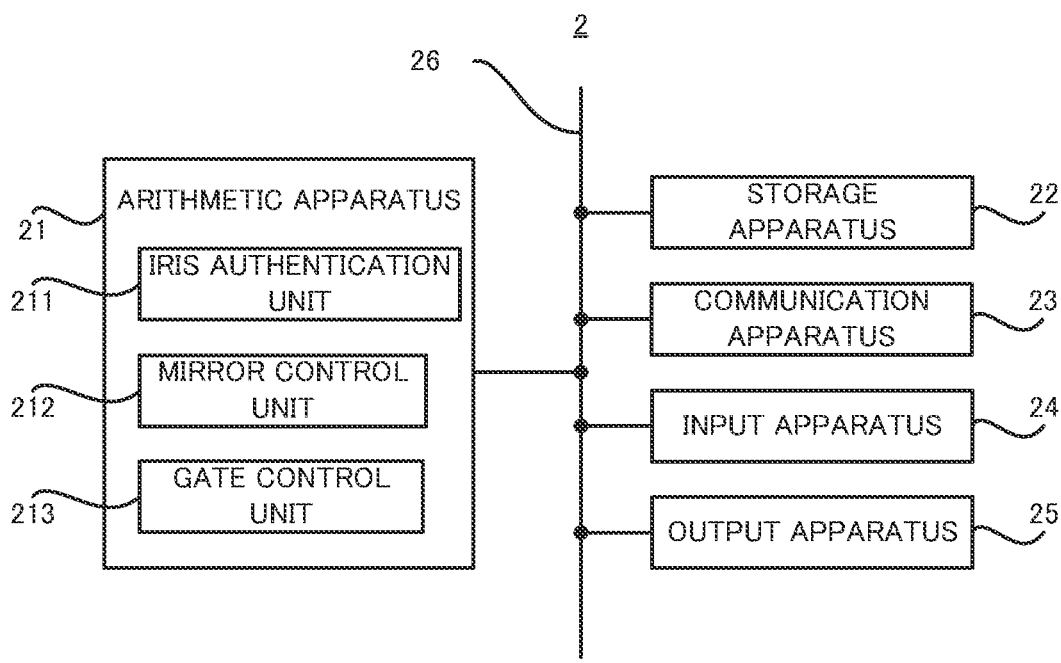
FIG. 11 is a block diagram showing a configuration of a control unit in the second example embodiment.

Subsequently, with reference to FIG. 11, a description will be given of a configuration of the control unit 2. FIG. 11 is a block diagram showing the configuration of the control unit 2.

As shown in FIG. 11, the control unit 2 includes an arithmetic apparatus 21, a storage apparatus 22, and a communication apparatus 23. Further, the control unit 2 may include an input apparatus 24 and an output apparatus 25. However, the control unit 2 may not include at least one of the input apparatus 24 and the output apparatus 25. The arithmetic apparatus 21, the storage apparatus 22, the communication apparatus 23, the input apparatus 24, and the output apparatus 25 may be connected via a data bus 26.

The arithmetic apparatus 21 includes, for example, at least one of a CPU (Central Processing Unit), GPUs (Graphics Processing Unit), FPGA (Field Programmable Gate Array), DSPs (Demand-Side Platform) and ASIC (Application Specific Integrated Circuit). The arithmetic apparatus 21 reads a computer program. For example, the arithmetic apparatus 21 may read a computer program stored in the storage apparatus 22. For example, the arithmetic apparatus 21 may read a computer program stored in a computer-readable and non-temporary recording medium using a recording medium reading apparatus (not illustrated) provided in the control unit 2. The arithmetic apparatus 21 may acquire (i.e., may download or read) a computer program from an apparatus (not illustrated) disposed outside the control unit 2 via a communication apparatus 23 (or another communication apparatus). The arithmetic apparatus 21 executes the loaded computer program. As a result of that, in the arithmetic apparatus 21, realized are logical functional blocks for executing operation to be performed by the control unit 2 (e.g., the authentication operation described above). That is, the operation apparatus 21 is capable of functioning as a controller for realizing the logical functional blocks for implementing operation (in other words, processes) to be executed by the control unit 2.

FIG. 11 shows an example of logical functional blocks implemented in the arithmetic apparatus 21 to perform the authentication operation. As shown in FIG. 11, the iris authentication unit 211, which is a specific example of the "authentication unit" in the supplementary notes to be described later, a mirror control unit 212, which is a specific example of the "rotation control unit" in the supplementary notes to be described later, and a gate control unit 213 are realized in the arithmetic apparatus 21. Since the respective operations of the iris authentication unit 211, the mirror control unit 212, and the gate control unit 213 will be described in detail later with reference to FIG. 12 and the like, a description thereof will be omitted.

The storage apparatus 22 is capable of storing desired data. For example, the storage apparatus 22 may temporarily store a computer program executed by the arithmetic apparatus 21. The storage apparatus 22 may temporarily store data used temporarily by the arithmetic apparatus 21 while the arithmetic apparatus 21 is executing a computer program. The storage apparatus 22 may store data that the control unit 2 stores long-term. The storage apparatus 22 may include at least one of a RAM (Random Access Memory), a ROM (Read Only Memory), a hard disk apparatus, a magnetic-optical disk apparatus, an SSD (Solid State Drive), and a disk array apparatus. That is, the storage apparatus 22 may include a non-temporary recording medium.

The communication apparatus 23 can communicate with each of the imaging unit 1 and the gate unit 3 via a communication network (not illustrated). In the second example embodiment, the communication apparatus 23 receives (that is, acquires) the person image IMG (specifically, the face image IMG_F and the iris image IMG_I) from the imaging unit 1. Furthermore, the communication apparatus 23 transmits to the imaging unit 1, an imaging control signal for controlling the imaging unit 1 to capture the image of at least a part of the target person P. The communication apparatus 23 transmits to the gate unit 3, a gate control signal for switching the state between the open state and the closed state with respect to each of the first flapper gate 32 and the second flapper gate 33.

The input apparatus 24 is an apparatus that accepts the input of information to the control unit 2 from the outside of the control unit 2. For example, the input apparatus 24 may include an operation apparatus (e.g., at least one of a keyboard, a mouse, and a touch panel) that an operator of the control unit 2 can operate. For example, the input apparatus 24 may include a readable apparatus that is capable of reading information recorded as data on a recording medium that can be externally attached to the control unit 2.

The output apparatus 25 is an apparatus for outputting information to the outside of the control unit 2. For example, the output apparatus 25 may output the information as an image. In other words, the output apparatus 25 may include a display apparatus (so-called display) capable of displaying an image representing the information to be output. For example, the output apparatus 25 may output the information as audio. That is, the output apparatus 25 may include an audio apparatus (so-called a speaker) capable of outputting audio. For example, the output apparatus 25 may output information on a paper. That is, the output apparatus 25 may include a print apparatus (so-called printer) capable of printing the desired information on the paper.

(2-4) Authentication Operation of Control Unit 2

Figure 12:
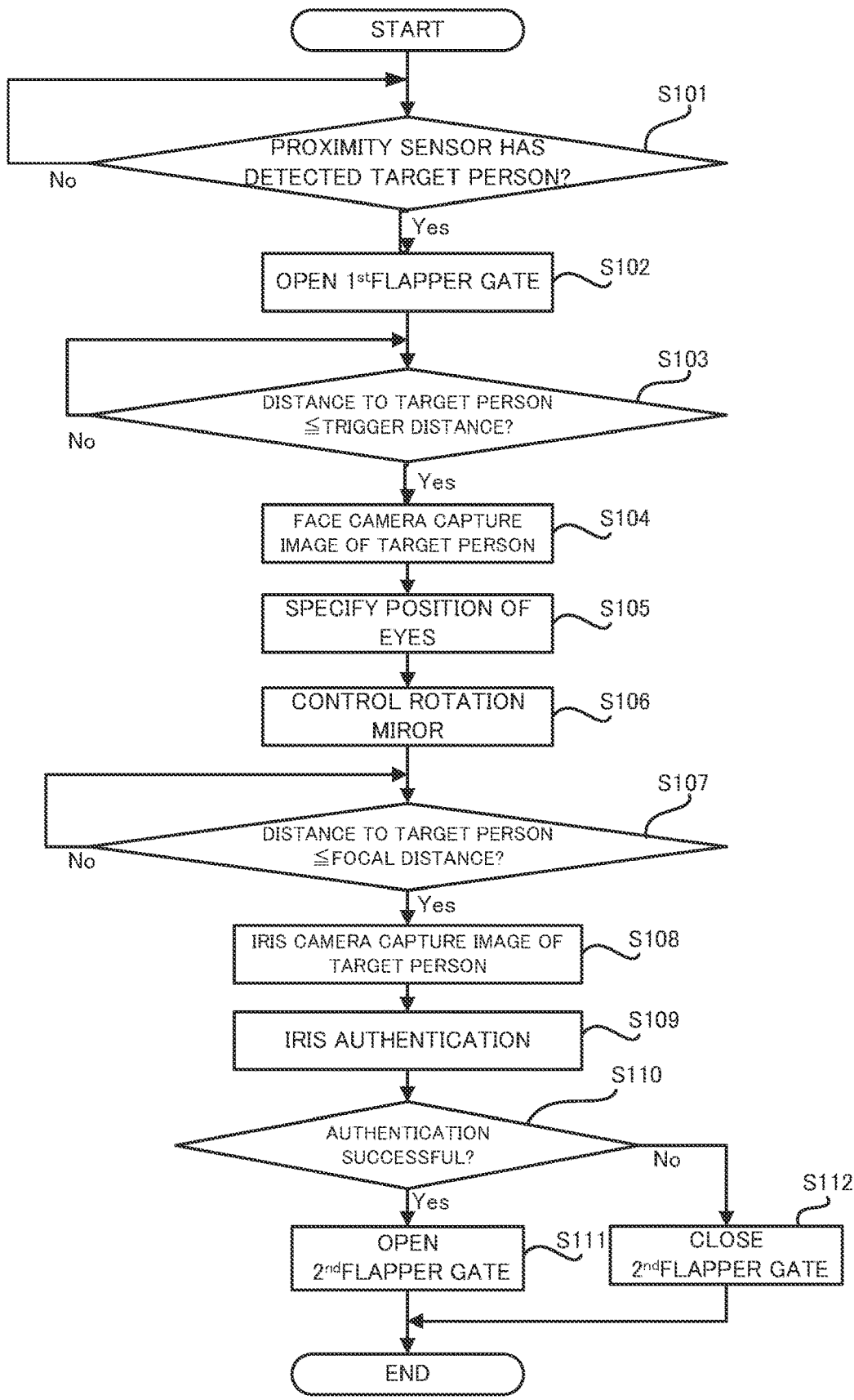
FIG. 12 is a flowchart showing a flow of authentication operation performed by the control unit in the second example embodiment.

Subsequently, referring to FIG. 12, the authentication operation performed by the control unit 2 will be described. FIG. 12 is a flowchart showing a flow of the authentication operation performed by the control unit 2.

As shown in FIG. 12, the gate control unit 213 determines whether the proximity sensor 34 of the gate unit 3 has detected the target person P (step S101).

As a result of the determination in step S101, when it is determined that the proximity sensor 34 does not detect the target person P (step S101: No), the gate control unit 213 continues to determine whether the proximity sensor 34 detects the target person P. In this case, the gate control unit 213 may transmit via the communication apparatus 23 to the gate unit 3, the gate control signal for setting the state of the first flapper gate 32 to the closed state. As a result of that, the state of the first flapper gate 32 is maintained in the closed state.

Figure 13:
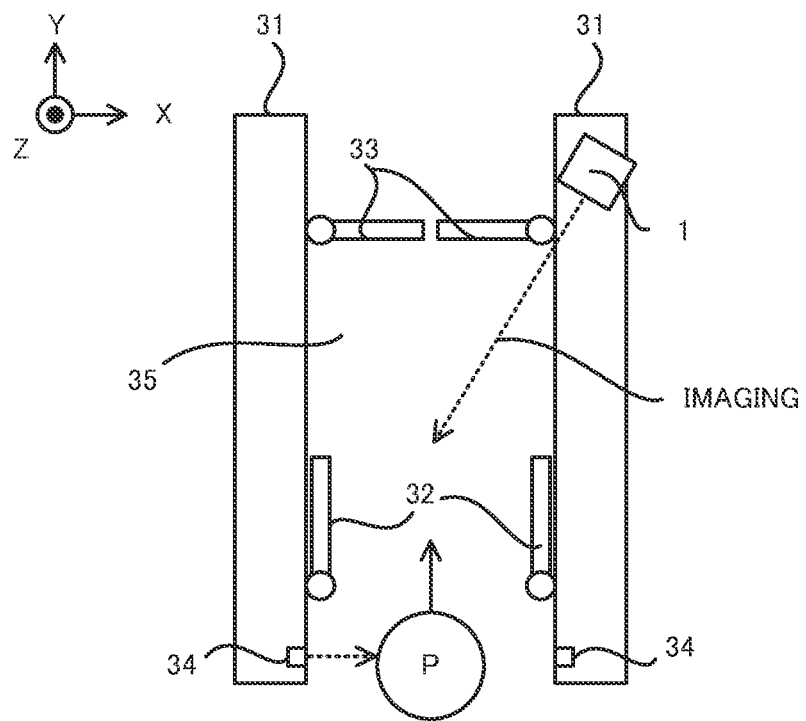
FIG. 13 is a plan view showing the gate unit in which the state of a first flapper gate has become an open state.

On the other hand, as a result of the determination in step S101, when it is determined that the proximity sensor 34 has detected the target person P (step S101: Yes), the gate control unit 213 transmits via the communication apparatus 23 to the gate unit 3, the gate control signal for setting the state of the first flapper gate 32 to the open state, (step S102). As a result of that, as shown in FIG. 13, the state of the first flapper gate 32 is switched to the open state, and the target person P is allowed to enter the lane 35. However, as described above, when the proximity sensor 34 has detected the target person P, the gate unit 3 may switch the state of the first flapper gate 32 to the open state independently from the control by the gate control unit 213.

When the face camera 11 is capable of imaging the face of the target person P that has not passed through the first flapper gate 32, in step S101, the gate control unit 213 may authenticate the target person P based on the face image IMG_F generated by the face camera 11. In this case, if the authentication is successful, in step S102, the gate control unit 213 may transmit to the gate unit 3, the gate control signal for setting the state of the first flapper gate 32 to the open state.

In FIG. 12, thereafter, the iris authentication unit 211 determines whether or not the distance from the imaging unit 1 to the target person P is equal to or less than a predetermined trigger distance on the basis of the detection result by the distance sensor 16 (step S103). The trigger distance may be a distance from the imaging unit 1 to a position where the face camera 11 is in focus. In this case, the operation of determining whether or not the distance from the imaging unit 1 to the target person P is equal to or less than the trigger distance, is equivalent to the operation of determining whether or not the target person P which has entered the lane 35 has reached the position where the face camera 11 is in focus.

As a result of the determination in step S103, when it is determined that the distance from the imaging unit 1 to the target person P is not equal to or less than the trigger distance (step S103: No), it is estimated that the target person P that has entered the lane 35 has not yet reached the position where the face camera 11 is in focus. In this case, the iris authentication unit 211 continuously determines whether or not the distance from the imaging unit 1 to the target person P is equal to or less than the trigger distance.

On the other hand, as a result of the determination in step S103, when it is determined that the distance from the imaging unit 1 to the target person P is equal to or less than the trigger distance (step S103: Yes), it is estimated that the target person P has entered the lane 35 has already reached the position where the face camera 11 is in focus. In this case, the iris authentication unit 211 transmits via the communication apparatus 23 to the imaging unit 1, the imaging control signal for controlling the face camera 11 to capture the image of the face of the target person P (step S104). As a result of that, the face camera 11 captures the image of the face of the target person P. However, as described above, when the distance from the imaging unit 1 to the target person P becomes equal to or less than the trigger distance, the face camera 11 may image the face of the target person P independently from the control performed by the iris authentication unit 211.

Figure 14:
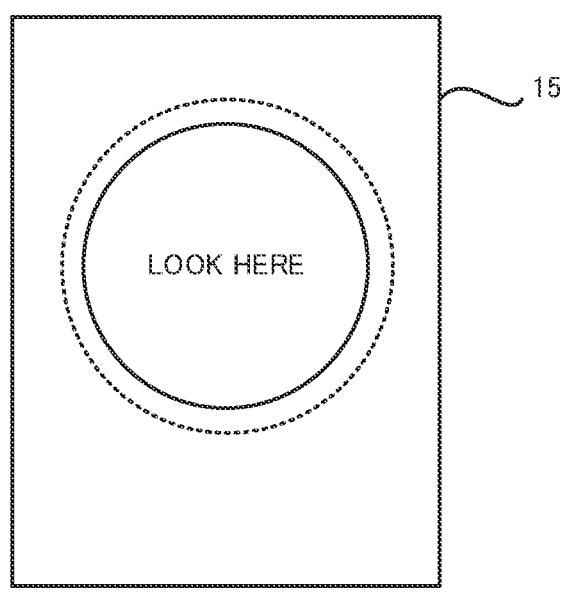
FIG. 14 shows an example of a UI screen displayed on the display when the face camera captures the image of a face of a target person.

When the face camera 11 captures the image of the face of the target person P, the iris authentication unit 211 may transmit via the communication apparatus 23 to the imaging unit 1, the imaging control signal for controlling the display 15 to display a predetermined UI (User Interface) screen. The predetermined UI screen may include, for example, a screen prompting the target person P to face to the face camera 11. An example of the UI screen prompting the target person P to face to the face camera 11 is shown in FIG. 14. FIG. 14 shows, as an example of the UI screen, the UI screen including a message prompting the target person P to face to the display 15 (that is, face to the face camera 11 disposed with the display 15) together with a round frame indicating the position of the face of the target person P.

Figure 15:
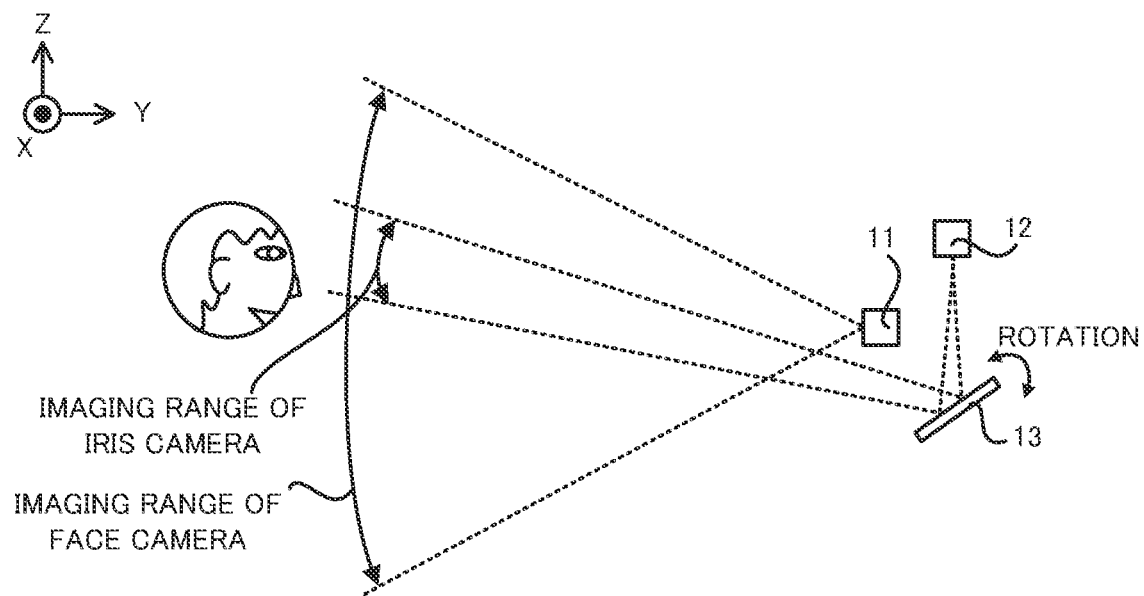
FIG. 15 is a cross-sectional view showing a positional relation between an imaging range of the iris camera and eyes of the target person.

In FIG. 12, thereafter, the iris authentication unit 211 acquires the face image IMG_F from the face camera 11 via the communication apparatus 23 and specifies the position of the eyes of the target person P (in particular, the position in the vertical direction, for example, the position in the Z-axis direction) on the basis of the acquired face image IMG_F (step S105). Thereafter, the iris authentication unit 211 transmits via the communication apparatus 23 to the imaging unit 1, the imaging control signal for rotating the rotation mirror 13 so that the iris camera 12 can image the eyes at the position specified in step S105 (step S106). That is, the iris authentication unit 211 transmits via the communication apparatus 23 to the imaging unit 1, the imaging control signal for rotating the rotation mirror 13 so that the eyes positioned at the position specified in step S105 is included in the imaging range of the iris camera 12 (step S106). As a result of that, as shown in FIG. 15, the rotation motor 14 rotates the rotation mirror 13 on the basis of the imaging control signal, so that the iris camera 12 can image the eyes of the target person P.

When the iris camera 12 captures the image of the eyes of the target person P, the illumination apparatus 36 illuminates the eyes of the target person P with the illumination light IL. For example, since the iris camera 12 captures the image of the eyes of the target person P after the rotation mirror 13 has rotated in step S106, the illumination apparatus 36 may start illuminating the eyes of the target person P with the illumination light IL before the rotation mirror 13 is rotated in step S106. For example, since the iris camera 12 captures the image of the eyes of the target person P after the face camera 11 captures the image of the face of the target person P in step S104, the illumination apparatus 36 may start illuminating the eyes of the target person P with the illumination light IL after the face camera 11 captures the image of the face of the target person P in step S104. For example, since the iris camera 12 captures the image of the eyes of the target person P after the first flapper gate 32 has got opened in step S102, the illumination apparatus 36 may start illuminating the eyes of the target person P with the illumination light IL after the first flapper gate 32 has got opened in step S102.

In FIG. 12, thereafter, the iris authentication unit 211 determines whether or not the distance from the imaging unit 1 to the target person P is equal to or less than the predetermined focal distance based on the detection result by the distance sensor 16 (step S107). The focal distance may be a distance from the imaging unit 1 to a position where the iris camera 12 is in focus. In this case, the operation of determining whether or not the distance from the imaging unit 1 to the target person P is equal to or less than the focal distance is equivalent to the operation of determining whether or not the target person P that has entered the lane 35 has reached the position where the iris camera 12 is in focus. It should be understood that typically, the focal distance is less than the trigger distance described above.

As a result of the determination in step S107, when it is determined that the distance from the imaging unit 1 to the target person P is not equal to or less than the focal distance (step S107: No), it is estimated that the target person P that has entered the lane 35 has not yet reached the position where the iris camera 12 is in focus. In this case, the iris authentication unit 211 continuously determines whether or not the distance from the imaging unit 1 to the target person P is equal to or less than the focal distance.

On the other hand, when it is determined that the distance from the imaging unit 1 to the target person P is equal to or less than the focal distance (step S107: Yes) as a result of the determination in step S107, it is estimated that the target person P that has entered the lane 35 has already reached the position where the iris camera 12 is in focus. In this case, the iris authentication unit 211 transmits, via the communication apparatus 23 to the imaging unit 1, the imaging control signal for controlling the iris camera 12 to capture the image of the eyes of the target person P (step S108). As a result of that, the iris camera 12 captures the image of the face of the target person P. However, as described above, when the distance from the imaging unit 1 to the target person P becomes equal to or less than the focal distance, the iris camera 12 may image the eyes of the target person P independently from the control performed by the iris authentication unit 211.

When the iris camera 12 captures the image of the eyes of the target person P, similarly to the event where the face camera 11 captures the image of the face of the target person P, the iris authentication unit 211 may also transmit an imaging control signal for controlling the display 15 to display the predetermined UI screen via the communication apparatus 23 to the imaging unit 1.

Then, the iris authentication unit 211 acquires the iris image IMG_I from the iris camera 12 via the communication apparatus 23, and authenticates the target person P based on the acquired iris image IMG_I (step S109).

Figure 16:
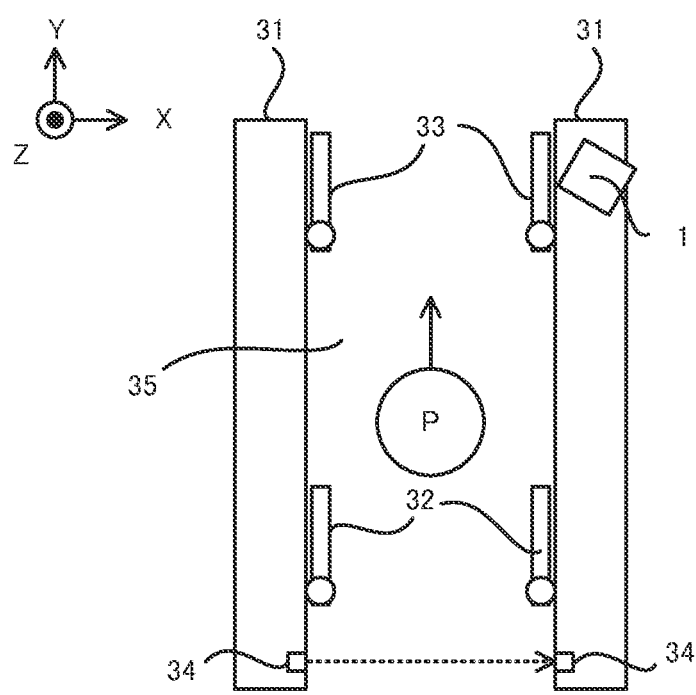
FIG. 16 is a plan view showing the gate unit in which the state of a second flapper gate has become an open state.
Figure 17:
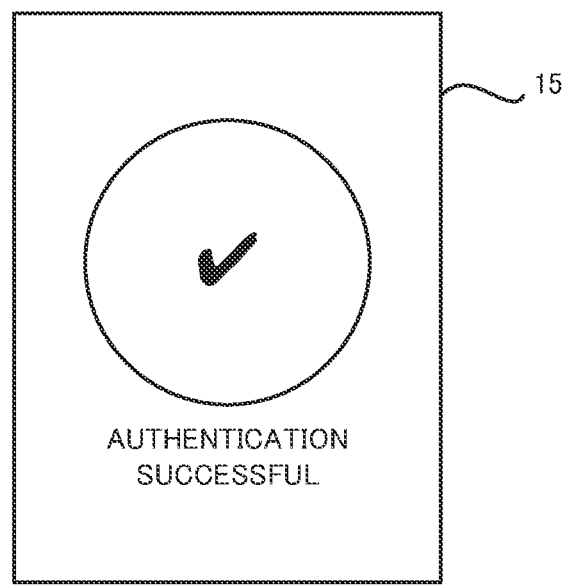
FIG. 17 shows an example of a UI screen displayed on the display when the target person has been successfully authenticated.

When the authentication of the target person P is successful as a result of the authentication in step S109 (step S110: Yes), the gate control unit 213 transmits the gate control signal for setting the state of the second flapper gate 33 to the open state via the communication apparatus 23 to the gate unit 3 (Step S111). As a result of that, as shown in FIG. 16, the state of the second flapper gate 33 is switched to the open state, and the target person P is allowed to pass through the lane 35. Further, when the target person P is successfully authenticated, as illustrated in FIG. 17, the iris authentication unit 211 may transmit via the communication apparatus 23 to the imaging unit 1, the imaging control signal for controlling the display 15 to display the UI screen for notifying the target person P of the fact that the authentication is successful.

Figure 18:
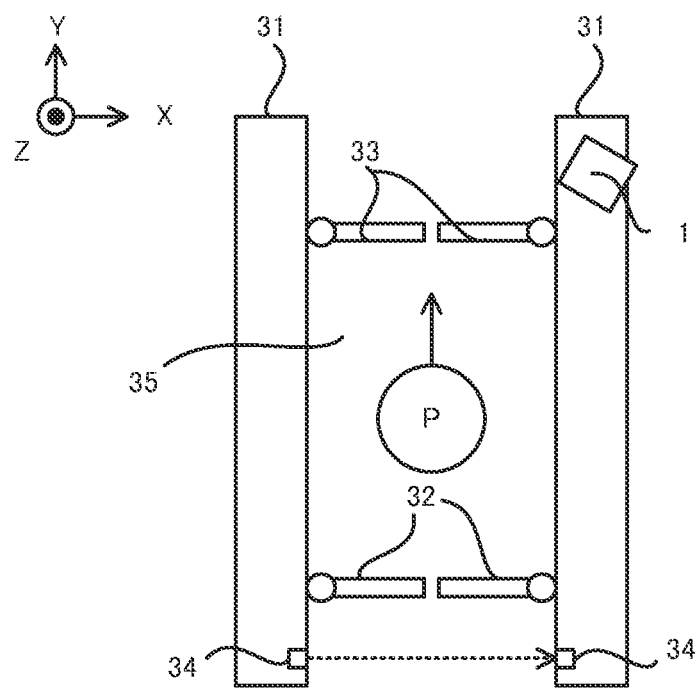
FIG. 18 is a plan view showing the gate unit in which the state of the first and second flapper gates is closed.
Figure 19:
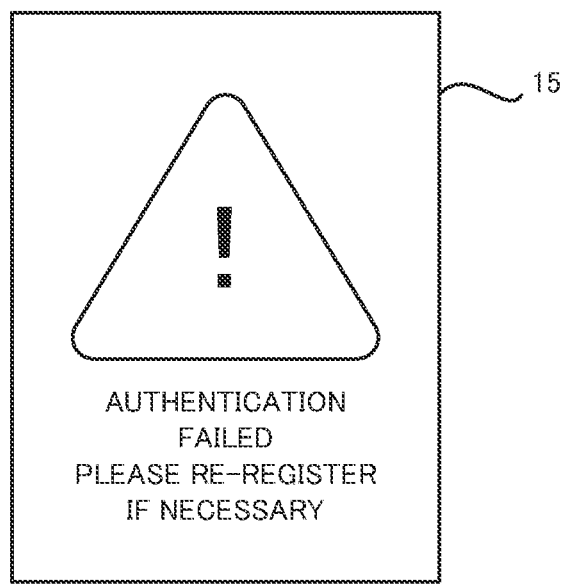
FIG. 19 shows an example of a UI screen displayed on the display when authentication of the target person has failed.

On the other hand, in FIG. 12, if the authentication of the target person P is not successful (that is, failed) as a result of the authentication in step S109 (step S110: No), the gate control unit 213 transmits the gate control signal for setting the state of the second flapper gate 33 to the closed state via the communication apparatus 23 to the gate unit 3 (step S112). As a result of that, as shown in FIG. 18, the state of the second flapper gate 33 is maintained in the closed state, and the target person P cannot pass through the lane 35. At this time, the gate control unit 213 may transmit via the communication apparatus 23 to the gate unit 3, the gate control signal for setting the state of the first flapper gate 32 to the closed state. As a result, as shown in FIG. 18, the target person P is confined between the first flapper gate 32 and the second flapper gate 33. In this case, the target person P may take an action according to instructions of the staff or the like managing the gate unit 3. Further, when the authentication of the target person P is not successful, as illustrated in FIG. 19, the iris authentication unit 211 may transmit via the communication apparatus 23 to the imaging unit 1, the imaging control signal for controlling the display 15 to display the UI screen for notifying the target person P of the fact that the authentication is not successful. Further, when the authentication of the target person P is not successful, as shown in FIG. 19, the iris authentication unit 211 may transmit via the communication apparatus 23 to the imaging unit 1, the imaging control signal for controlling the display 15 to display the UI screen for prompting the target person P to re-register the iris pattern of the subject person P in the authentication system SYS (that is, to register the target person P as the registered person). Further, when the authentication of the target person P is not successful, the iris authentication unit 211 may transmit via the communication apparatus 23. to the imaging unit 1, the imaging control signal for controlling the display 15 so as to display the UI screen for prompting the target person P to perform the iris authentication again (that is, to re-image the iris of the target person P by the iris camera 12).

(2-5) Technical Effect of Authentication System SYS

As described above, in the authentication system SYS of the second example embodiment, the iris camera 12 is arranged so as to face a direction different from the direction in which the target person P exists. As a result of that, compared with the case where the iris camera 12 is disposed so as to face the direction in which the target person P is present, it is possible to reduce the size of the authentication system SYS (in particular, to reduce the size of the imaging unit 1 including the iris camera 12).

Specifically, the iris camera 12 for imaging the iris of the target person P generally includes the optical system 121 (for example, the optical system called a telephoto lens) having a narrow angle of view and/or a long focal length as compared with the optical system 111 of the face camera 11. In this case, as compared with the optical system 111, the size of the optical system 121 along the optical axis direction is increased. As a result of that, assuming that the iris camera 12 is facing the direction (for example, the lateral direction) in which the target person P is present, there is a possibility that the size (so-called, the width or the depth) of the imaging unit 1 in the lateral direction becomes excessively large. However, in the second example embodiment, the iris camera 12 faces a direction (for example, the longitudinal direction, in other words, the vertical direction) different from the direction in which the target person P is present. Therefore, the possibility that the size of the imaging unit 1 in the lateral direction becomes excessively large is relatively low. Therefore, it is possible to reduce the size of the imaging unit 1.

Further, as a space for placing the iris camera 12 facing in a direction different from the direction in which the target person P is present (for example, a direction different from the horizontal direction, as an example, the vertical direction), the space SP2 adjacent to the display 15 is available, the display having the display surface 151 extending in a direction different from the horizontal direction (e.g., the vertical direction). The Space SP2 adjacent to the display 15 comprising the display surface 151 extending in a direction different from the lateral direction (e.g., the vertical direction) is generally a space extending in a direction different from the lateral direction (e.g., in the vertical direction). In the second example embodiment, by using the space SP2 extending in a direction different from such a lateral direction (e.g., extending in the longitudinal direction), it is possible to appropriately place the iris camera 12 facing in a direction different from the lateral direction (e.g., facing in the longitudinal direction). That is, the space SP2 that inevitably occurs due to placing the display 15 can be effectively utilized as a space for placing the iris camera 12. Therefore, compared with the case where a space should be secured specifically for placing the iris camera 12, the size of the imaging unit 1 can be reduced.

Thus, the authentication system SYS in the second example embodiment is possible to appropriately solve the technical problems of desiring to reduce the size of the imaging unit 1.

In the second example embodiment, the imaging unit 1 rotates the rotation mirror 13 so that the iris camera 12 can image the eyes of the target person P that are present at a position specified based on the face image IMG_F. That is, the imaging unit 1 can move the imaging range of the iris camera 12 using the rotation mirror 13 so that the eyes of the target person P present at the position specified based on the face image IMG_F are included in the imaging range of the iris camera 12. As a result of that, the imaging unit 1 can image using a single iris camera 12, the eyes of the target person P which exist at various positions (typically with respect to the height). Therefore, as compared with the imaging unit of the comparative example including two or more iris cameras 12 for imaging the eyes of the target person P which exist various positions (typically, with respect to the height), the size of the imaging unit 1 can be reduced.

Further, when at least a part of the support plate 18 is exposed to the outside of the housing 19, the heat generated by the face camera 11, the iris camera 12 and the display 15 which are supported by the support plate 18 can be released via the support plate 18 to the outside of the housing 19. Therefore, the influence of heat on the operation of the face camera 11, the iris camera 12, and the display 15 is reduced.

(3) Third Example Embodiment

Subsequently, a third example embodiment of the authentication system and the imaging apparatus will be described. The following describes the authentication system SYSa to which the third example embodiment of the authentication system and the imaging apparatus is applied. The authentication system SYSa, as compared with the authentication system SYS described above, differs in that the authentication system SYSa comprises an imaging unit 1a instead of the imaging unit 1. The other features of the authentication system SYSa may be identical to the other features of the authentication system SYS.

Figure 20:
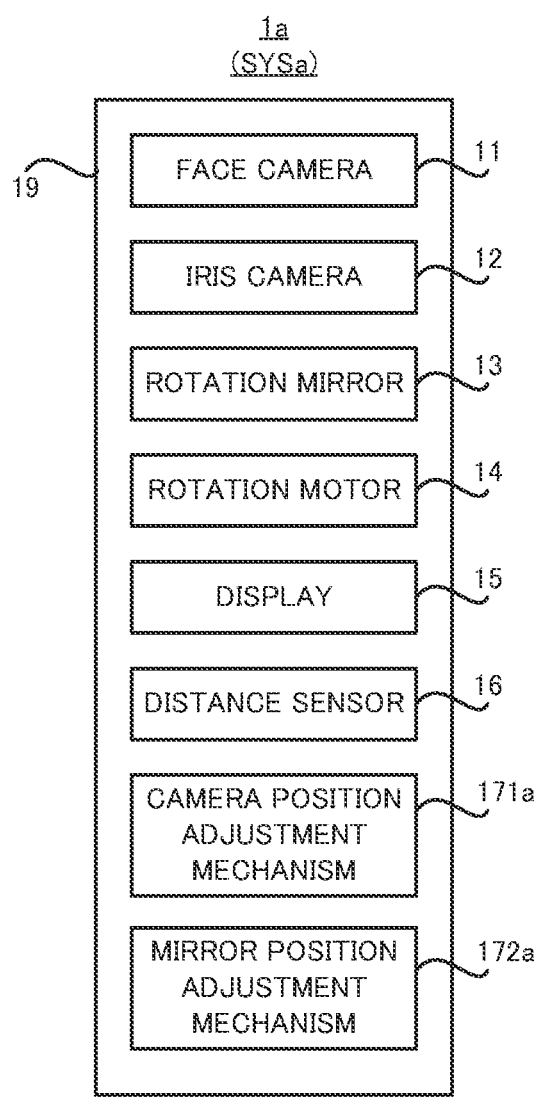
FIG. 20 is a block diagram showing a configuration of an imaging unit in the third example embodiment.

Hereinafter, with reference to FIG. 20, a description will be given with respect to the imaging unit 1a in the third example embodiment. FIG. 20 is a block diagram showing a configuration of the imaging unit 1a in the third example embodiment. In the following description, the components already described will not be described in detail by denoting the same reference numerals.

As shown in FIG. 20, the imaging unit 1a differs from the imaging unit 1 described above in that the imaging unit 1a comprises at least one of: a camera position adjustment mechanism 171a, which is a specific example of the "first position adjustment unit" in the supplementary notes described later, and; a mirror position adjustment mechanism 172a, which is a specific example of the "second position adjustment unit" in the supplementary notes described later. The other features of the imaging unit 1a may be identical to the other features of the imaging unit 1.

Figure 21:
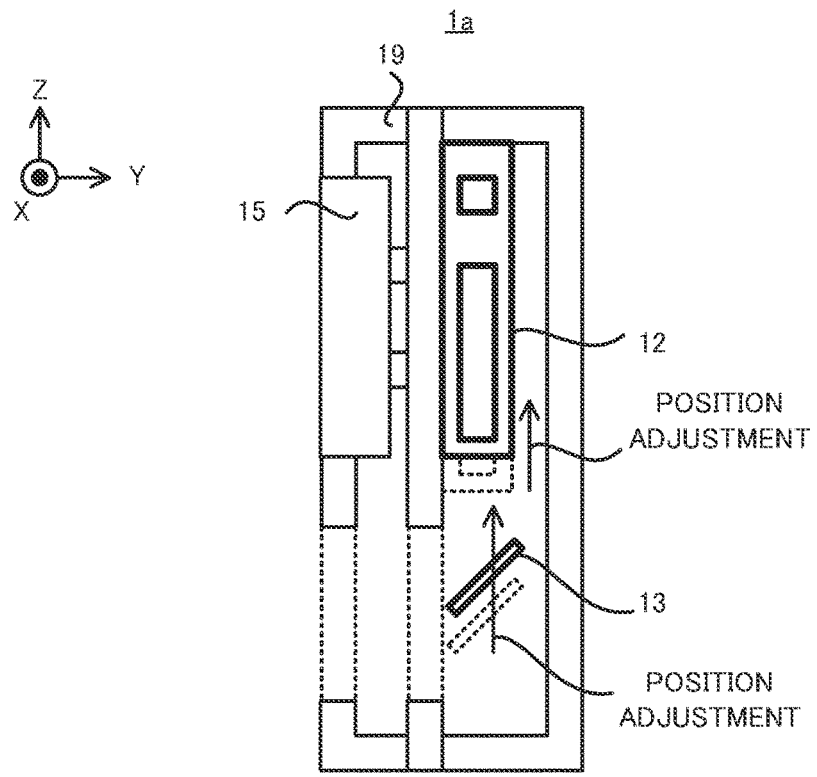
FIG. 21 is a cross-sectional view showing an iris camera and a rotation mirror whose positions are adjusted.

The camera position adjustment mechanism 171a is an apparatus capable of adjusting the position of the iris camera 12. For example, as shown in FIG. 21 showing the iris camera 12 whose position could be adjusted, the camera position adjustment mechanism 171a may be capable of adjusting the position of the iris camera 12 along at least one of the X-axis direction, the Y-axis direction, and the Z-axis direction. In this case, the camera position adjusting mechanism 171a may adjust the position of the iris camera 12 by using a guide member comprising a slider that is movable in a predetermined direction and also to which the iris camera 12 is attachable.

The camera position adjustment mechanism 171a may adjust the position of the iris camera 12 by moving the iris camera 12. For example, the camera position adjustment mechanism 171a may adjust the position of the iris camera 12 by moving the iris camera 12 using power generated by a drive source such as a motor. In this instance, the operator of the authentication system SYSa does not have to manually move the iris camera 12. Alternatively, the operator of the authentication system SYSa may manually move the iris camera 12. In this case, the camera position adjustment mechanism 171a may move the iris camera 12 using a force applied to the iris camera 12 by the operator to move the iris camera 12.

The camera position adjustment mechanism 171a may adjust the position of the iris camera 12 based on the optical characteristics of the optical system 121 of the iris camera 12. For example, the camera position adjustment mechanism 171a may adjust the position of the iris camera 12 based on the focal length of the optical system 121. As an example, the camera position adjusting mechanism 171a may adjust the position of the iris camera 12 based on the focal length of the optical system 121 so that the iris camera 12 can image the target person P being distant an in-focus distance away from the imaging unit 1, the in-focus distance being determined based on the focal length.

The camera position adjustment mechanism 171a may adjust the position of the iris camera 12 based on a distance between the iris camera 12 and the target person P. For example, when the distance between the iris camera 12 and the target person P is longer than the above-described in-focus distance, the camera position adjustment mechanism 171a may shorten the distance between the iris camera 12 and the target person P by moving the iris camera 12 so that the iris camera 12 approaches the rotation mirror 13 so that the distance between the iris camera 12 and the target person P approaches the in-focus distance. For example, when the distance between the iris camera 12 and the target person P is shorter than the above-described in-focus distance, the camera position adjustment mechanism 171a may increase the distance between the iris camera 12 and the target person P by moving the iris camera 12 so that the iris camera 12 moves away from the rotation mirror 13 so that the distance between the iris camera 12 and the target person P approaches the in-focus distance. In this case, in particular, if the camera position adjustment mechanism 171a automatically moves the iris camera 12 using power generated by a driving source such as a motor, it is possible to maintain a state in which the iris camera 12 can appropriately take an image of the eyes of the target person P without bothering the operator.

The camera position adjustment mechanism 171a may be capable of adjusting the position of the face camera 11 in addition to or instead of the position of the iris camera 12.

The mirror position adjustment unit 172a is an apparatus capable of adjusting the position of the rotation mirror 13. For example, as shown in FIG. 21 showing the rotation mirror 13 whose position could be adjusted, the mirror position adjustment mechanism 172a may be capable of adjusting the position of the rotation mirror 13 along at least one of the X-axis direction, the Y-axis direction, and the Z-axis direction. In this case, the mirror position adjustment mechanism 172a may adjust the position of the rotation mirror 13 by using a guide member comprising a slider that is movable in a predetermined direction and also to which the mirror 13 is attachable.

The mirror position adjustment mechanism 172a may adjust the position of the rotation mirror 13 by moving the rotation mirror 13. For example, the mirror position adjustment mechanism 172a may adjust the position of the rotation mirror 13 by moving the rotation mirror 13 using power generated by a drive source such as a motor. In this instance, the operator of the authentication system SYSa does not have to move the rotation mirror 13 manually. Alternatively, the operator of the authentication system SYSa may manually move the rotation mirror 13. In this case, the mirror position adjustment mechanism 172a may move the rotation mirror 13 by using a force applied to the rotation mirror 13 by the operator to move the rotation mirror 13.

The mirror position adjusting mechanism 172a may adjust the position of the rotation mirror 13 so that the light from the target person P is appropriately incident on the optical system 121 of the iris camera 12. For example, since the position of the eyes of the target person P can be specified based on the face image IMG_F as described above, the mirror position adjustment mechanism 172a may move the rotation mirror 13 based on the specified position of the eyes. As an example, the mirror position adjustment mechanism 172a may move the rotation mirror 13 so that the rotation mirror 13 is positioned at a height corresponding to the height of the specified position of the eyes. More specifically, the mirror position adjustment mechanism 172a may adjust the height of the rotation mirror 13 so that the light L2 from the eyes positioned at the specified height is appropriately incident on the iris camera 12 via the rotation mirror 13. In this case, in particular, if the mirror position adjustment mechanism 172a automatically moves the rotation mirror 13 using power generated by a driving source such as a motor, it is possible to maintain the state in which the iris camera 12 can properly image the eyes of the target person P without bothering the operator.

Figure 22:
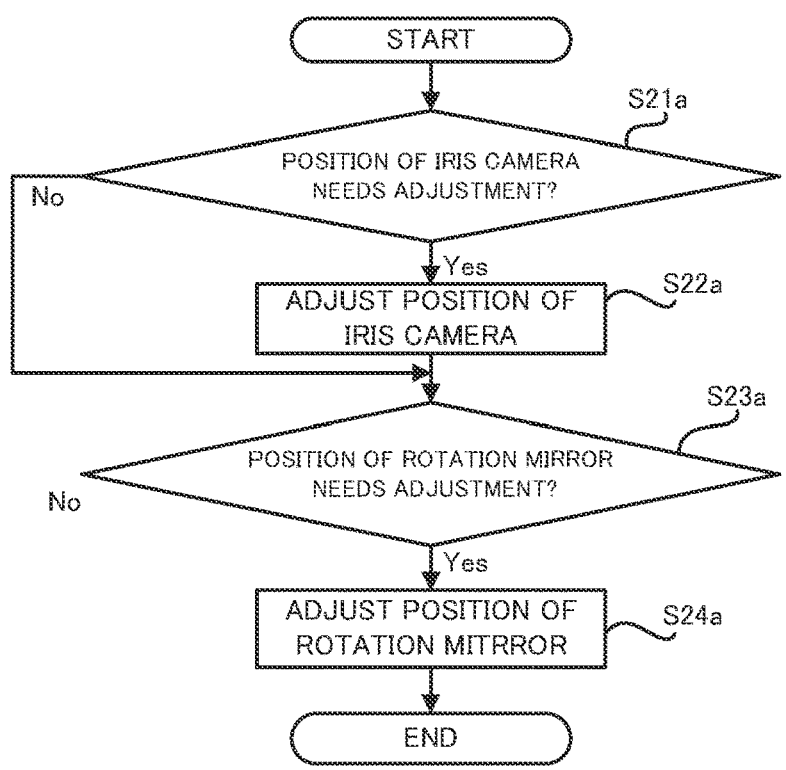
FIG. 22 is a flowchart showing a flow of operations for adjusting the positions of the iris camera and the rotation mirror in the third example embodiment.

In the third example embodiment, the imaging unit 1a may adjust the position of at least one of the iris camera 12 and the rotation mirror 13 according to the flowchart shown in FIG. 22. The operation shown in FIG. 22 may be performed in parallel with, before, or after the operation shown in FIG. 12. Specifically, as shown in FIG. 22, when it is determined that the position of the iris camera 12 needs to be adjusted (step S21a: YES), the camera position adjustment mechanism 171a may adjust the position of the iris camera 12 (step S22a). For example, it may be determined that the position of the iris camera 12 needs to be adjusted if the optical characteristics of the optic system 121 of the iris camera 12 change. Further, when it is determined that the position of the rotation mirror 13 needs to be adjusted (step S23a: YES), the mirror position adjustment mechanism 172a may adjust the position of the rotation mirror 13 (step S24a). For example, it may be determined that the position of the rotation mirror 13 needs to be adjusted if the adjustment amount of the position of the iris camera 12 exceeds a predetermined adjustment threshold. For example, when the position of the eyes of the target person P (e.g., height) is changed by a predetermined amount or more, it may be determined that it is necessary to adjust the position of the rotation mirror 13.

Thus, in the third example embodiment, the position of at least one of the iris camera 12 and the rotation mirror 13 is adjustable. Therefore, the iris camera 12 can more appropriately image the eyes of the target person P via the rotation mirror 13.

(4) Fourth Example Embodiment

Subsequently, a description will be given of a fourth example embodiment of the authentication system and the imaging apparatus. The following describes an authentication system SYSb in which the fourth example embodiment of the authentication system and the imaging apparatus is applied. The authentication system SYSb, as compared with the authentication system SYS described above, differs in that the authentication system SYSb comprises an imaging unit 1b instead of the imaging unit 1. The other features of the authentication system SYSb may be identical to the other features of the authentication system SYS. The imaging unit 1b, as compared with the imaging units described above, differs in that the imaging unit 1b comprises a stopper 141b for limiting the rotation of the rotation mirror 13. The stopper 141b is a specific example of a "rotation limiting unit" in the supplementary notes to be described later. The other features of the imaging unit 1b may be identical to the other features of the imaging unit 1.

Figure 23A:
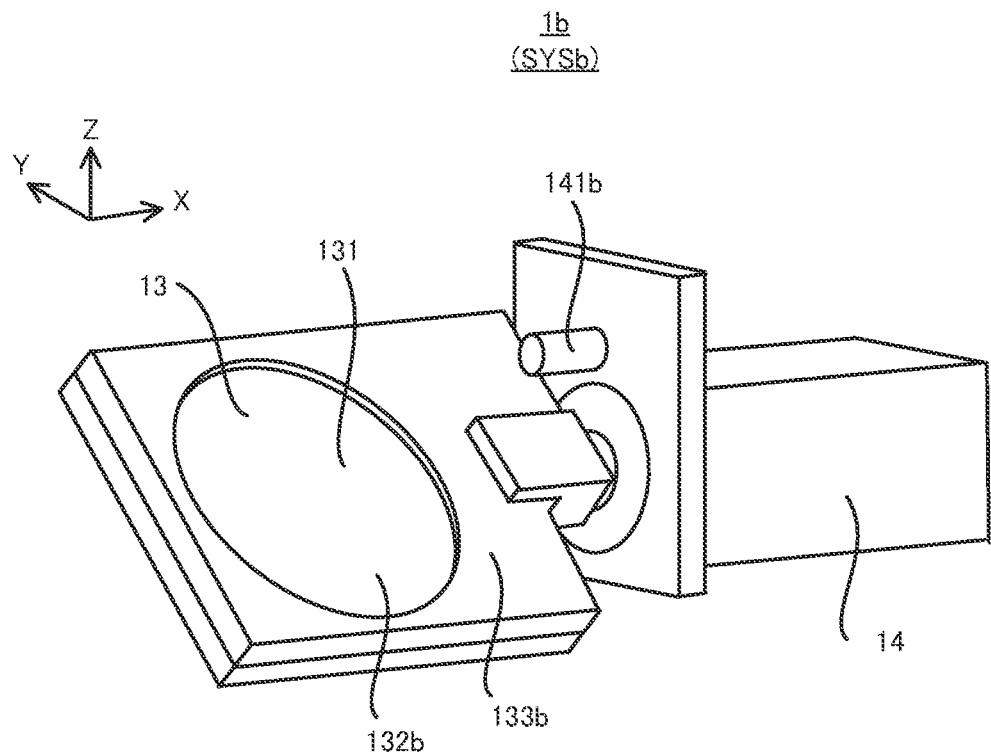
FIG. 23A is a perspective view showing a stopper and a rotation mirror in the fourth example embodiment.

Hereinafter, with reference to FIG. 23A and FIG. 23B, a description will be given of the stopper 141b in the fourth example embodiment. FIG. 23A is a perspective view showing the stopper 141b and the rotation mirror 13, FIG. 23B is a side view showing the stopper 141b and the rotation mirror 13.

Figure 23B:
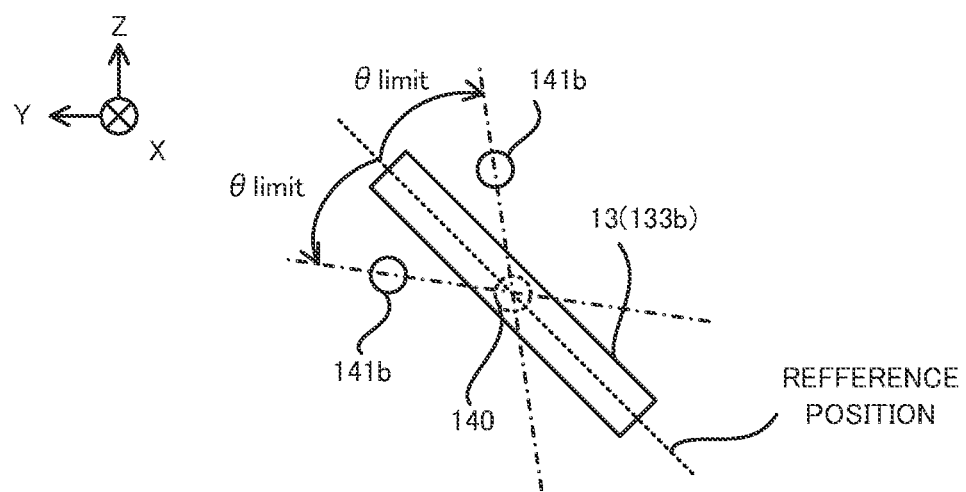
FIG. 23B is a side view showing the stopper and the rotation mirror in the fourth example embodiment.

As shown in FIG. 23A and FIG. 23B, the stopper 141b could contact with the rotation mirror 13 to physically limit the rotation of the rotation mirror 13. Specifically, the stopper 141b is disposed so as to protrude in an area where the rotation mirror 13 goes through when the rotation mirror 13 rotates. The stopper 141b is disposed in a position contactable to the rotation mirror 13 when the rotation mirror 13 is rotated by the allowable upper limit angle $\theta_{limit}$ from the reference position. As a result of that, it is possible that the stopper 141b prevents the rotation mirror 13 from rotating more than the allowable upper limit angle $\theta_{limit}$.

The rotating mirror 13 may be rotatable in clockwise and counterclockwise. In this case, as shown in FIG. 23B, there may be disposed, the stopper 141b capable of limiting the clockwise rotation of the rotation mirror 13, and the stopper 141b capable of limiting the counterclockwise rotation of the rotation mirror 13.

When the stopper 141b makes contact with the reflective surface 131 of the rotation mirror 13 (specifically, the mirror body 132b comprising the reflective surface 131), depending on the magnitude that the stopper 141b has made contact with the rotation mirror 13, the mirror body 132b could be damaged. Therefore, the stopper 141b may contact a mirror holder 133b for holding the mirror body 132b, instead of the mirror body 132b itself, to limit the rotation of the rotation mirror 13.

Figure 24:
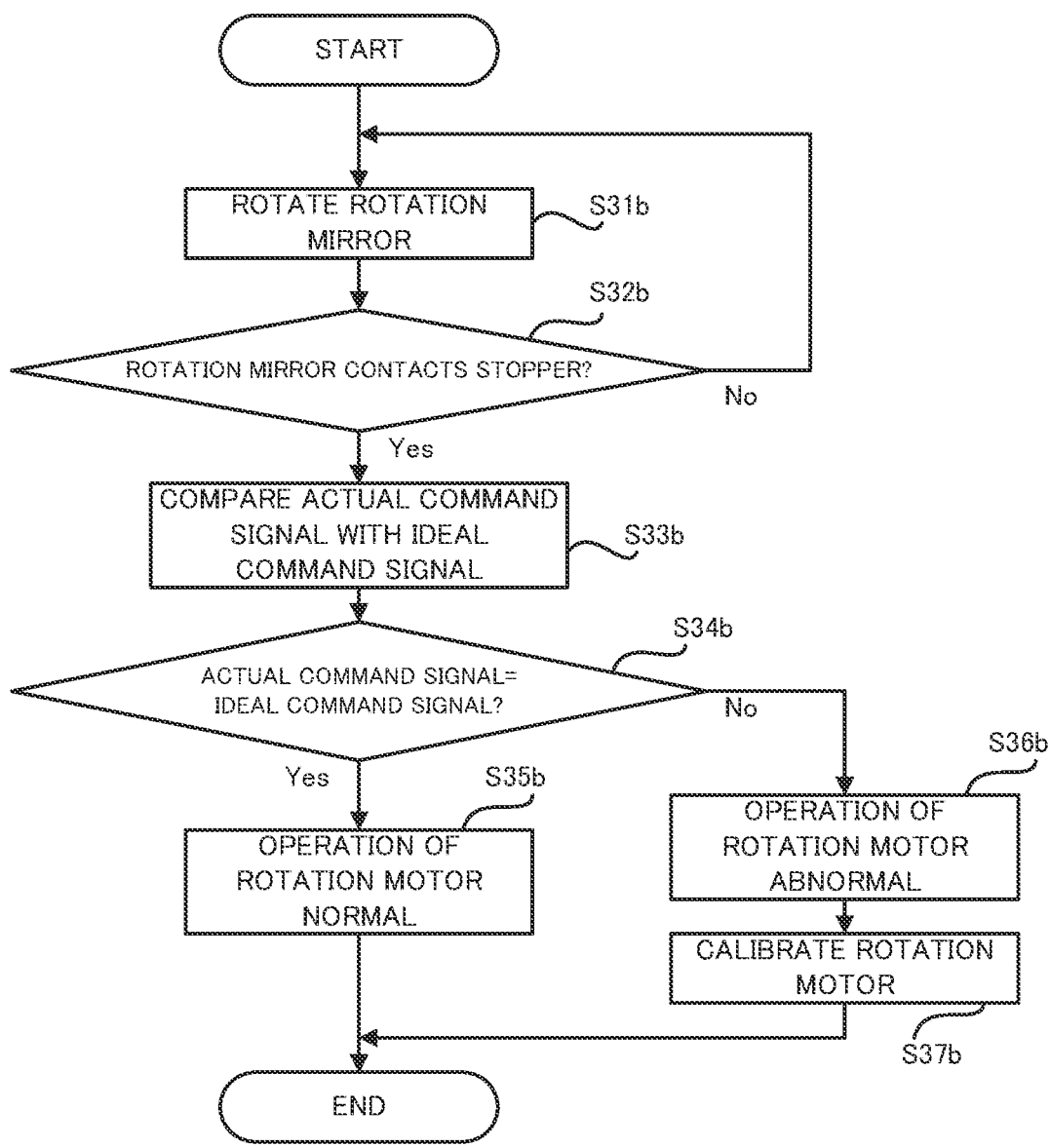
FIG. 24 is a flowchart showing a flow of operation to calibrate the rotation motor using the stopper.

The control unit 2 (in particular, the mirror control unit 212), using the stopper 141b, may calibrate the rotation motor 14. That is, the control unit 2 (in particular, the mirror control unit 212), using the stopper 141b, may perform calibration of the rotation motor 14. Hereinafter, with reference to FIG. 24, the operation for performing the calibration of the rotation motor 14 with the stopper 141b will be described. FIG. 24 is a flowchart showing a flow of the operation for the calibration of the rotation motor 14 using the stopper 141b. The operation shown in FIG. 24 may be performed in parallel with, before, or after the operation shown in FIG. 12.

As shown in FIG. 24, the mirror control unit 212 may drive the rotation motor 14 so that the rotation mirror 13 is rotated from the reference position until the rotation mirror 13 contacts the stopper 141b (step S31b). Thereafter, if the rotation mirror 13 is determined to have contacted the stopper 141b (step S32b: Yes), the mirror control unit 212 compares an actual command signal with an ideal command signal, the actual command signal being used for controlling the rotation motor 14 so that the rotation mirror 13 rotates from the reference position until the rotation mirror 13 contacts the stopper 141b, the ideal command signal for controlling the rotation motor 14 so that the rotation mirror 13 rotates by the allowable upper limit angle $\theta_{limit}$ from the reference position (step S33b). If the actual command signal and the ideal command signal coincide with each other (step S34b: Yes), the mirror control unit 212 estimates that the operation of the rotation motor 14 is normal (step S35b). Because, under the situation where the rotation mirror 13, when the ideal command signal is input to the rotation motor 14, should rotate by the allowable upper limit angle $\theta_{limit}$, the rotation mirror 13 actually rotates by the allowable upper limit angle $\theta_{limit}$ when the actual command signal same as the ideal command signal is input to the rotation motor 14. On the other hand, if the actual command signal and the ideal command signal does not coincide with each other (step S34b: No), the mirror control unit 212 estimates that the operation of the rotation motor 14 is abnormal (step S36b). Because, despite the situation where the rotation mirror 13, when the ideal command signal is input to the rotation motor 14, should rotate by the allowable upper limit angle $\theta_{limit}$, the rotation mirror 13 actually rotates by the allowable upper limit angle $\theta_{limit}$ when the actual command signal different from the ideal command signal is input to the rotation motor 14. Therefore, the mirror control unit 212 may calibrate the rotation motor 14 based on a difference between the actual command signal and the ideal command signal, so that the rotation motor 14 operates normally (step S37b). As a result of that, as compared with the case where the rotation motor 14 is not calibrated, the rotation accuracy of the rotation mirror 13 is improved.

The authentication system SYSa in the third example embodiment described above may employ components specific to the fourth example embodiment. The components specific to the fourth example embodiment may include components with respect to the stopper 141b.

(5) Fifth Example Embodiment

Figure 25:
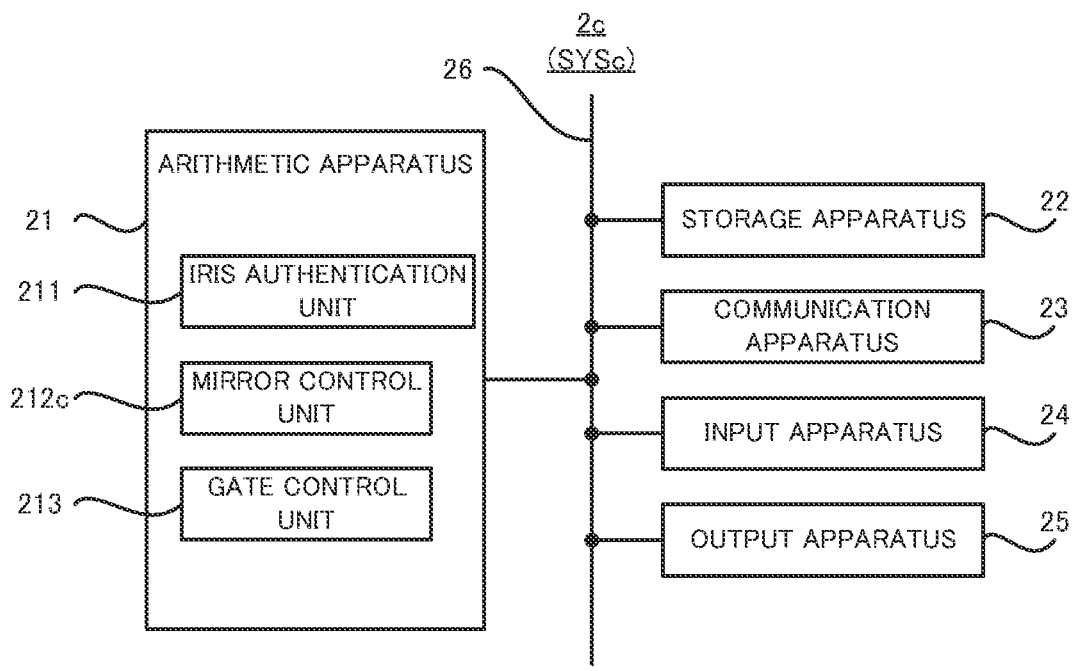
FIG. 25 is a block diagram showing a configuration of a control unit in the fifth example embodiment.

Subsequently, a fifth example embodiment of the authentication system and the imaging apparatus will be described. The following describes an authentication system SYSc to which the fifth example embodiment of the authentication system and the imaging apparatus is applied. The authentication system SYSc, as compared with the authentication system SYS described above, differs in that the authentication system SYSc comprises a control unit 2c instead of the control unit 2. The other features of the authentication system SYSc may be identical to the other features of the authentication system SYS. Hereinafter, with reference to FIG. 25, the control unit 2c in the fifth example embodiment will be described. FIG. 25 is a block diagram showing a configuration of the control unit 2c in the fifth example embodiment.

As shown in FIG. 25, the control unit 2c differs from the control unit 2 described above in that the control unit 2c comprises a mirror control unit 212c instead of the mirror control unit 212. The other features of the control unit 2c may be identical to the other features of the control unit 2.

The mirror control unit 212c differs from the mirror control unit 212 described above in that the mirror control unit 212c is capable of controlling the deceleration of the rotation mirror 13 when the rotation mirror 13 stops based on the state of the iris of the target person P captured in the iris image IMG_I. The other features of the mirror control unit 212c may be the same as the other features of the mirror control unit 212.

Depending on the deceleration when the rotation mirror 13 is stopped, the rotation mirror 13 could vibrate in reaction under a situation where the rotation motor 14 is not applying a force to the rotation mirror 13. The possibility that the vibration of the rotation mirror 13 caused by such reaction occurs is higher as the deceleration when the rotation mirror 13 stops increases. In this case, there is a possibility that the iris camera 12 captures the image of the eyes of the target person P under a situation where the rotation mirror 13 is vibrating. As a result of that, the state of the iris captured in the iris image IMG_I may not be good. For example, the iris may be blurred or shaken in the iris image IMG_I. As a result of that, there is a possibility that the accuracy of authentication by the iris authentication unit 211 deteriorates.

Therefore, when the state of the iris captured in the iris image IMG_I is not good, the mirror control unit 212 estimates that the rotation mirror 13 is vibrating due to the reaction when the rotation mirror 13 stops, and controls the deceleration when the rotation mirror 13 stops so as to suppress the vibration of the rotation mirror 13 caused by the reaction.

Figure 26:
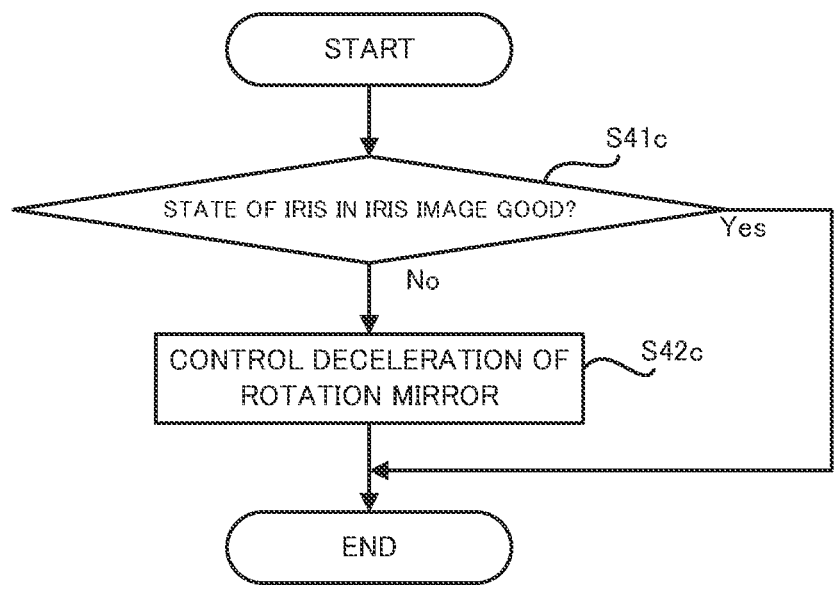
FIG. 26 is a flowchart showing a flow of operation to control the deceleration when the rotation mirror stops.

Specifically, the mirror control unit 212 may perform, in accordance with a flowchart shown in FIG. 26, operation of controlling the deceleration when the rotation mirror 13 stops. The operation shown in FIG. 26 may be performed in parallel with, before, or after the operation shown in FIG. 12. Alternatively, the operation shown in FIG. 26 may be performed each time the iris camera 12 captures the image of the iris of the target person P in step S108 in FIG. 12 (i.e., each time the iris image IMG_I is generated).

Specifically, as shown in FIG. 26, the mirror control unit 212 determines whether or not the state of the iris captured in the iris image IMG_I is good (step S41c). When it is determined that the state of the iris reflected in the iris image IMG_I is not good (Step S41c: No), the mirror control unit 212 estimates that the rotation mirror 13 is vibrating due to the reaction when the rotation mirror 13 stops, and controls the deceleration when the rotation mirror 13 stops so that the vibration of the rotation mirror 13 caused by the reaction is suppressed (Step S42c). An example of the deceleration control will be described below.

Figure 27:
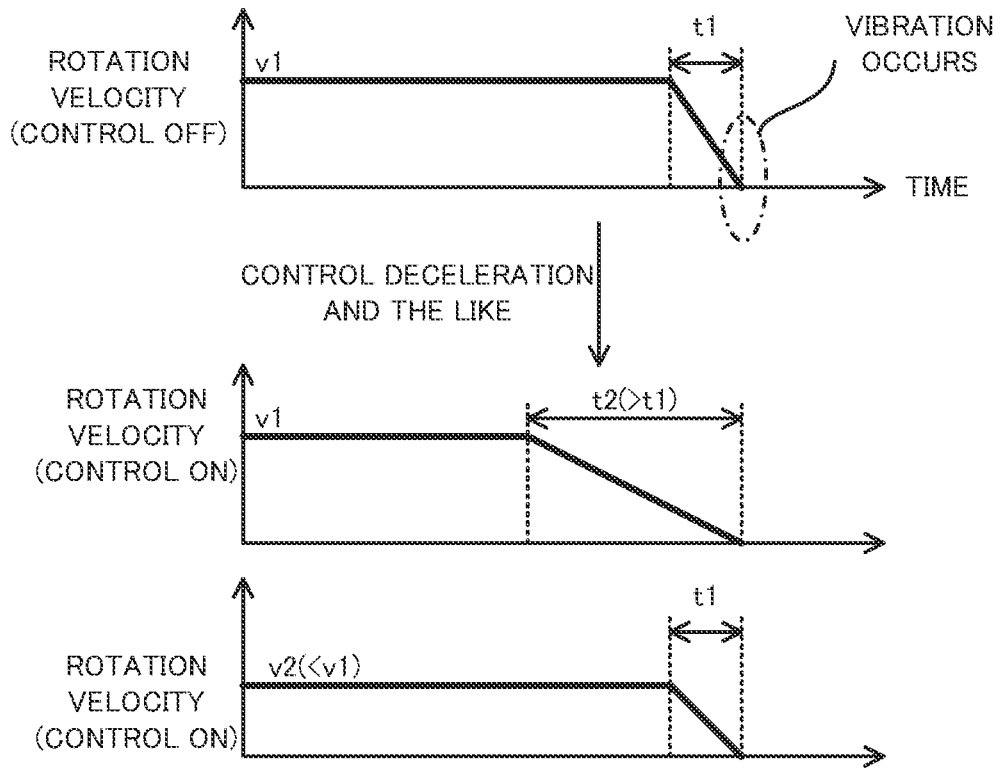
FIG. 27 is a graph showing the rotational velocity of the rotation mirror in the fifth example embodiment.

For example, there will be described an example that, as shown in a graph at the first stage of FIG. 27, when the rotation mirror 13 rotating at a rotation velocity v1 is made to stop with spending time t1, the iris captured in the iris image IMG_I is not in good condition. In this case, the mirror control unit 212, as shown in a graph of the second stage in FIG. 27, may control the rotation motor 14 so that the rotation mirror 13 stops with spending time t2 longer than the time t1. That is, the mirror control unit 212 may control the rotation motor 14 so that it becomes to take longer to decelerate the rotation mirror 13 for stopping the rotation mirror 13. Alternatively, the mirror control unit 212, in addition to or in place of controlling the rotation motor 14 so that it becomes to take longer to decelerate the rotation mirror 13, may control the rotation motor 14 as shown in a graph of the third stage of FIG. 27, so that the rotation mirror 13 rotating at a rotation velocity v2 is made to stop, the rotation velocity v2 being slower than the rotation velocity v1. That is, the mirror control unit 212 may control the rotation motor 14 so that the upper limit of the rotation velocity of the rotation mirror 13 is reduced. In either case, since the deceleration of the rotation mirror 13 when the rotation mirror 13 stops is reduced, the possibility that the rotation mirror 13 vibrate caused by the reaction is reduced.

Alternatively, a predetermined filter (e.g., a low-pass filter or a moving-average filter available as a velocity filter) may be available to control the responsiveness of the rotating motor 14. In this case, the mirror control unit 212 may control the rotation motor 14 by adjusting the time constant of the filter, in addition to or in place of controlling the rotation motor 14 so that it becomes to take longer to decelerate the rotation mirror 13 and/or the upper limit of the rotation velocity of the rotation mirror 13 is reduced. For example, the mirror control unit 212, by adjusting the time constant of the filter, may control the deceleration of the rotation mirror 13 so that the vibration of the rotation mirror 13 caused by the reaction is reduced or eliminated.

Thus, when the state of the iris captured in the iris image IMG_I is not good, the control unit 2 in the fifth example embodiment is capable of controlling the deceleration at the moment when the rotation mirror 13 stops so as to suppress (for example, to reduce or eliminate) the vibration of the rotation mirror 13 caused by the reaction. As a result of that, as compared with a case that the deceleration of the rotation mirror 13 is not controlled, made higher could be a possibility that the state of the iris captured in the iris image IMG_I is good. For example, made higher could be a possibility that an iris (e.g., a clear, not-shaken or unblurred iris) capable of properly acquiring iris patterns is captured in the iris image IMG_I. Therefore, as compared with the case that the deceleration of the rotation mirror 13 is not controlled, the iris authentication unit 211 can more accurately authenticate the target person P using the iris image IMG_I.

Figure 28:
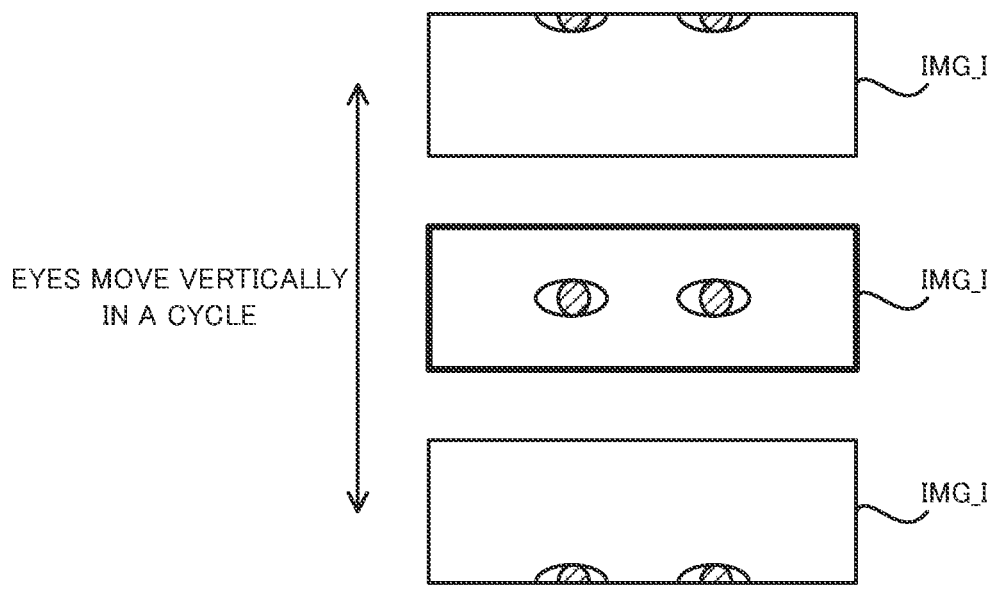
FIG. 28 shows a plurality of iris images generated when the rotation mirror is vibrating.

In consideration of the fact that the vibration of the rotation mirror 13 caused by the reaction is likely to be cyclic vibration, a plurality of iris images IMG_I generated by the iris camera 12 capturing the eyes of the target person P a plurality of times respectively during the period when the rotation mirror 13 is vibrating, could be, as shown in FIG. 28, a plurality of iris images IMG_I where the eyes of the target person P moves in a cycle along a direction corresponding to the direction of the vibration of the rotation mirror 13 (for example, in the vertical direction as shown in FIG. 28). In this case, in step S109 in FIG. 12, the iris authentication unit 211 may select from the plurality of iris images IMG_I, at least one iris image IMG_I where the iris is captured in a desired position, and may authenticate the target person P using the selected at least one iris image IMG_I. For example, an iris captured in an intermediate position (e.g., the intermediate position in the vertical direction) of the iris image IMG_I is, as compared with an iris captured in the upper or lower edge position of the iris image IMG_I, likely to be in a less shaken or less blurred state. In this case, the iris authentication unit 211 may select from the two of more iris images IMG_I, at least one iris image IMG_I where an iris is captured in the intermediate position (for example, the intermediate position in the vertical direction), and may authenticate the target person P using the selected at least one iris image IMG_I. As a result of that, as compared with a case where it is not performed to select the at least one iris image IMG_I by focusing on the possibility that the vibration of the rotation mirror 13 is cyclic, the iris authentication unit 211 can more accurately authenticate the target person P using the iris image IMG_I.

In addition, from the authentication system SYSa in the third example embodiment to the authentication system SYSb in the fourth example embodiment, at least one of them may employ components specific to the fifth example embodiment. The components specific to the fifth example embodiment may include components related to the mirror control unit 212c.

(6) Sixth Example Embodiment

Figure 29:
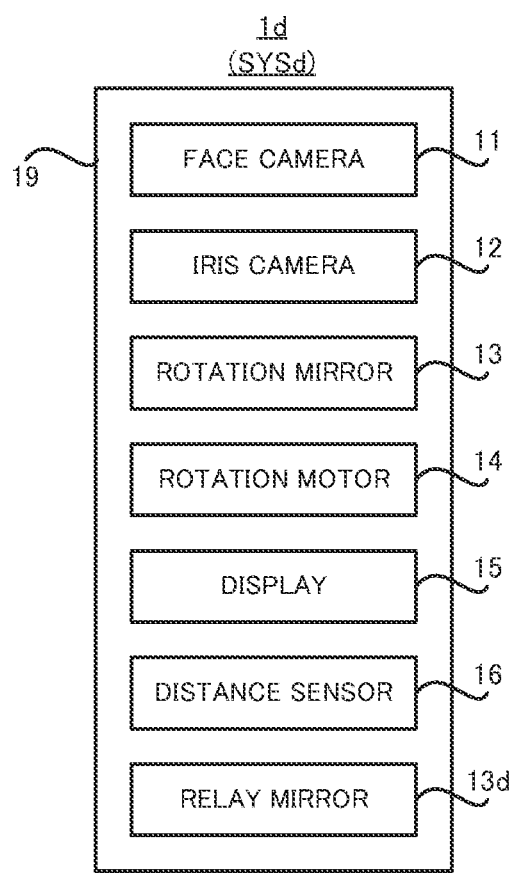
FIG. 29 is a block diagram showing a configuration of an imaging unit in the sixth example embodiment.

Subsequently, a description will be given of a sixth example embodiment of the authentication system and the imaging apparatus. The following describes an authentication system SYSd to which the sixth example embodiment of the authentication system and the imaging apparatus is applied. The authentication system SYSd, as compared with the authentication system SYS described above, differs in that the authentication system SYSd comprises an imaging unit 1d instead of the imaging unit 1. The other features of the authentication system SYSd may be identical to the other features of the authentication system SYS. Hereinafter, with reference to FIG. 29, a description will be given of the imaging unit 1d in the sixth example embodiment. FIG. 29 is a block diagram showing a configuration of the imaging unit 1d in the sixth example embodiment.

As shown in FIG. 29, the imaging unit 1d, as compared with the imaging unit 1 described above, differs in that the imaging unit 1d comprises at least one relay mirror 13d as a specific example of each of the "second reflective unit", the "third reflective unit" and the "fourth reflective unit" in the supplementary notes to be described later. The other features of the imaging unit 1d may be identical to the other features of the imaging unit 1.

The relay mirror 13d is an optical element that reflects light L2 from the iris of the target person P toward the rotation mirror 13. In particular, the relay mirror 13d is an optical element that reflects toward the rotation mirror 13, light L2 from the iris of the target person P which propagates toward the front of the target person P.

Such relay mirror 13d may be disposed so that a plurality of lights L2 each propagating from a plurality of different positions are incident on the same rotation mirror 13. As an example, the imaging unit 1d may comprise: the relay mirror 13d that reflects toward the rotation mirror 13, light L2 from the iris of the target person P positioned at the first position; and the relay mirror 13d that reflects toward the rotation mirror 13, light L2 from the iris of the target person P positioned at the second position different from the first position. As a result of that, the imaging unit 1d can image the eyes of the target person P at various positions using a single iris camera 12.

Figure 30A:
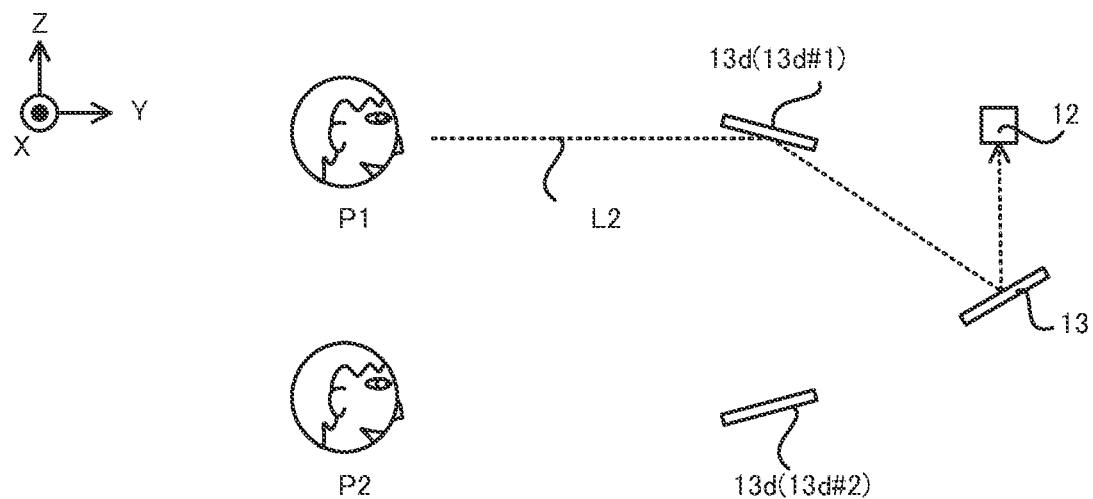
FIG. 30A shows an iris camera that captures the image of a target person via a relay mirror.
Figure 30B:
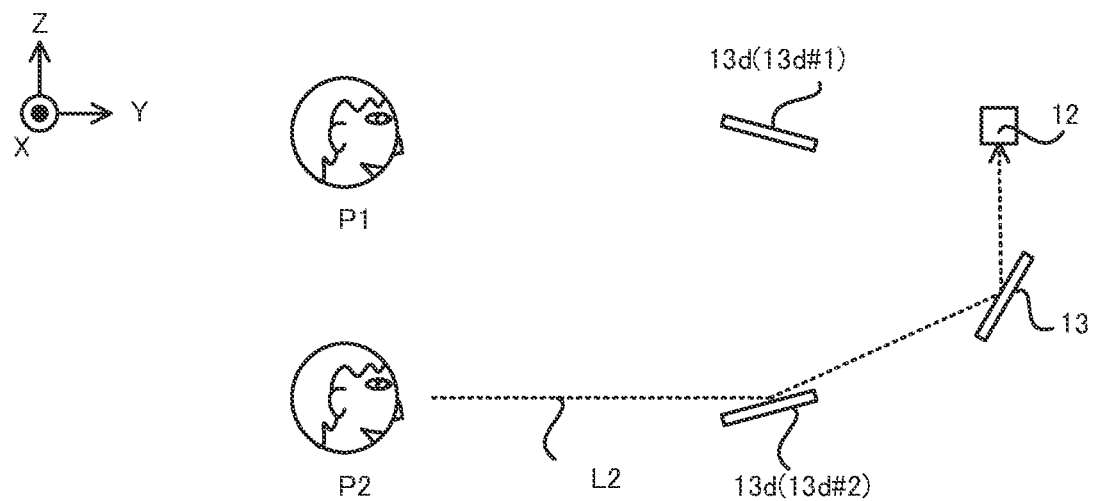
FIG. 30B shows an iris camera that captures the image of a target person via a relay mirror.

As an example, the imaging unit 1d, as shown in FIGS. 30A and 30B, may be provided with a relay mirror 13d #1 and a relay mirror 13d #2. The relay mirror 13d #1 is capable of reflecting toward the rotation mirror 13, light L2 from the iris of the target person P positioned at the first position P1, as shown in FIG. 30A. In this case, the relay mirror 13d #1 may be disposed at a desired position capable of realizing a state that the iris camera 12 captures the image of the eyes of the target person P positioned at the first position P1 substantially from the front of the eyes. For example, the relay mirror 13d #1 may be disposed at a position so as to squarely face the iris of the target person P positioned at the first position P1. As an example, the relay mirror 13d #1 may be disposed at a height same as a height of the iris of the target person P positioned at the first position P1, or at a height whose difference from the height of the iris of the target person P positioned at the first position P1 falls within an allowable range. On the other hand, the relay mirror 13d #2 is capable of reflecting toward the rotation mirror 13, light L2 from the iris of the target person P positioned at the second position P2 different from the first position P1 in the Z-axis direction (that is, in the vertical direction), as shown in FIG. 30B. In this case, the relay mirror 13d #2 may be disposed at a desired position capable of realizing a state the iris camera 12 captures the image of the eyes of the target person P positioned at the second position P2 substantially from the front of the eyes. For example, the relay mirror 13d #2 may be disposed at a position so as to squarely face the iris of the target person P positioned at the second position P2. As an example, the relay mirror 13d #2 may be disposed at a height same as a height of the iris of the target person P positioned at the second position P2, or at a height whose difference from the height of the iris of the target person P positioned at the second position P2 falls within an allowable range.

Figure 31:
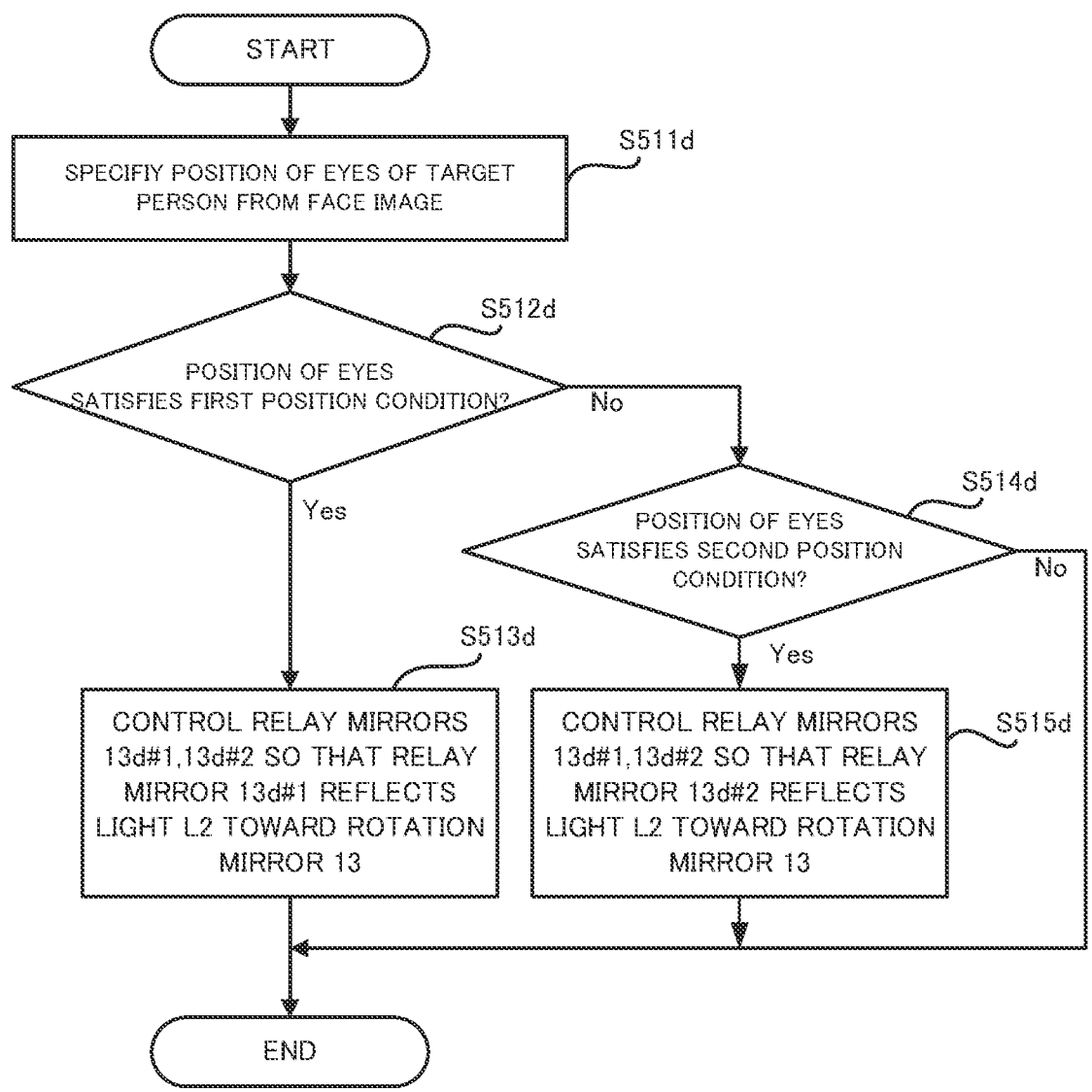
FIG. 31 is a flowchart showing a flow of operation to switch relay mirrors that reflect light from an iris of the target person toward the rotation mirror.

In this case, the mirror control unit 212 may switch the relay mirrors 13d each reflecting light L2 from the iris of the target person P toward the rotation mirror 13 according to a flowchart shown in FIG. 31. FIG. 31 is a flowchart showing a flow of operation of switching the relay mirrors 13d each reflecting light L2 from the iris of the target person P toward the rotation mirror 13. The operation shown in FIG. 31 may be performed before the iris camera 12 captures the image of the iris of the target person P in step S108 of FIG. 12. FIG. 31 shows an example of operation to be performed in a case that the first position P1 is higher than the second position P2 in FIG. 30A and FIG. 30B (i.e., the first position P1 is located at the +Z side further than the second position P2 with respect to the Z-axis direction).

Specifically, as shown in FIG. 31, the mirror control unit 212 specifies the position (in particular, the position in the Z-axis direction or the height) of the eyes of the target person P on the basis of the face image IMG_F (step S511d). The operation of step S511d may be the same as the operation of step S105 in FIG. 12.

Thereafter, the mirror control unit 212, the position of the eyes specified in step S511d determines whether to satisfy a predetermined first position condition (step S512d). The first position condition may include a condition that the eyes are located at the first position P1. The first position condition may include a condition that the position of the eyes (in particular, the height) exceeds a predetermined first height threshold.

As a result of the determination in step S512d, when it is determined that the position of the eyes satisfies the predetermined first position condition (step S512d: Yes), the mirror control unit 212 controls the relay mirror 13d #1 so that the relay mirror 13d #1 capable of reflecting toward the rotation mirror 13 light L2 from the iris of the target person P positioned at the first position P1 higher than the second position P2, reflects the light L2 toward the rotation mirror 13 (step S513d). On the other hand, the mirror control unit 212 may control the relay mirror 13d #2 so that the relay mirror 13d #2 capable of reflecting toward the rotation mirror 13 light L2 from the iris of the target person P positioned at the second position P2 lower than the first position P1, does not reflect the light L2 toward the rotation mirror 13 (step S513d). As a result of that, the state of the imaging unit 1d is the state shown in FIG. 30A.

On the other hand, as a result of the determination in step S512d, when the position of the eyes is determined not to satisfy the predetermined first position condition (step S512d: No), the mirror control unit 212 determines whether the position of the eyes specified in step S511d, the first position condition determines whether to satisfy a predetermined second position condition different from the first position condition (step S514d). The second position condition may include a condition that the eyes are located at the second position P2. The second position condition may include a condition that the position (in particular, the height) of the eyes is lower than a predetermined second height threshold (the second height threshold is equal to or less than the first height threshold).

As a result of the determination in step S514d, when it is determined that the position of the eyes satisfies the predetermined second position condition (step S514d: Yes), the mirror control unit 212 controls the relay mirror 13d #2 so that the relay mirror 13d #2 capable of reflecting toward the rotation mirror 13 light L2 from the iris of the target person P located at the second position P2 lower than the first position P1, reflects the light L2 toward the rotation mirror 13 (step S515d). On the other hand, the mirror control unit 212 may control the relay mirror 13d #1 so that the relay mirror 13 #1 capable of reflecting toward the rotation mirror 13 light L2 from the iris of the target person P located at the first position P1 higher than the second position P2, does not reflect the light L2 toward the rotation mirror 13 (step S515d). As a result, the state of the imaging unit 1d is the state shown in FIG. 30B.

As a result of that, the imaging unit 1d is capable of imaging the eyes of the target person P at various positions (typically with respect to the height) using a single iris camera 12. In particular, increased could be a chance of imaging the eyes of the subject P at various locations (typically with respect to the height) from the front of the eyes using a single iris camera 12. As a result of that, increased could be a chance of generating the iris image IMG_I in which the iris is captured in a state the eyes of the target person P have been imaged from the front of the target person P. Here, the accuracy of the authentication using the iris image IMG_I generated by capturing the image of the eyes of the target person P diagonally above or below tends to be worse than that of the authentication using the iris image IMG_I generated by capturing the image of the eyes of the target person P from the front. This is because in the iris image IMG_I generated by capturing the image of the eyes of the target person P from diagonally above or below, compared to the iris image IMG_I generated by capturing the image of the eyes of the target person P from the front, the iris is likely to be hidden by at least one of eyelashes and eyelids, etc. Consequently, in the examples shown in FIGS. 30A and 30B, even when the height of the eyes of the target person P changes, the authentication system SYSd can authenticate the target person P with high accuracy.

Figure 32A:
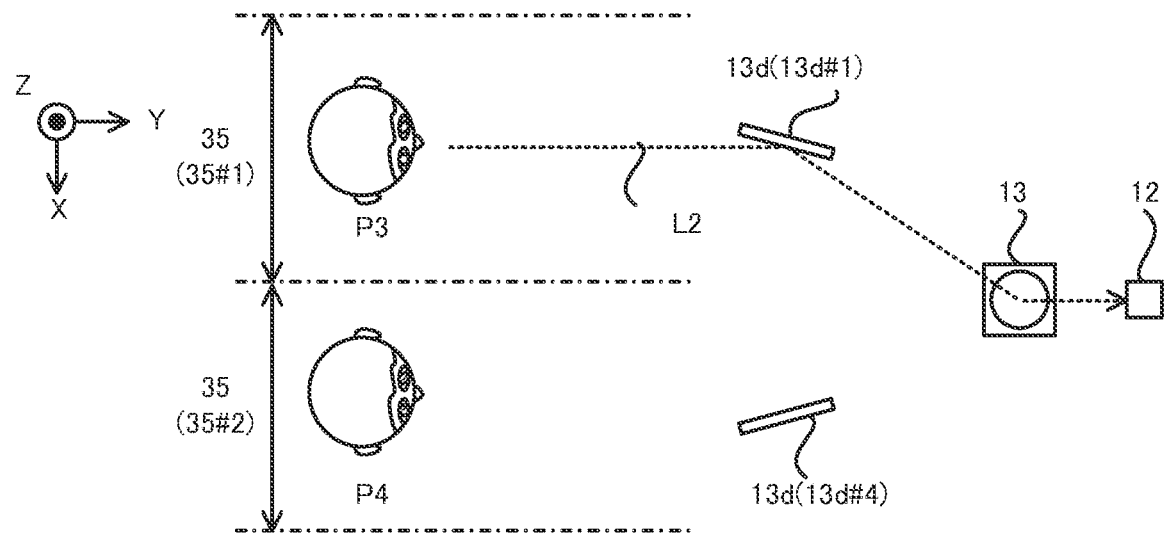
FIG. 32A shows the iris camera that captures the image of the target person via the relay mirror.
Figure 32B:
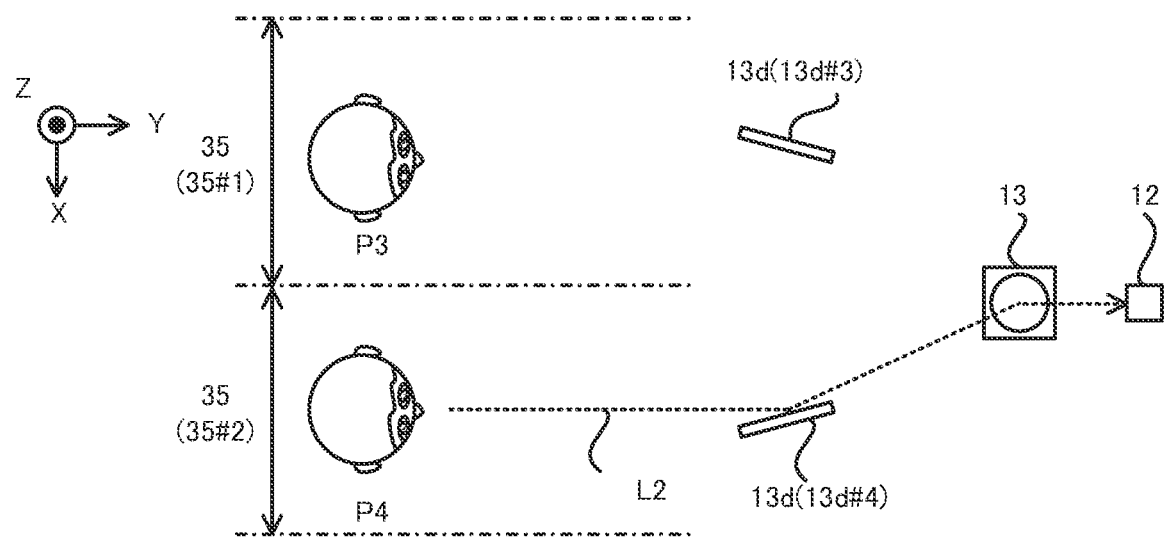
FIG. 32B shows the iris camera that captures the image of the target person via the relay mirror.

As another example, the imaging unit 1d, as shown in FIGS. 32A and 32B, may be provided with a relay mirror 13d #3 and a relay mirror 13d #4. The relay mirror 13d #3 is capable of reflecting toward the rotation mirror 13 light L2 from the iris of the target person P positioned at the third position P3 as shown in FIG. 32A. On the other hand, the relay mirror 13d #4 is, as shown in FIG. 32B, capable of reflecting toward the rotation mirror 13 light L2 from the iris of the target person P located at the fourth position P4 different from the third position P3 in the horizontal direction (e.g., at least one of the X-axis direction and the Y-axis direction).

The third position P3 and the fourth position P4 may be included in the two different lanes 35 respectively. For example, as shown in FIG. 32A and FIG. 32B, the third position P3 is included in the first lane 35 #1, and the fourth position P4 may be included in the second lane 35 #2 adjacent to the first lane 35 #1. As a result of that, the imaging unit 1d is capable of imaging with a single iris camera 12, the eyes of the target person P going through the first lane 35 #1 and also the eyes of the target person P going through the second lane 35 #2. Therefore, it is not necessary to prepare both imaging units 1, one imaging the eyes of the target person P going through the first lane 35 #1 and the other one imaging the eyes of the target person P going through the second lane 35 #2. Therefore, it is possible to simplify the configuration of the authentication system SYSd, and to reduce the cost of the authentication system SYSd.

Figure 33:
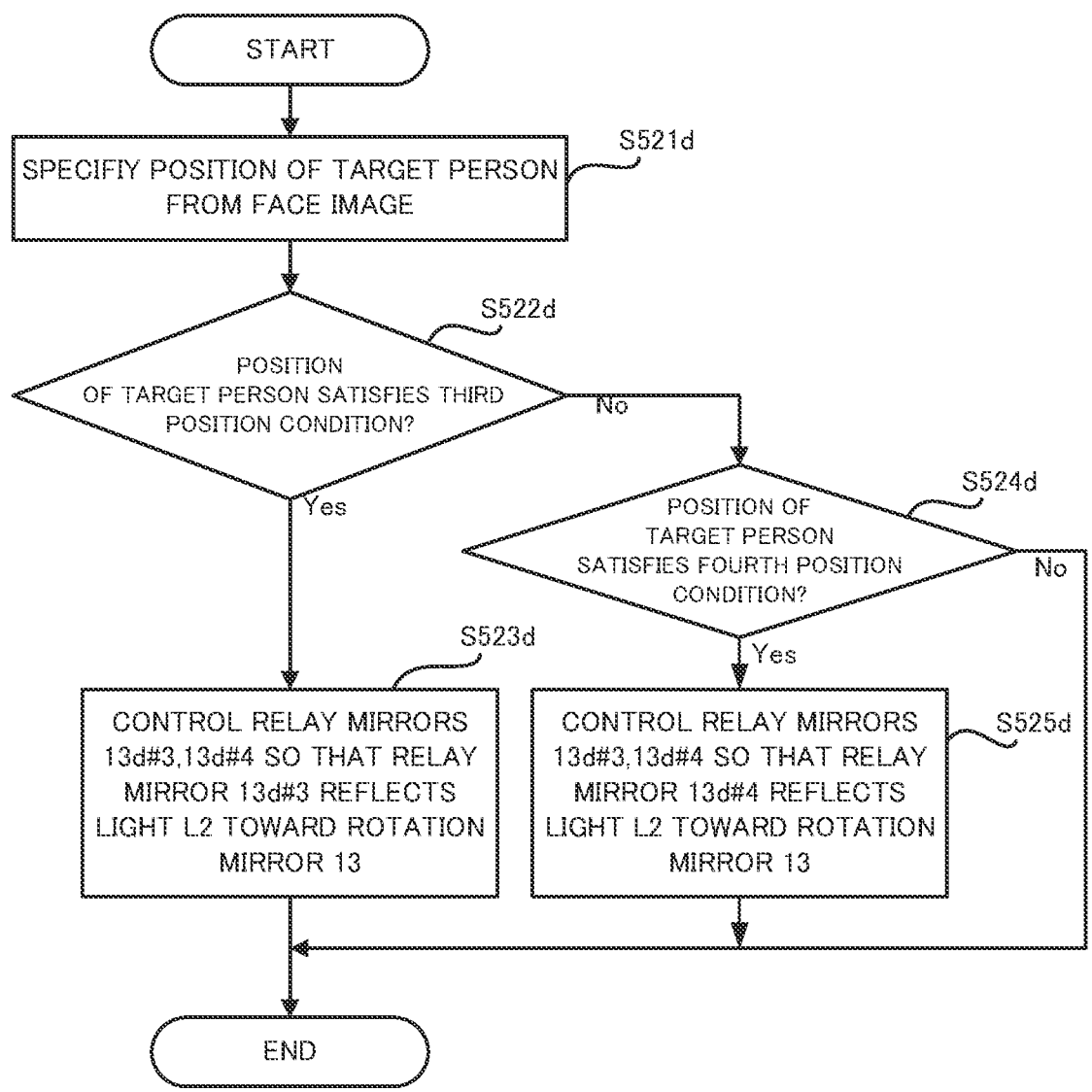
FIG. 33 is a flowchart showing a flow of operation to switch the relay mirrors that reflect light from the iris of the target person toward the rotation mirror.

In this case, the mirror control unit 212 may switch the relay mirrors 13d that reflects light L2 from the iris of the target person P toward the rotation mirror 13 according to a flowchart shown in FIG. 33. FIG. 33 is the flowchart showing a flow of operation of switching the relay mirrors 13d that reflects light L2 from the iris of the target person P toward the rotation mirror 13. The operation shown in FIG. 33 may be performed before the iris camera 12 captures the image of the iris of the target person P in step S108 in FIG. 12.

Specifically, as shown in FIG. 33, the mirror control unit 212 specifies the position (in particular, the position in the horizontal direction) of the target person P on the basis of the face image IMG_F (step S521d).

Thereafter, the mirror control unit 212 determines whether the position of the target person P specified in step S521d satisfies a predetermined third position condition (step S522d). The third position condition may include a condition that the target person P is positioned at the third position P3. The third position condition may include a condition that the target person P is located in the first lane 35 #1.

As a result of the determination in step S522d, when it is determined that the position of the target person P satisfies the predetermined third position condition (Step S522d: Yes), the mirror control unit 212 controls the relay mirror 13d #3 so that the relay mirror 13d #3 capable of reflecting toward the rotation mirror 13 light L2 from the iris of the target person P positioned at the third position P3, reflects the light L2 toward the rotation mirror 13 (Step S523d). On the other hand, the mirror control unit 212 may control the relay mirror 13d #4 so that the relay mirror 13d #4 capable of reflecting toward the rotation mirror 13 light L2 from the iris of the target person P located at the fourth position P4, does not reflect the light L2 toward the rotation mirror 13 (step S523d). As a result of that, the state of the imaging unit 1d is the state shown in FIG. 32A.

On the other hand, as a result of the determination in step S522d, when it is determined that the position of the target person P does not satisfy the predetermined third position condition (step S522d: No), the mirror control unit 212 determines whether or not the position of the target person P specified in step S521d satisfies a predetermined fourth position condition different from the third position condition (step S524d). The fourth position condition may include a condition that the target person P is positioned at the fourth position P4. The fourth position condition may include a condition that the target person P is located in the second lane 35 #2.

As a result of the determination in step S524d, when it is determined that the position of the target person P satisfies the predetermined fourth position condition (Step S524d: Yes), the mirror control unit 212 controls the relay mirror 13d #4 so that the relay mirror 13d #4 capable of reflecting toward the rotation mirror 13 light L2 from the iris of the target person P positioned at the fourth position P4, reflects the light L2 toward the rotation mirror 13 (Step S525d). On the other hand, the mirror control unit 212 may control the relay mirror 13d #3 so that the relay mirror 13d #3 capable of reflecting toward the rotation mirror 13 light L2 from the iris of the target person P located at the third position P3, does not reflect the light L2 toward the rotation mirror 13 (step S525d). As a result of that, the state of the imaging unit 1d is the state shown in FIG. 32B.

Figure 34A:
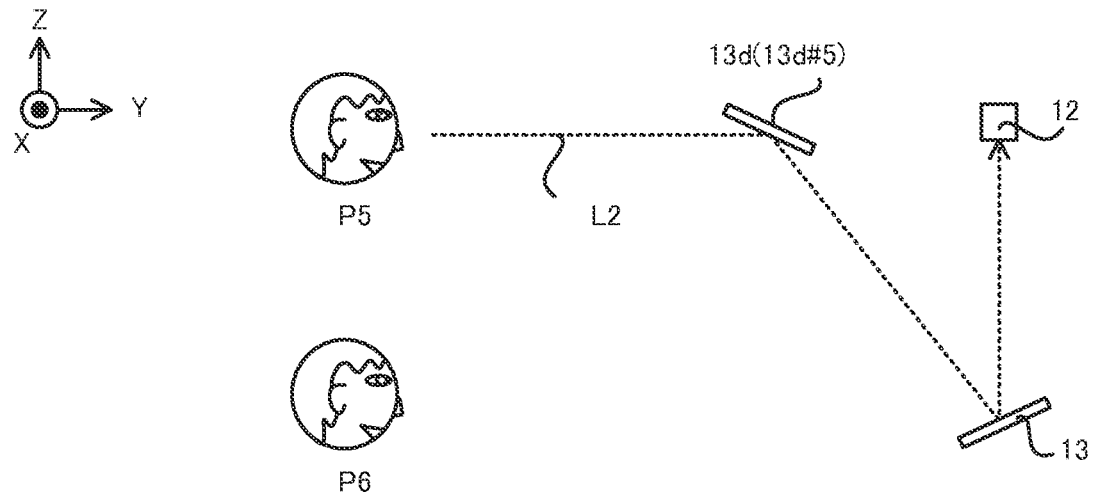
FIG. 34A shows the iris camera for imaging the target person via the relay mirror.
Figure 34B:
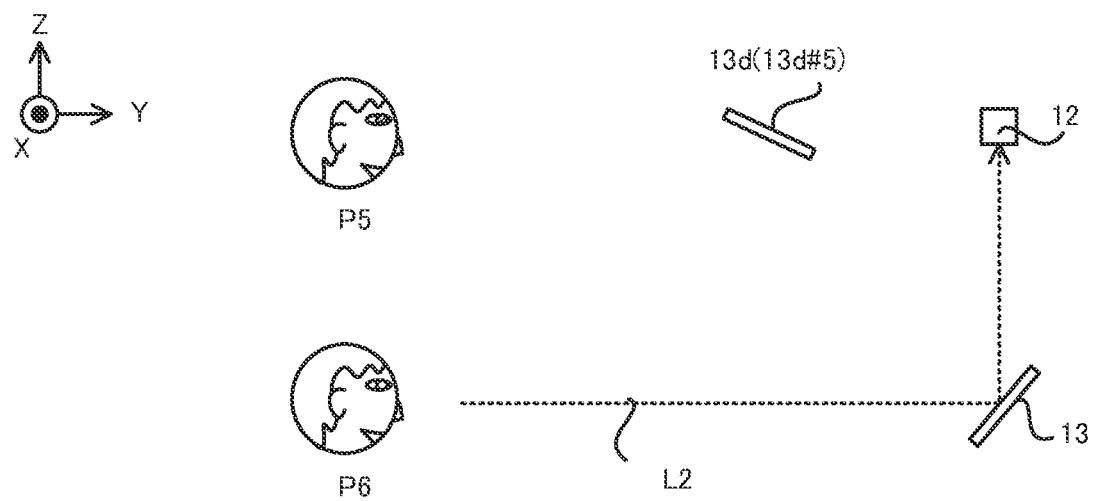
FIG. 34B shows the iris camera for imaging the target person via the relay mirror.
Figure 35A:
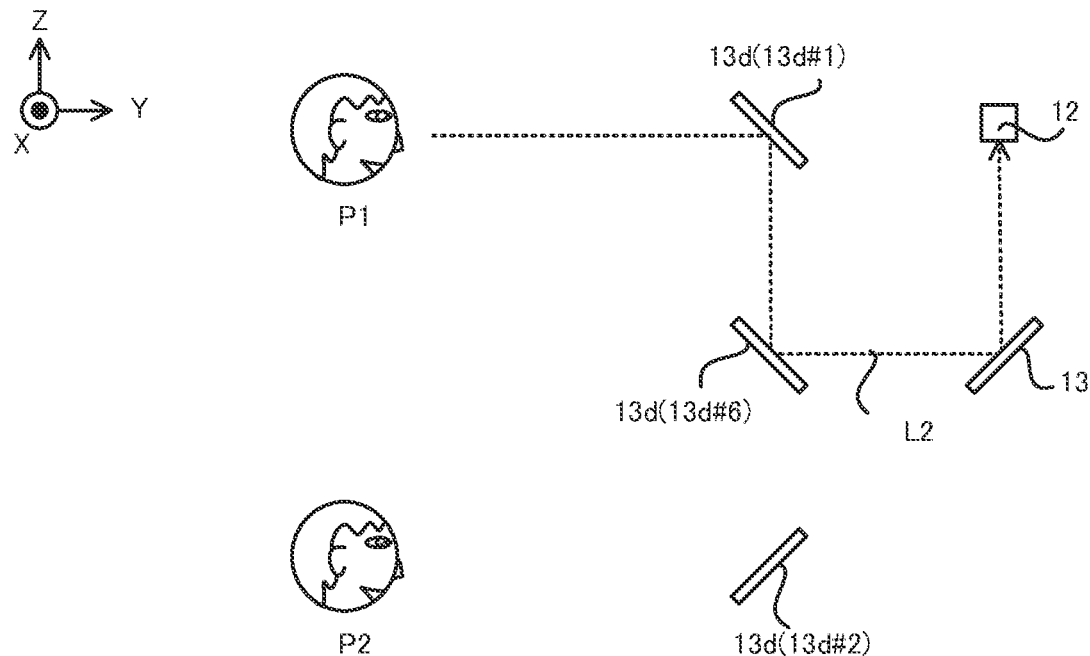
FIG. 35A shows the iris camera that captures the image of the target person via the relay mirror.
Figure 35B:
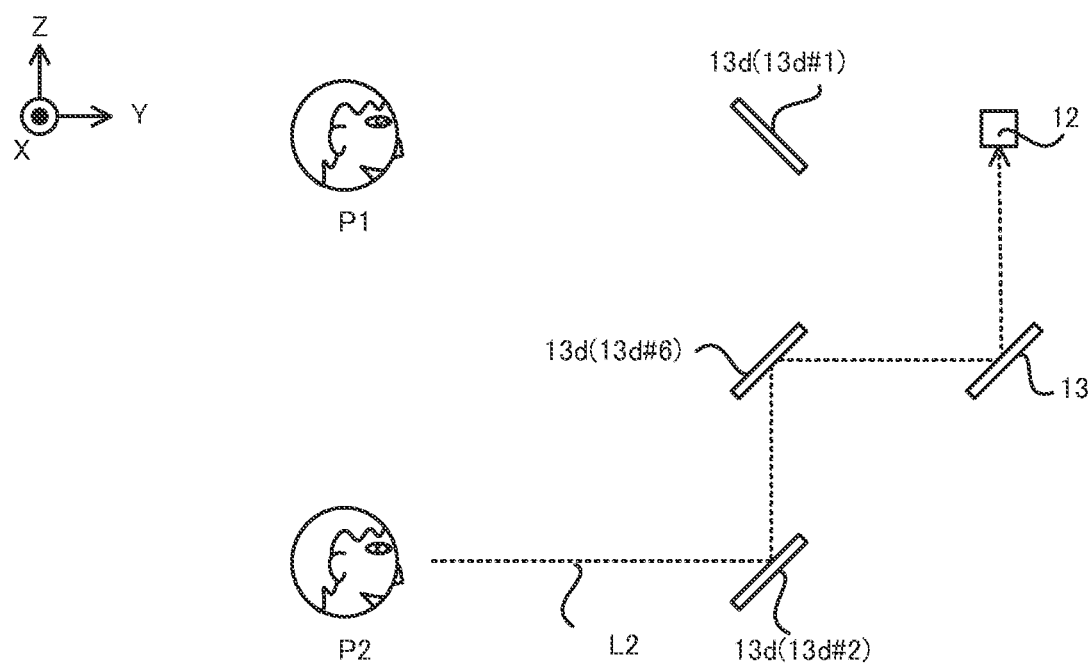
FIG. 35B shows the iris camera that captures the image of the target person via the relay mirror.

FIGS. 30A and 30B and FIGS. 32A and 32B show an example of the imaging unit 1d comprising two relay mirrors 13d. However, the imaging unit 1d may comprise a single relay mirror 13d or may comprise three or more relay mirrors 13d. For example, as shown in FIGS. 34A and 34B, the imaging unit 1d may include a relay mirror 13d #5 that reflects toward the rotation mirror 13 light L2 from the iris of the target person P positioned at the fifth position P5. In this case, the light L2 from the iris of the target person P positioned at the sixth position P6 different from the fifth position P5 may be incident on the rotation mirror 13 without the relay mirror 13d. For example, as shown in FIG. 35A and FIG. 35B, the imaging unit 1d may be provided with a relay mirror 13 #6 that reflects the light L2 from the relay mirror 13d #1 shown in FIG. 30A toward the rotation mirror 13 and also reflects the light L2 from the relay mirror 13d #2 shown in FIG. 30B toward the rotation mirror 13. Thus, since the number of relay mirrors 13d is not limited, the degree of freedom in design with respect to the relay mirror 13d is relatively high.

From the authentication system SYSa in the third example embodiment to the authentication system SYSc in the fifth example embodiment described above, at least one of them may employ components specific to the sixth example embodiment. The components specific to the sixth example embodiment may include components related to the relay mirror 13d.

(7) Seventh Example Embodiment

Figure 36:
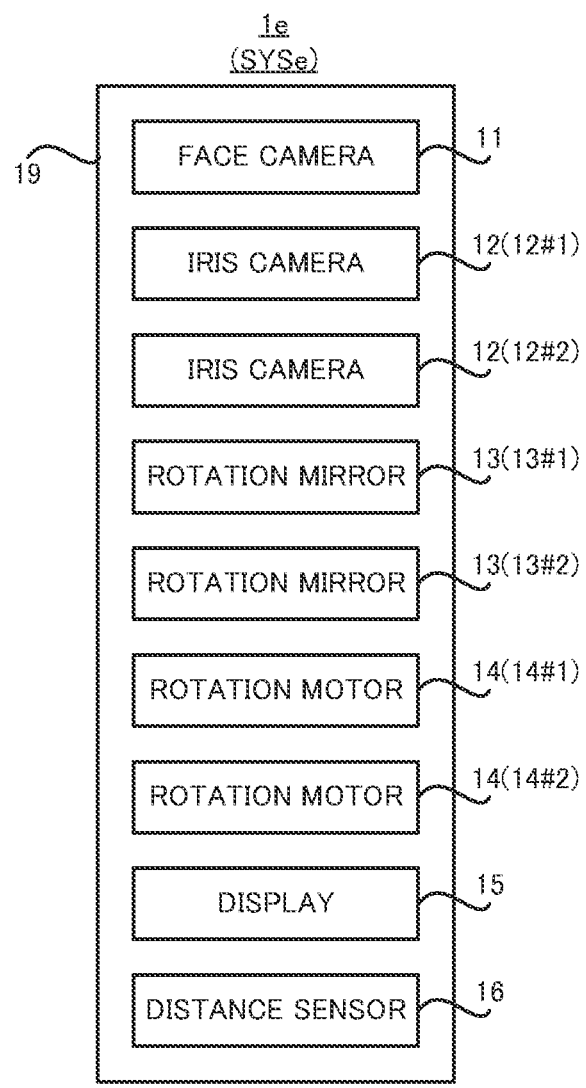
FIG. 36 is a block diagram showing a configuration of an imaging unit in the seventh example embodiment.
Figure 37:
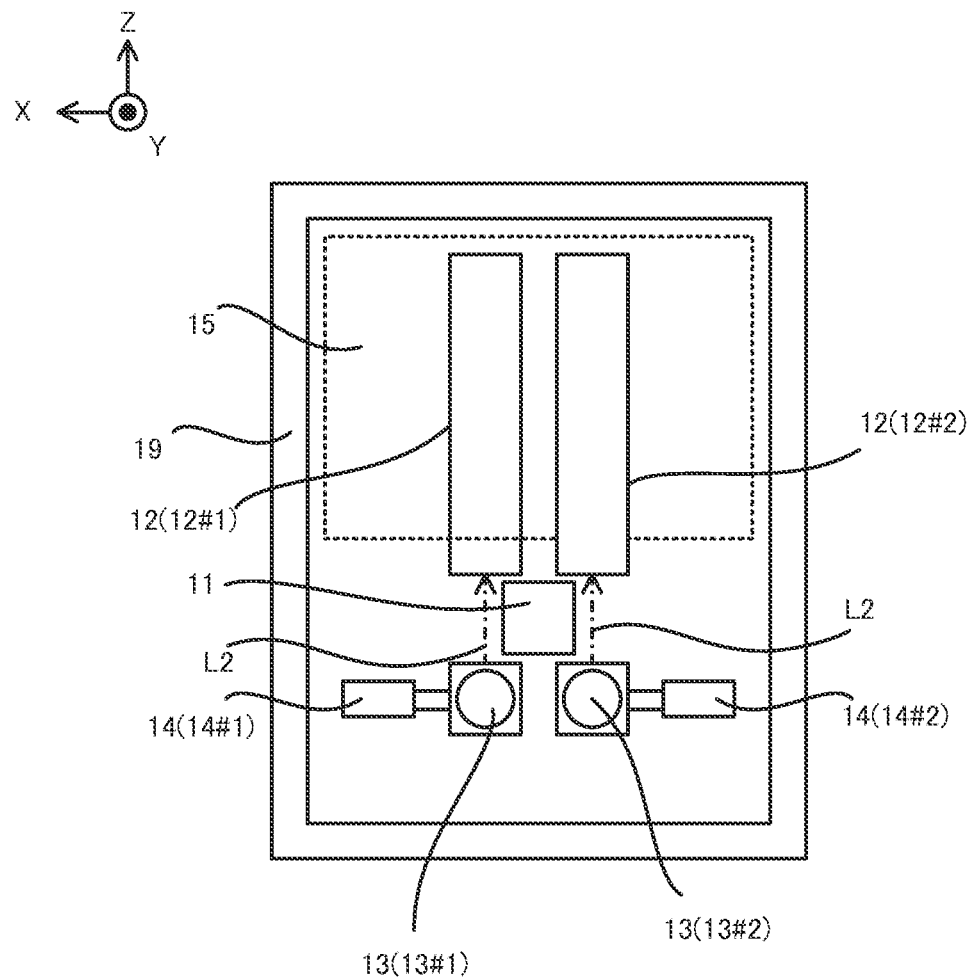
FIG. 37 is a cross-sectional view showing a configuration of the imaging unit in the seventh example embodiment.

Subsequently, a description will be given of a seventh example embodiment of the authentication system and the imaging apparatus. The following describes an authentication system SYSe in which the seventh example embodiment of the authentication system and the imaging apparatus is applied. The authentication system SYSe, as compared with the authentication system SYS described above differs in that the authentication system SYSe comprises an imaging unit 1e instead of the imaging unit 1. The other features of the authentication system SYSe may be identical to the other features of the authentication system SYS. Hereinafter, with reference to FIGS. 36 and 37, a description will be given of the imaging unit 1e in the seventh example embodiment. FIG. 36 is a block diagram showing a configuration of the imaging unit 1e in the seventh example embodiment. FIG. 37 is a cross-sectional view showing the configuration of the imaging unit 1e in the seventh example embodiment.

As shown in FIGS. 36 and 37, the imaging unit 1e differs from the imaging unit 1 described above in that the imaging unit 1e comprises a plurality of iris cameras 12, a plurality of rotation mirrors 13, and a plurality of rotation motors 14. In the example shown in FIGS. 36 and 37, the imaging unit 1e comprise two iris cameras 12 (specifically, the iris cameras 12 #1 and 12 #2), two rotation mirrors 13 (specifically, the rotation mirrors 13 #1 and 13 #2), and two rotation motors 14 (specifically, the rotation motors 14 #1 and 14 #2). In other words, in one housing 19, housed are the two iris cameras 12 (specifically, the iris cameras 12 #1 and 12 #2), the two rotation mirrors 13 (specifically, the rotation mirrors 13 #1 and 13 #2), and the two rotation motors 14 (specifically, the rotation motors 14 #1 and 14 #2). The other features of the imaging unit 1e may be identical to the other features of the imaging unit 1.

Figure 38:
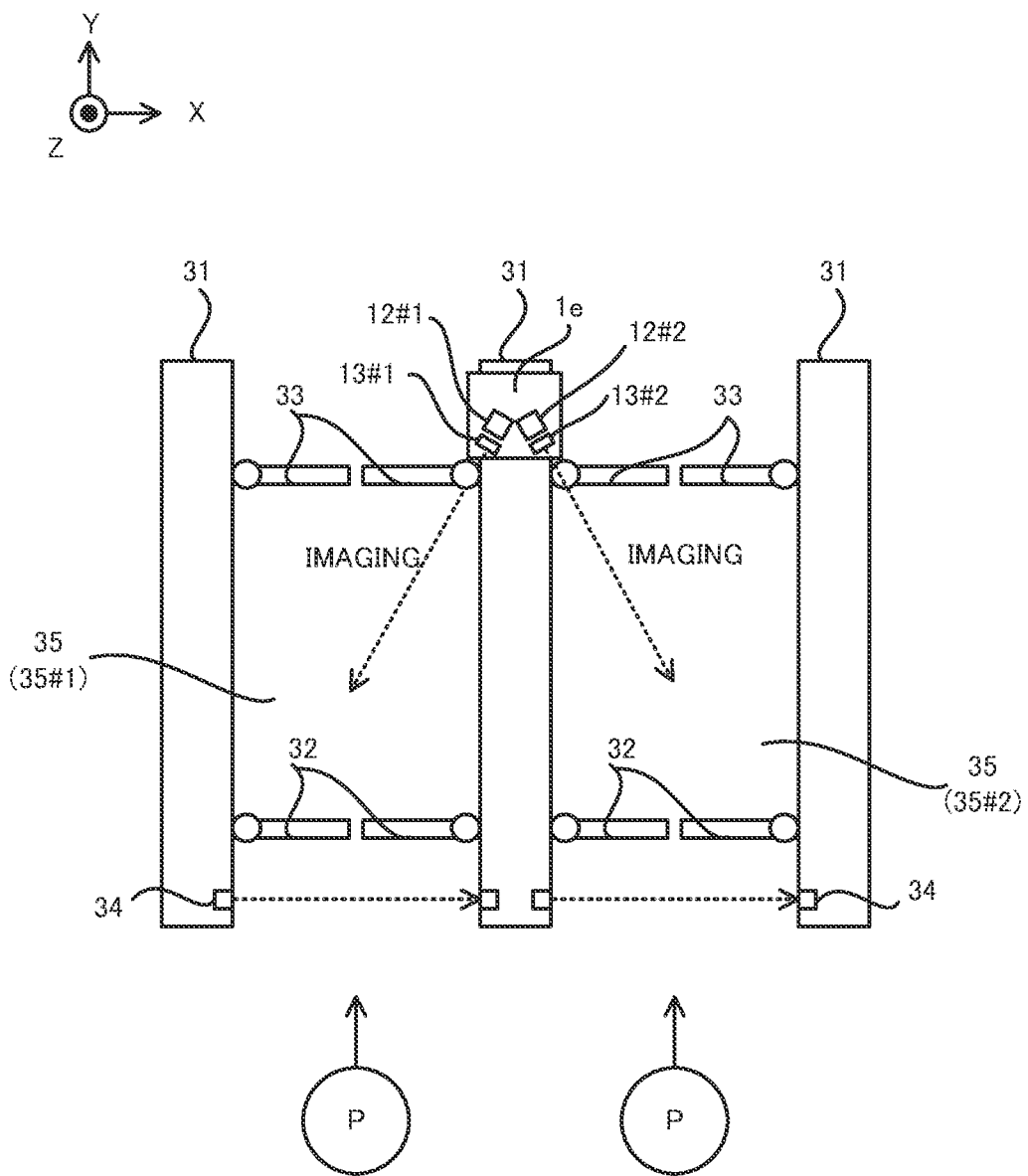
FIG. 38 is a top view showing an arrangement position of the imaging unit in the seventh example embodiment.

The plurality of iris cameras 12 image via the plurality of rotation mirrors 13, the eyes of a plurality of target people P going through the plurality of lanes 35 respectively. For example, as shown in FIG. 38, the iris camera 12 #1 may image the eyes of the target person P going through the first lane 35 #1 via the rotation mirror 13 #1 which the rotation motor 14 #1 rotates. On the other hand, for example, the iris camera 12 #2 may image, via the rotation mirror 13 #2 which the rotation motor 14 #2 rotates, the eyes of the target person P going through the second lane 35 #2 different from the first lane 35 #1. In this case, as shown in FIG. 38, the rotation mirror 13 #1 may be oriented toward the first lane 35 #1, while the rotation mirror 13 #2 may be oriented toward the second lane 35 #2. That is, the rotation mirrors 13 #1 and 13 #2 may face different directions from each other.

Figure 39:
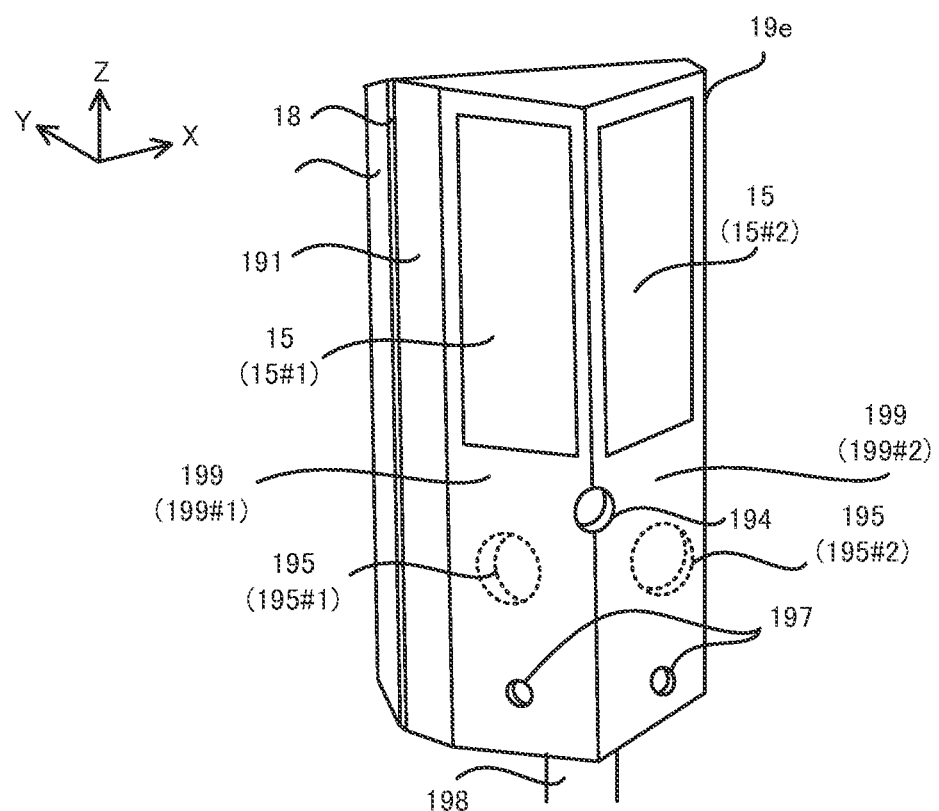
FIG. 39 is a perspective view showing another example of the imaging unit in the seventh example embodiment.
Figure 40:
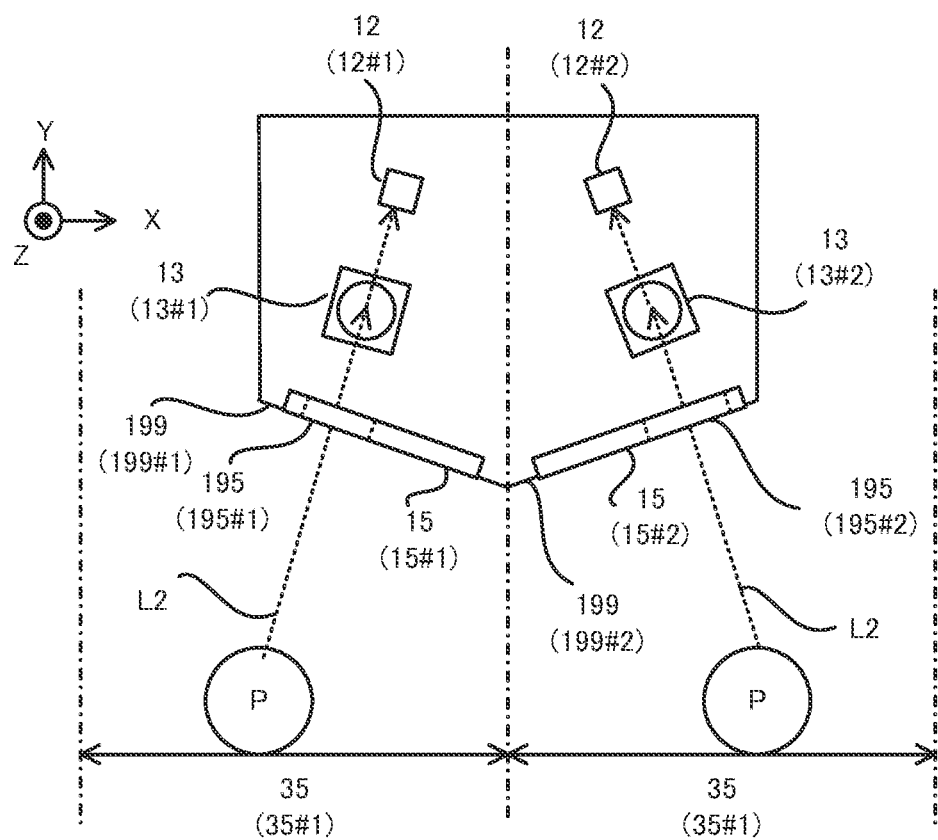
FIG. 40 is a perspective top view showing another example of the imaging unit in the seventh example embodiment.
Figure 41:
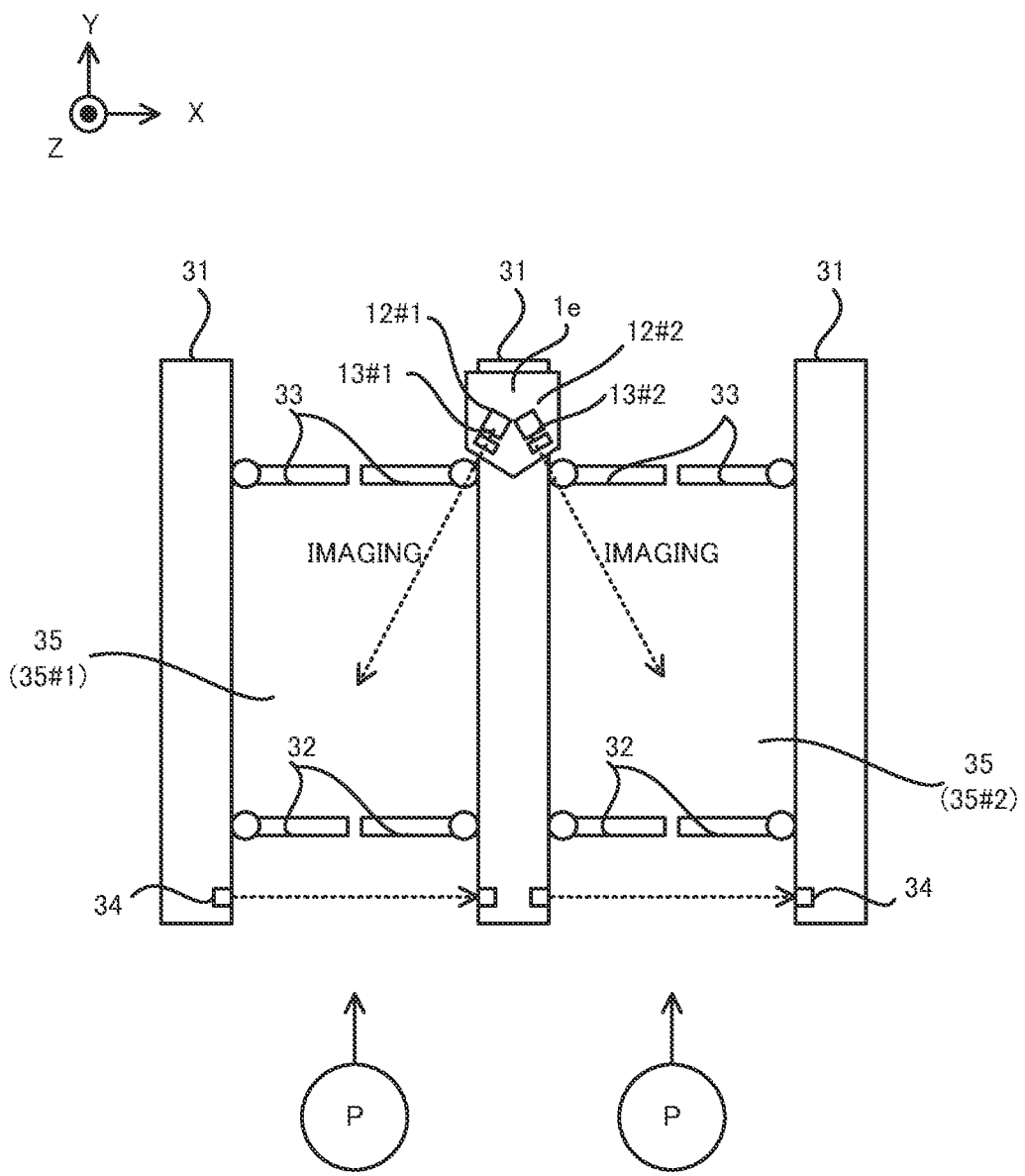
FIG. 41 is a top view showing an arrangement position of another example of the imaging unit in the seventh example embodiment.

When the rotation mirrors 13 #1 and 13 #2 are oriented in different directions from each other, as shown in FIGS. 39 to 41, the iris cameras 12 #1 and 12 #2, the rotation mirrors 13 #1 and 13 #2, and the rotation motors 14 #1 and 14 #2 may be housed in the housing 19e different from the housing 19 in that the housing 19e comprises: a side surface 199 #1 oriented toward the first lane 35 #1; and a side surface 199 #2 oriented toward the second lane 35 #2. In this case, the cross-sectional shape along the horizontal plane of the housing 19e may be a polygon such as a pentagon. On the rotation mirror 13 #1 which is oriented toward the first lane 35 #1, light L2 from the target person P located in the first lane 35 #1 may through the opening 195 (195 #1) formed in the side surface 199 #1, be incident. On the other hand, on the rotation mirror 13 #2 which is oriented toward the second lane 35 #2, light L2 from the target person P located in the second lane 35 #2 may through the opening 195 (195 #2) formed in the side surface 199 #2, be incident.

Furthermore, in this case, as shown in FIGS. 39 and 40, the imaging unit 1e may comprise: a display 15 #1 which is oriented toward the first lane 35 #1; and a display 15 #2 which is oriented toward the second lane 35 #2. As a result of that, the target person P located in the first lane 35 #1 is easy to view the display 15 #1, and the target person P located in the second lane 35 #2 is easy to view the display 15 #2.

Figure 42:
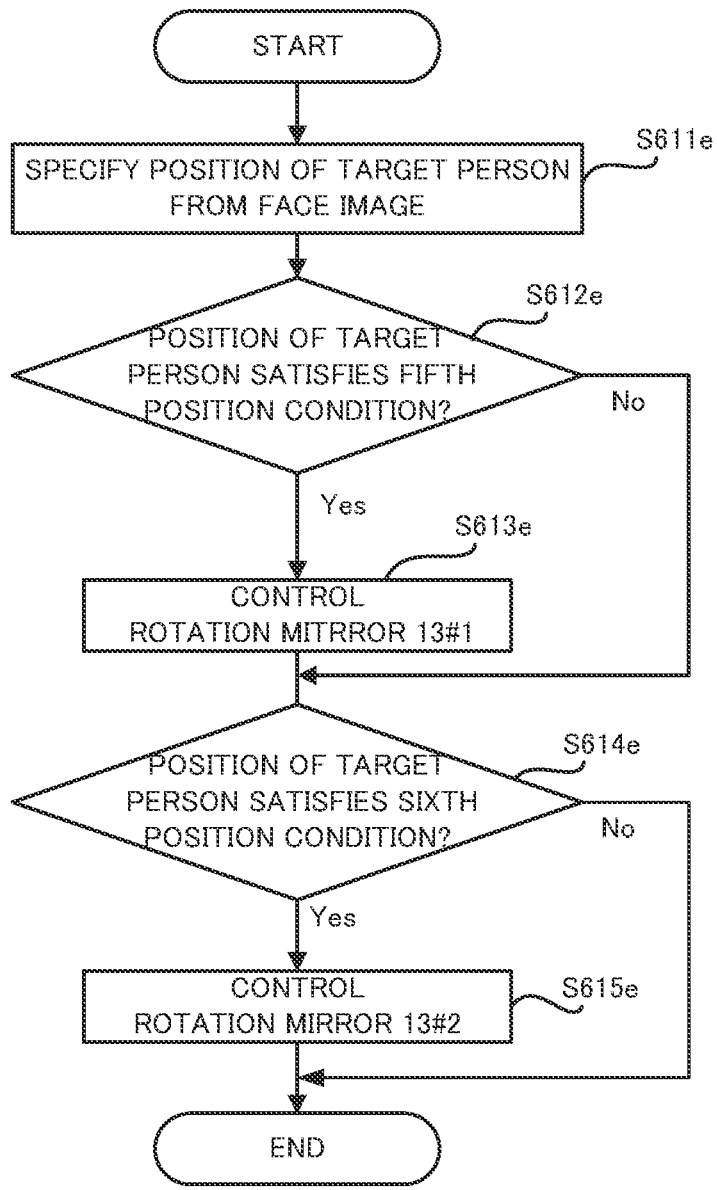
FIG. 42 is a flowchart showing a flow of operation to control two to more rotation mirrors.

In the seventh example embodiment, the mirror control unit 212 may control the plurality of rotation mirrors 13 (e.g., the rotation mirrors 13 #1 and 13 #2) in accordance with a flowchart shown in FIG. 42. FIG. 42 is the flowchart showing a flow of operation for controlling the plurality of rotation mirrors 13. The operation shown in FIG. 42 may be performed before the iris camera 12 captures the image of the iris of the target person P in step S108 of FIG. 12.

Specifically, as shown in FIG. 42, the mirror control unit 212 specifies the position (in particular, the position in the horizontal direction) of the target person P on the basis of the face image IMG_F (step S611e).

Thereafter, the mirror control unit 212 determines whether the position of the target person P specified in step S611e satisfies a predetermined fifth position condition (step S612e). The fifth position condition may include a condition that the target person P is located in the first lane 35 #1. The fifth position condition may include a condition that the target person P is located in a direction toward which the rotation mirror 13 #1 is oriented.

As a result of the determination in step S612e, when it is determined that the position of the target person P satisfies the predetermined fifth position condition (step S612e: Yes), the mirror control unit 212 controls the rotation mirror 13 #1 so that the rotation mirror 13 #1 oriented toward the first lane 35 #1 reflects light L2 from the target person P located in the first lane 35 #1 toward the iris camera 12 #1 (step S613e).

In parallel with, before, of after the operations from step S612e to step S613e, the mirror control unit 212 determines whether the position of the target person P specified in step S611e satisfies the predetermined sixth position condition different from the fifth position condition (step S614e). The sixth position condition may include a condition that the target person P is located in the second lane 35 #2. The sixth position condition may include a condition that the target person P is located in a direction toward which the rotation mirror 13 #2 is oriented.

As a result of the determination in step S614e, when it is determined that the position of the target person P satisfies the predetermined sixth position condition (step S614e: Yes), the mirror control unit 212 controls the rotation mirror 13 #2 so that the rotation mirror 13 #2 oriented toward the second lane 35 #2 reflects light L2 from the target person P located in the second lane 35 #2 toward the iris camera 12 #2 (step S615e).

As described above, the authentication system SYSe is capable of imaging, using a single imaging unit 1d, the plurality of target people P going through each of the plurality of lanes 35. Therefore, it is not necessary to provide a plurality of imaging units 1 for imaging the plurality of target people P going through the plurality of lanes 35 respectively. Therefore, it is possible to simplify the configuration of the authentication system SYSe, and also reduce the cost of the authentication system SYSe.

From the authentication system SYSa in the third example embodiment to the authentication system SYSd in the sixth example embodiment described above, at least one of them may employ components specific to the seventh example embodiment. The components specific to the seventh example embodiment may include components for the plurality of iris cameras 12 and the plurality of rotation mirrors 13.

(8) Eighth Example Embodiment

Figure 43:
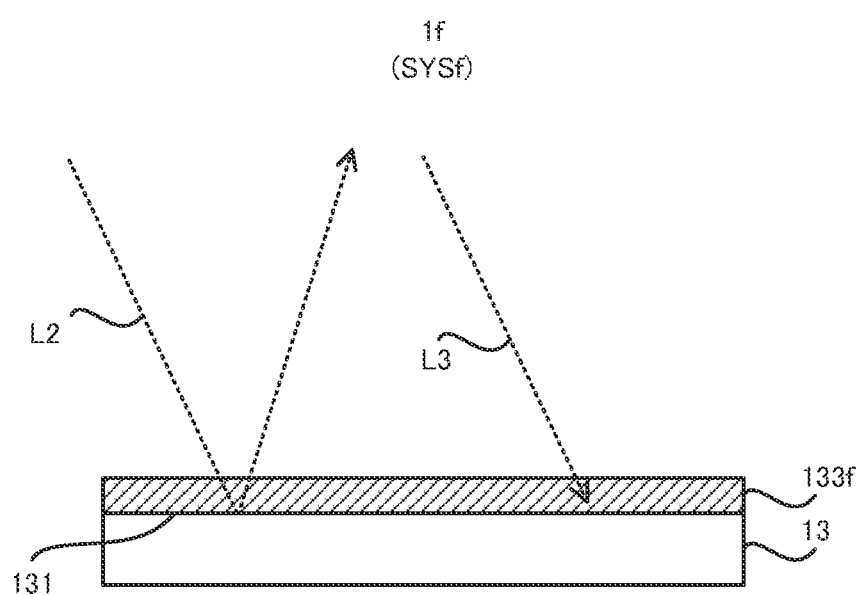
FIG. 43 is a cross-sectional view showing a rotation mirror which an imaging unit comprises in the eighth example embodiment.

Subsequently, a description will be given of an eighth example embodiment of the authentication system and the imaging apparatus. The following describes an authentication system SYSf in which the eighth example embodiment of the authentication system and the imaging apparatus is applied. The authentication system SYSf, as compared with the authentication system SYS described above, differs in that the authentication system SYSf comprises an imaging unit 1f instead of the imaging unit 1. The other features of the authentication system SYSf may be identical to the other features of the authentication system SYS. Hereinafter, with reference to FIG. 43, a description will be given of the imaging unit 1f in the eighth example embodiment. FIG. 43 is a cross-sectional view showing a rotation mirror 13 with which the imaging unit 1f in the eighth example embodiment is provided.

As shown in FIG. 43, the imaging unit 1f differs from the imaging unit 1 described above in that a protective film 133f is formed on the reflective surface 131 of the rotation mirror 13. The other features of the imaging unit 1f may be identical to the other features of the imaging unit 1.

The protective film 133f may be capable of protecting the reflective surface 131 so as to prevent breakage of the reflective surface 131. The protective film 133f may be capable of protecting the reflective surface 131 so as to prevent fouling from adhering to the reflective surface 131. The protective film 133f may be capable of protecting the reflective surface 131 so as to prevent moisture from adhering to the reflective surface 131 (that is, to prevent humidity). As a result of that, the reflective surface 131 is properly protected.

The protective film 133f may have an optical property that allows light L2 from the target person P to go therethrough. As a result of that, the iris camera 12 can image the target person P by receiving the light L2 from the target person P (that is, the light L2 from the iris).

Further, the protective film 133f may have an optical property that light L3 (e.g., visible light) having a wavelength band different from a wavelength band of the light L2 from the target person P is attenuated by the protective film 133f. For example, the protective film 133f may have an optical property that the light L3 having a wavelength band different from a wavelength band of the light L2 from the target person P is absorbed by the protective film 133f. At this time, the protective film 133f may have an optical characteristic that the light L3 having a wavelength band different from a wavelength band of the light L2 from the target person P cannot go through the protective film 133f. In this case, since the light L3 having a wavelength band different from the wavelength band of the light L2 is attenuated by the protective film 133f, as compared with the case where the protective film 133f is not formed, reduced is the possibility that a noise component is contained in the iris image IMG_I, the noise component being caused by the light L3 having the wavelength band different from the wavelength band of the light L2. As a result of that, as compared with the case where the target person P is authenticated using the iris image IMG_I including such a noise component, the iris authentication unit 211 can more accurately authenticate the target person P using the iris image IMG_I.

In this way, in the eighth example embodiment, the protective film 133f can reduce the noise component contained in the iris image IMG-I while protecting the reflective surface 131.

From the authentication system SYSa in the third example embodiment to the authentication system SYSe in the seventh example embodiment, at least one of them may employ components specific to the eighth example embodiment. The components specific to the eighth example embodiment may include components related to the protective film 133f.

(9) Ninth Example Embodiment

Figure 44:
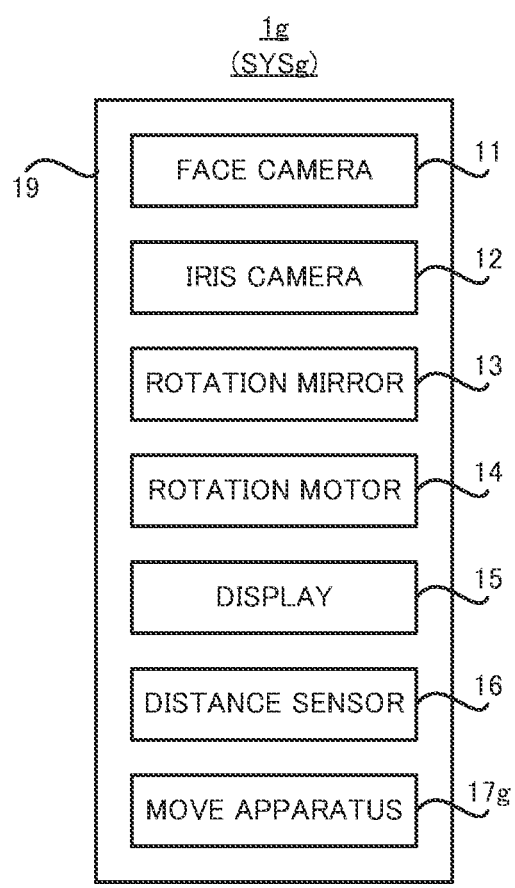
FIG. 44 is a block diagram showing a configuration of an imaging unit in the ninth example embodiment.

Subsequently, a ninth example embodiment of the authentication system and the imaging apparatus will be described. The following describes an authentication system SYSg in which the ninth example embodiment of the authentication system and the imaging apparatus is applied. The authentication system SYSg, as compared with the authentication system SYS described above, differs in that the authentication system SYSg comprises an imaging unit 1g instead of the imaging unit 1. The other features of the authentication system SYSg may be identical to the other features of the authentication system SYS. Hereinafter, with reference to FIG. 44, a description will be given of the imaging unit 1g in the ninth example embodiment. FIG. 44 is a block diagram showing a configuration of the imaging unit 1g in the ninth example embodiment.

As shown in FIG. 44, the imaging unit 1g, as compared with the imaging unit 1 described above, differs in that the imaging unit 1g comprises a move apparatus 17g. The other features of the imaging unit 1g may be the same as the other features of the imaging unit 1.

The move apparatus 17g is capable of moving the imaging unit 1g (in particular, the housing 19 where the face camera 11, the iris camera 12, the rotation mirror 13, the rotation motor 14 and the display 15 are housed). For example, the move apparatus 17g may be provided with a robot to move the imaging unit 1g using the robot arm. For example, the move apparatus 17g may be provided with a guide member (e.g., a rail guide) comprising a slider which is movable in a predetermined direction to move the imaging unit 1g using the rail guide. For example, the move apparatus 17g may be provided with a self-propelled apparatus capable of self-propelling, to move the imaging unit 1g using the self-propelled apparatus. For example, the move apparatus 17g may be provided with a flying object capable of flight (e.g., a drone), to move the imaging unit 1g using the flight object.

Figure 45A:
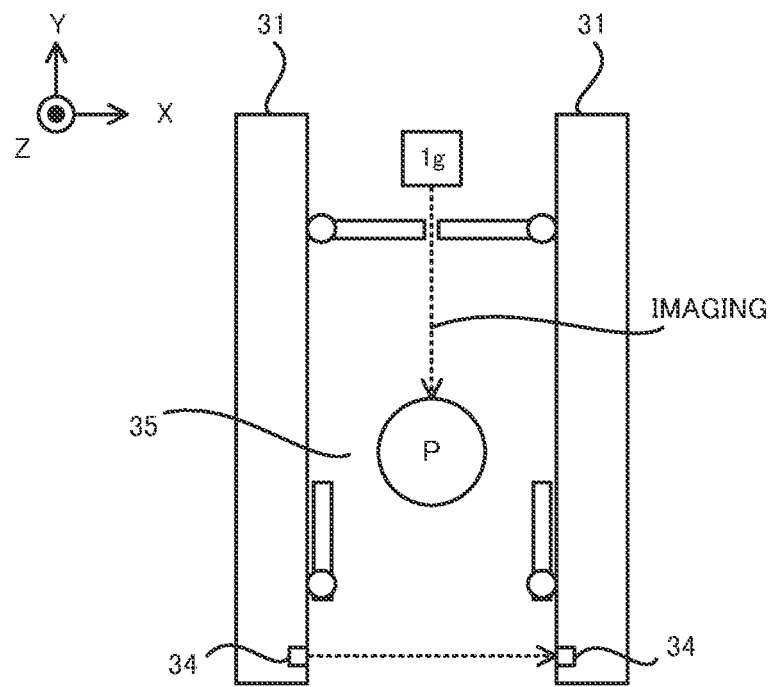
FIG. 45A is a top view showing the imaging unit in a period in which an iris camera captures the image of a target person.

The move apparatus 17g, as shown in FIG. 45A, may move the imaging unit 1g so that the imaging unit 1g is arranged on the lane 35 which the target person P is going through in a period when the iris camera 12 captures the image of the target person P. In this case, the iris camera 12 can image the target person P from the front. In other words, the iris camera 12 is not required to capture the image of the target person P from an oblique direction. As a result of that, the iris is less likely to be hidden in the iris image IMG_I by at least one of eyelashes, eyelids, and etc. as described above. As a result of that, the iris authentication unit 211 can authenticate the target person P with high accuracy.

Figure 45B:
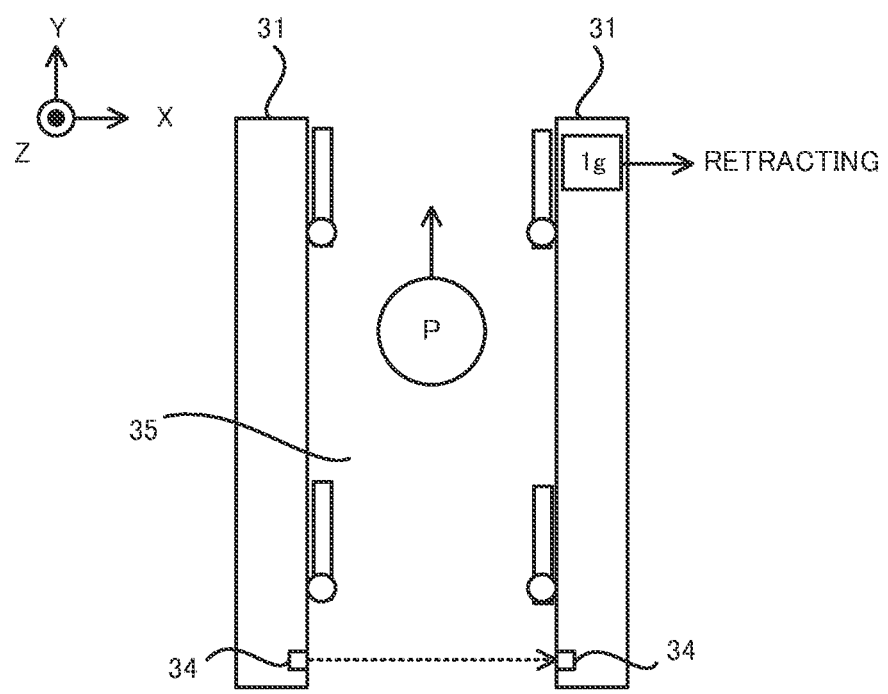
FIG. 45B is a top view showing the imaging unit in a period after the target person is authenticated.

On the other hand, if the imaging unit 1g was disposed on the lane 25 and is left in that state, there is a possibility that the movement of the target person P going through the lane 35 is hindered by the imaging unit 1g. Therefore, the move apparatus 17g, as shown in FIG. 45B, may move the imaging unit 1g in a period following after the target person P has been authenticated, so that the imaging unit 1g is retracted from the lane 35 which the target person P is going through. That is, the move apparatus 17g may move the imaging unit 1g in the period following after the target person P has been authenticated, so that the imaging unit 1g is positioned at a position where the imaging unit 1g does not hinder the movement of the target person P going through the lane 35. As a result of that, the movement of the target person P is not hindered by the imaging unit 1g.

In the ninth example embodiment, the move apparatus 17g may perform operation of moving the imaging unit 1g in accordance with a flowchart shown in FIG. 46. The operation shown in FIG. 46 may be performed in parallel with, before, or after the operation shown in FIG. 12.

Specifically, as shown in FIG. 46, the move apparatus 17g determines whether the proximity sensor 34 of the gate unit 3 has detected the target person P (step S711g). As a result of the determination of step S711g, when it is determined that the proximity sensor 34 has detected the target person P (step S711g: Yes), it is estimated that the imaging unit 1 is going to capture the image of the target person P because the target person P enters the lane 35. Therefore, in this case, the move apparatus 17g moves the imaging unit 1g so that the imaging unit 1g is arranged on the lane 35 which the target person P is going through (step S712g).

Thereafter, the move apparatus 17g determines whether or not the authentication of the target person P is successful in step S109 in FIG. 12 (step S713g). As a result of the determination of step S713g, when it is determined that the authentication of the target person P is successful (step S713g: Yes), it is estimated that the target person P would go through the lane 35. Therefore, in this case, the move apparatus 17g moves the imaging unit 1g so that the imaging unit 1g is retracted from the lane 35 which the target person P is going through (step S714g).

Thus, in the ninth example embodiment, since the move apparatus 17g is capable of moving the imaging unit 1g, it is possible for the imaging unit 1g to capture the image of, without hindering the movement of the target person P, the eyes of the target person P from the front of the target person P.

Figure 47A:
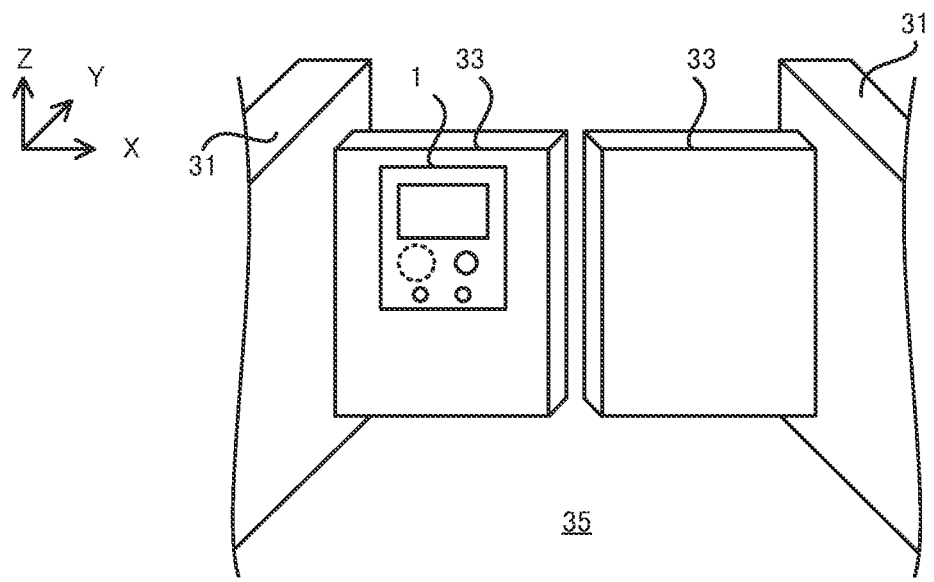
FIG. 47A is a top view showing the imaging unit in a period in which an iris camera captures the image of a target person.
Figure 47B:
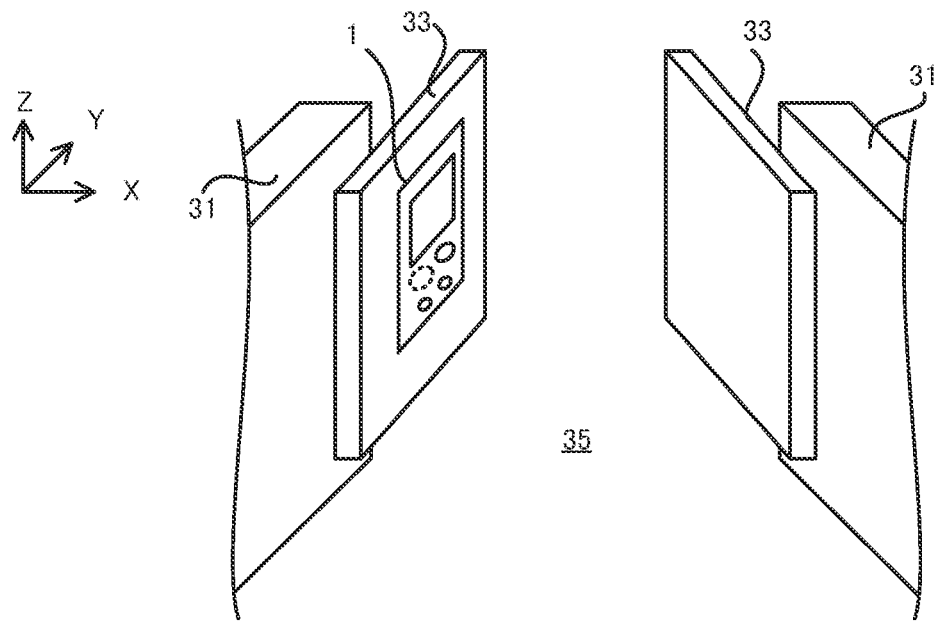
FIG. 47B is a top view showing the imaging unit in a period after the target person is authenticated.

In addition to or in place of the imaging unit 1g provided with the move apparatus 17g, an apparatus other than the imaging unit 1 may move the imaging unit 1. As an example, as shown in FIG. 47A and FIG. 47B, the imaging unit 1 may be disposed on the second flapper gate 33 of the gate unit 3. In this case, during the period when the iris camera 12 captures the image of the target person P, since the state of the second flapper gate 33 is in the closed state, as shown in FIG. 47A, the iris camera 12 can image the target person P from the front. On the other hand, if the target person P is successfully authenticated, in the period following after the target person P has been authenticated, since the state of the second flapper gate 33 is in the open state as shown in FIG. 47B, the movement of the target person P is not hindered by the imaging unit 1.

Figure 48:
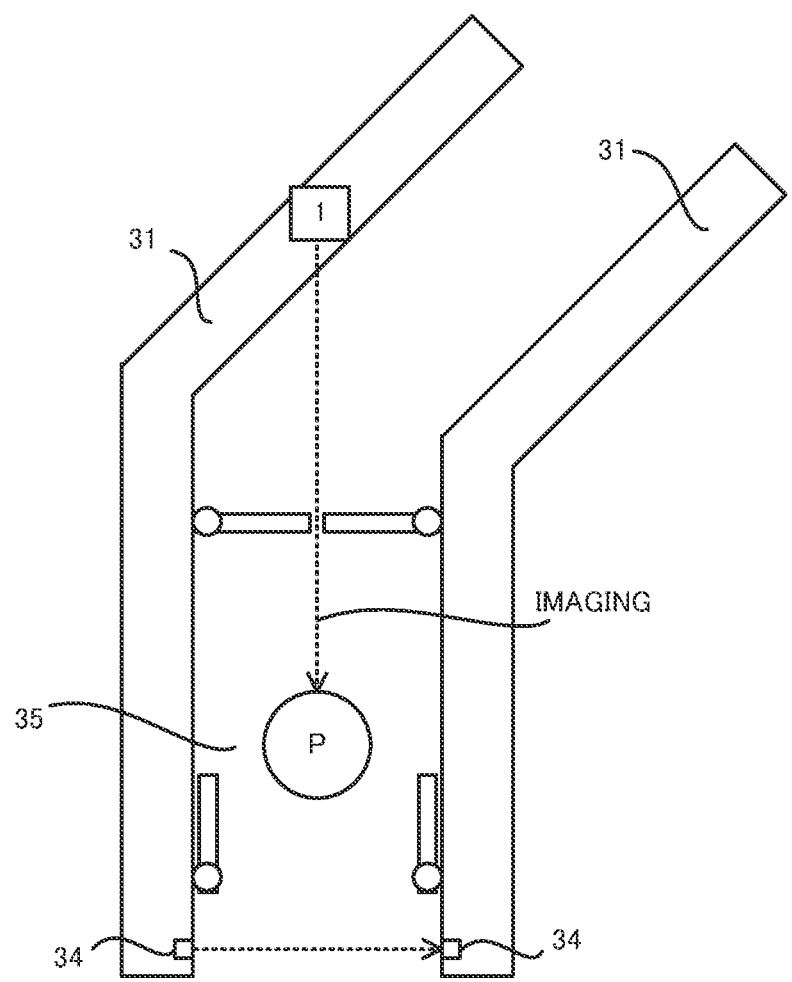
FIG. 48 is a top view showing a bent lane.

Further, in order to realize the state that the imaging unit 1 captures the image of the eyes of the target person P from the front of the target person P without hindering the movement of the target person P, as shown in FIG. 48, a bent-shaped lane 35 may be formed. In other words, the lane 35 may be formed in a predetermined shape (e.g., a shape different from a linear shape), the shape being designed so as to allow the imaging unit 1 to be disposed at a position where the imaging unit 1 can image the eyes of the target person P from the front of the target person P, and also, so as not to allow the imaging unit 1 to hinder the movement of the target person P.

From the authentication system SYSa in the third example embodiment to the authentication system SYSf in the eighth example embodiment described above, at least one of them may employ components specific to the ninth example embodiment. The components specific to the ninth example embodiment may include components related to the move apparatus 17g.

(10) Tenth Example Embodiment

Subsequently, a description will be given of a tenth example embodiment of the authentication system and the imaging apparatus. The following describes an authentication system SYSh in which the tenth example embodiment of the authentication system and the imaging apparatus is applied. The authentication system SYSh differs in that the rotation mirror 13 is available as a heat releasing fan as compared to the authentication system SYS described above. Specifically, the authentication system SYSh may control the rotation motor 14 so that the rotation mirror 13 functions as the heat releasing fan by rotating continuously in the same rotational direction. As a result of that, the influence of heat on the operation of the face camera 11, the iris camera 12, and the display 15 is reduced.

Figure 49:
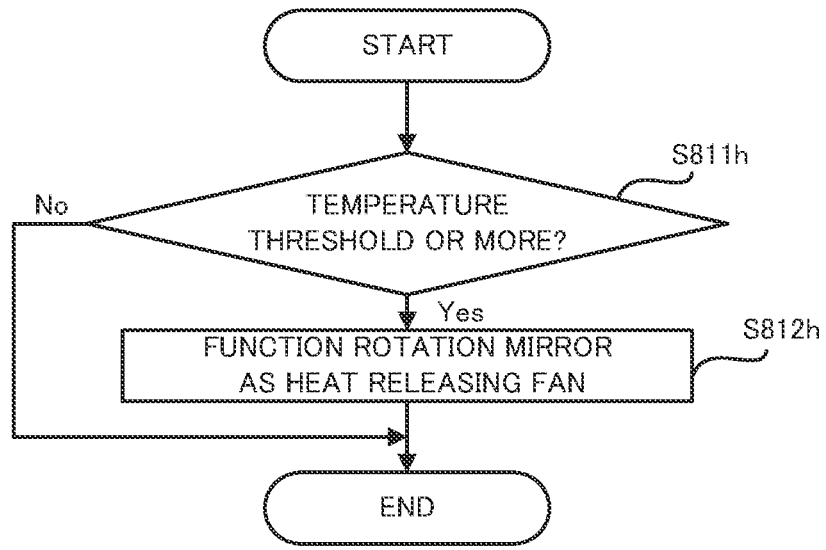
FIG. 49 is a flowchart showing a flow of operation to drive a rotation mirror as a heat releasing fan.

In the tenth example embodiment, the mirror control unit 212 may perform operation of driving the rotation mirror 13 as the heat releasing fan in accordance with a flowchart shown in FIG. 49. The operation shown in FIG. 49 may be performed in parallel with, before, or after the operation shown in FIG. 12. As shown in FIG. 49, the mirror control unit 212 determines whether the temperature of the housing space SP1 of the housing 19 has become a predetermined temperature threshold or more (step S811h). If it is determined that the temperature of the housing space SP1 has become the predetermined temperature threshold or more (step S811h: Yes), the mirror control unit 212 drives the rotation mirror 13 as the heat releasing fan (step S812h). On the other hand, if it is determined that the temperature of the housing space SP1 has not become the predetermined temperature threshold or more (step S811h: No), the mirror control unit 212 may not drive the rotation mirror 13 as the heat releasing fan.

From the authentication system SYSa in the third example embodiment to the authentication system SYSg in the ninth example embodiment described above, at least one of them may employ components specific to the tenth example embodiment. The components specific to the ninth example embodiment may include components related to the rotation mirror 13 that serves as the heat releasing fan. However, the authentication system SYSb in the fourth example embodiment, as described above, comprises the stopper 141b for limiting the rotation of the rotation mirror 13. In this case, it is preferable that the stopper 141b is not allowed to limit the rotation of the rotation mirror 13 during the term in which the rotation mirror 13 functions as the heat releasing fan. For example, the stopper 141b may be retracted to a position where the stopper 141v does not limit the rotation of the rotation mirror 13 (e.g., may be housed).

(11) Eleventh Example Embodiment

Figure 50:
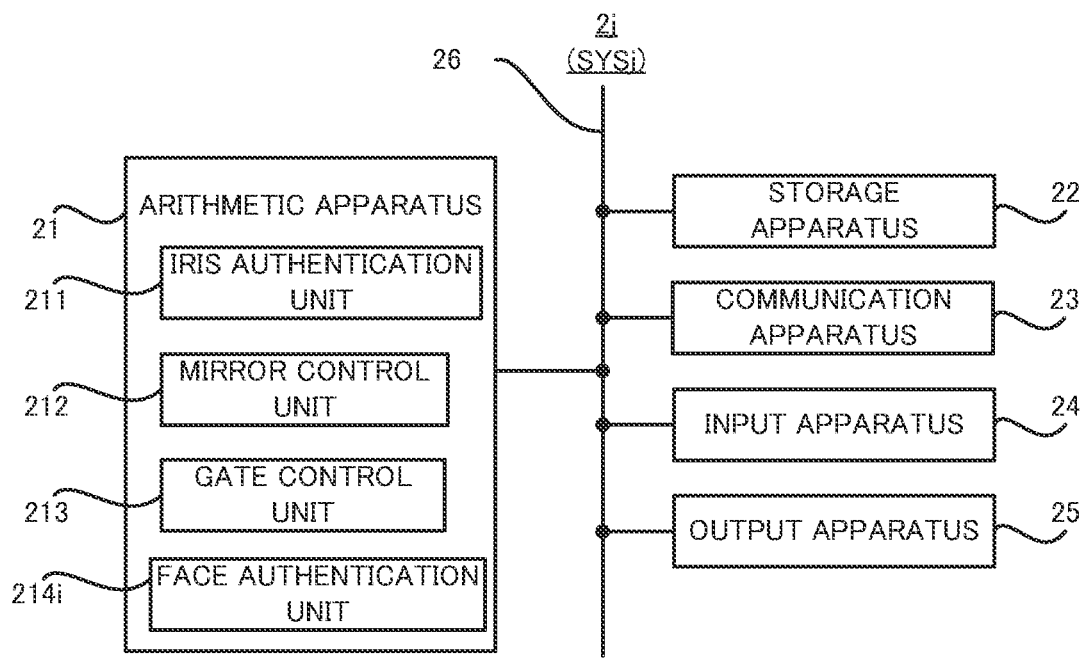
FIG. 50 is a block diagram showing a configuration of a control unit in the eleventh example embodiment.

Subsequently, a description will be given of an eleventh example embodiment of the authentication system and the imaging apparatus. The following describes an authentication system SYSi in which the eleventh example embodiment of the authentication system and the imaging apparatus is applied. The authentication system SYSi, as compared with the authentication system SYS described above, differs in that the authentication system SYSi comprises a control unit 2i instead of the control unit 2. The other features of the authentication system SYSi may be identical to the other features of the authentication system SYS. Hereinafter, with reference to FIG. 50, a description will be given of the control unit 2i in the eleventh example embodiment. FIG. 50 is a block diagram showing a configuration of the control unit 2i in the eleventh example embodiment.

As shown in FIG. 50, the control unit 2i differs from the control unit 2 described above in that the control unit 2i further comprises a face authentication unit 214i. The other features of the control unit 2i may be identical to the other features of the control unit 2.

Figure 51:
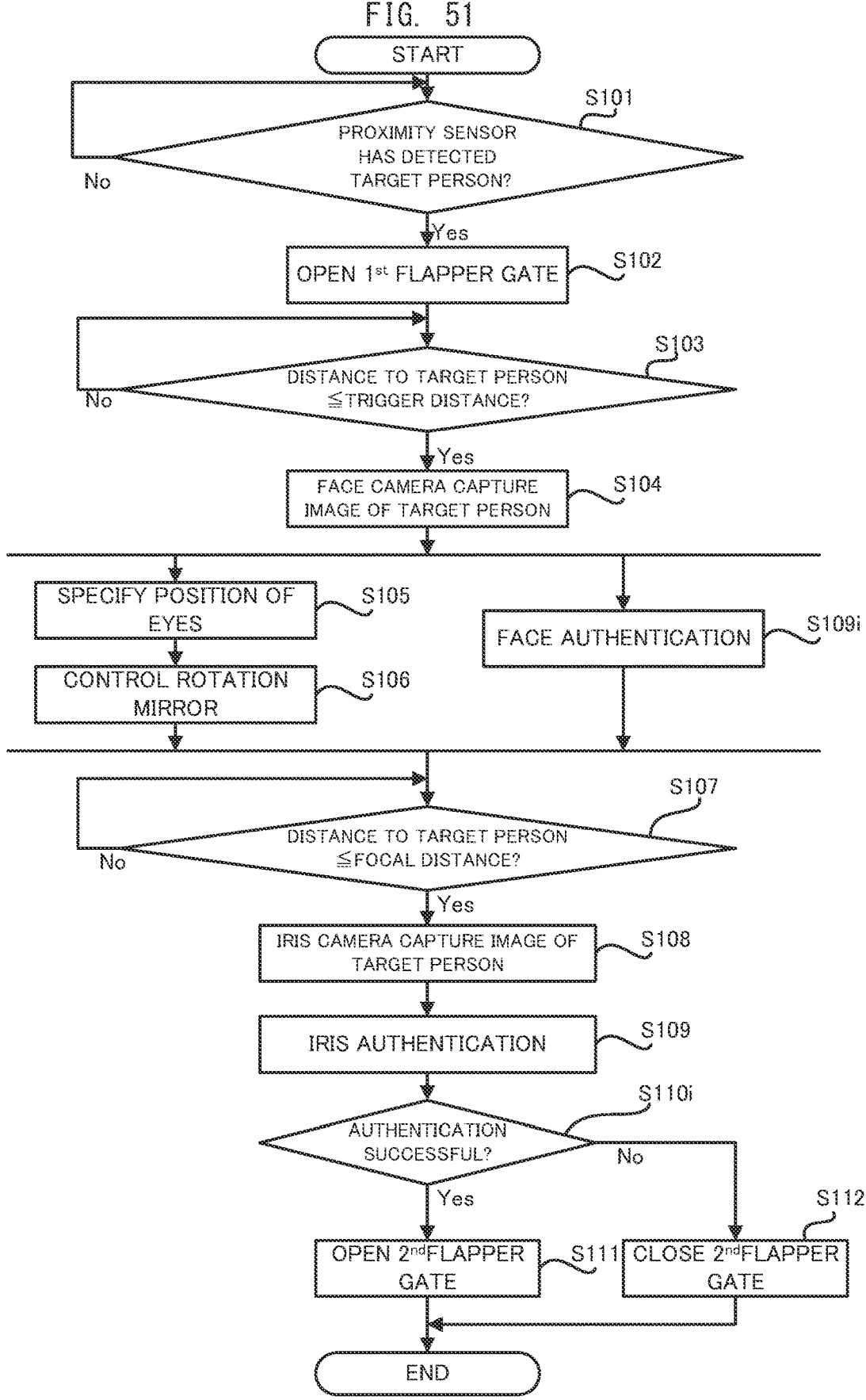
FIG. 51 is a flowchart showing a flow of authentication operation performed by a control unit in the eleventh example embodiment.

Next, an authentication operation performed by the control unit 2i comprising the face authentication unit 214i will be described with reference to FIG. 51. FIG. 51 is a flowchart showing a flow of the authentication operation performed by the control unit 2i.

As shown in FIG. 51, even in the eleventh example embodiment, the control unit 2i performs the operation from step S101 to step S109 similarly to the second example embodiment described above (see FIG. 12). However, in the eleventh example embodiment, after the face camera 11 captures the image of the face of the target person P in step S104, the face authenticating unit 214i acquires the face image IMG_F from the face camera 11 via the communication apparatus 23, and authenticates the target person P based on the acquired face image IMG_F in step S109i. That is, the face authentication unit 214i performs the authentication operation related to face authentication. Specifically, the face authentication unit 214i determines whether or not the target person P captured in the acquired face image IMG_F matches a person registered in advance (hereinafter referred to as a "registered person"), based on the feature amount of the face of the target person P captured in the acquired face image IMG_F. When it is determined that the target person P captured in the face image IMG_F matches the registered person, it is determined that the authentication of the target person P is successful. On the other hand, when it is determined that the target person P captured in the face image IMG_F does not match the registered person, it is determined that the authentication of the target person P is failed.

Thereafter, when the target person P is successfully authenticated in step S109 and also the target person P is successfully authenticated in step S109i (Step S110i: Yes), the gate control unit 213 transmits a gate control signal for setting the state of the second flapper gate 33 to the open state via the communication apparatus 23 to the gate unit 3 (Step S111). On the other hand, if the authentication of the target person P fails in step S109 and also/or the authentication of the target person P fails in step S109i (Step S110i: No), the gate control unit 213 transmits a gate control signal for setting the state of the second flapper gate 33 to the closed state via the communication apparatus 23 to the gate unit 3 (Step S112).

Thus, the authentication system SYSi can perform so-called multi-modal authentication to more strictly authenticate the target person P.

(12) Twelfth Example Embodiment

Figure 52:
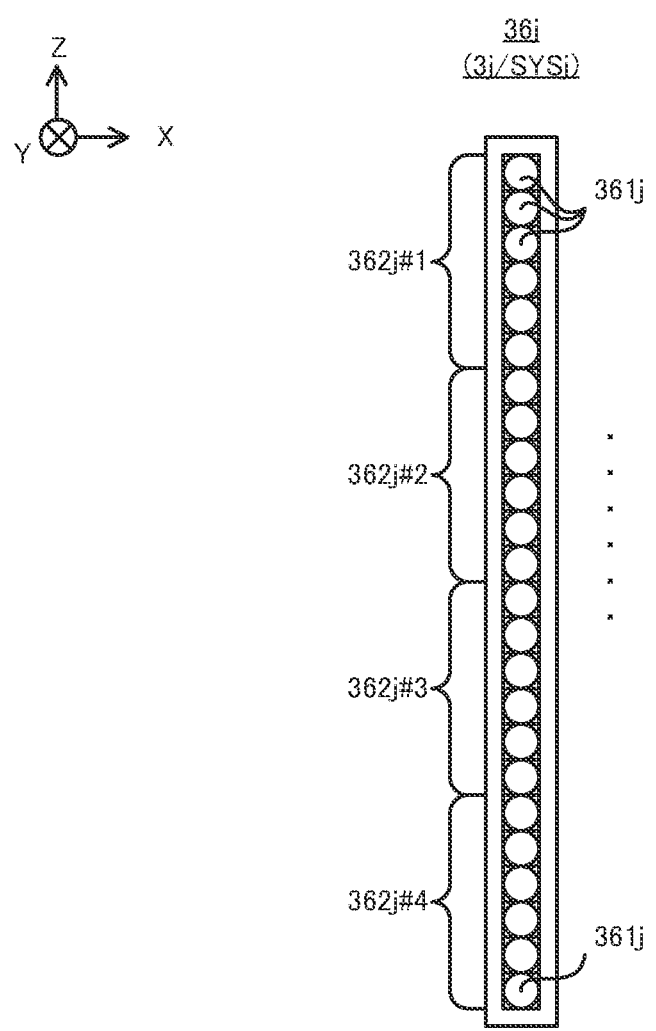
FIG. 52 is a front view showing a configuration of an illumination apparatus in the twelfth example embodiment.

Subsequently, a description will be given of a twelfth example embodiment of the authentication system and the imaging apparatus. The following describes the authentication system SYSj to which the twelfth example embodiment of the authentication system and the imaging apparatus is applied. The authentication system SYSj, as compared with the authentication system SYS described above, differs in that the authentication system SYSj comprises a gate unit 3j instead of the gate unit 3. The other features of the authentication system SYSj may be identical to the other features of the authentication system SYS. The gate unit 3j, as compared with the gate unit 3, differs in that the gate unit 3j comprises an illumination apparatus 36j instead of the illumination apparatus 3. The other features of the gate unit 3j may be the same as the other features of the gate unit 3. Hereinafter, with reference to FIG. 52, the illumination apparatus 36j in the twelfth example embodiment will be described. FIG. 52 is a front view showing a configuration of the illumination apparatus 3j in the twelfth example embodiment.

As shown in FIG. 52, the illumination apparatus 36j comprises a plurality of light emitting elements 361j. In the example embodiment shown in FIG. 52, the illumination apparatus 36j comprises 24 pieces of light emitting elements 361j, but the illumination apparatus 36j may comprise 23 or less pieces of light emitting elements 361j or 25 or more pieces of light emitting elements 361j.

The plurality of light emitting elements 361j are arranged along the Z-axis direction. The illumination apparatus 36j may control the plurality of light emitting elements 361j so that at least a part of the plurality of light emitting elements 361j emit the illumination light IL appropriately to the height of the target person P. For example, the 24 pieces of light emitting elements 361j may be divided into a light emitting element group 362j including a predetermined number of light emitting elements 361j. In this instance, the illumination apparatus 36j may select the light emitting element group(s) 362j that should emit the illumination light IL appropriately to the height of the target person P, and a predetermined number of light-emitting elements 361j included in the selected light-emitting element group(s) 362j may emit the illumination light IL.

In the example shown in FIG. 52, the 24 pieces of light-emitting elements 361j are divided into a light-emitting element group 362j #1 including the first to sixth light-emitting elements 361j from the top, a light-emitting element group 362j #2 including the seventh to twelfth light-emitting elements 361j from the top, a light-emitting element group 362j #3 including the thirteenth to eighteenth light-emitting elements 361j from the top, and a light-emitting element group 362j #4 including the nineteenth to twenty-fourth light-emitting elements 361j from the top. For example, when the height of the target person P is equal to or higher than the first threshold value (e.g., 190 cm), 6 pieces of light-emitting elements 361j included in the light emitting element group 362j #1 may emit the illumination light IL, while the other 18 pieces of light emitting elements 361j included in the light emitting element groups 362j #2 to 362j #4 may not emit the illumination light IL. For example, when the height of the target person P is less than the second threshold value (e.g., 130 cm), 12 pieces of light emitting elements 361j included in the light emitting element groups 362j #3 and 362j #4 may emit the illumination light IL, while the other 12 pieces of light emitting elements 361j included in the light emitting element groups 362j #1 to 362j #2 may not emit the illumination light IL.

In this manner, the illumination apparatus 36j of the authenticating system SYSj can illuminate the target person P using the illumination light IL emitted from the light emitting elements 361j positioned at a height appropriately to the height of the target person P.

(13) Supplementary Note

With respect to the example embodiment described above, further discloses the following supplementary notes.

[Supplementary Note 1]
An authentication system comprising:
an imaging unit that is capable of generating an iris image by capturing an image of an iris of an target; and
a display unit that is capable of displaying information related to authentication of the target using the iris image, wherein
at least a part of the imaging unit is disposed in a space adjacent to a back surface of the display unit, the back surface being located opposite a display surface for displaying the information, and
the imaging unit is oriented in a direction different from a direction in which the target is present.

[Supplementary Note 2]
The authentication system according to the supplementary note 1, wherein
the imaging unit is an iris imaging unit, and
the authentication system further comprises:
a reflective unit that includes a reflective surface capable of reflecting light from the iris toward the iris imaging unit;
a rotation driving unit that rotates the reflective unit;
a face imaging unit that is capable of generating a face image by capturing an image of a face of the target; and
a rotation control unit that specifies a position of eyes of the target based on the face image, and controls the rotation driving unit to change an orientation of the reflective surface based on the position of the eyes specified.

[Supplementary Note 3]
The authentication system according to the supplementary note 2, further comprising at least one of a first position adjustment unit capable of adjusting a position of the iris imaging unit and a second position adjustment unit capable of adjusting a position of the reflective unit.

[Supplementary Note 4]
The authentication system according to the supplementary note 2 or 3, further comprising
a rotation limiting unit that limits a rotation of the reflective unit by contacting the reflective unit when the reflective unit rotates by an allowable upper limit angle from a reference position, wherein
the rotation control unit, (i) controls the rotation driving unit so that the reflective unit rotates until the reflective unit contacts the rotation limiting unit, and (ii) calibrates the rotation driving unit based on a difference between: an actual command signal used for controlling the rotation driving unit so that the reflective unit rotates until the reflective unit contacts the rotation limiting unit; and an ideal command signal for controlling the rotation driving unit so that the reflective unit rotates by the allowable upper limit angle.

[Supplementary Note 5]
The authentication system according to any one of the supplementary notes 2 to 4, wherein the rotation control unit controls a deceleration of the reflective unit when the rotating reflective unit stops, based on a state of the iris captured in the iris image.

[Supplementary Note 6]
The authentication system according to the supplementary notes 2 to 5, wherein
the iris imaging unit generates a plurality of the iris images by capturing an image of the eyes a plurality of times respectively after the rotation driving unit stops the rotating reflective unit, and
the authentication system further comprises an authentication unit that selects within the plurality of the iris images, at least one iris image where the iris is captured in a desired position, and authenticates the target using the at least one selected iris image selected.

[Supplementary Note 7]
The authentication system according to the supplementary notes 2 to 6, wherein:
the reflective unit is a first reflective unit;
the authentication system further comprises:
a first reflective unit that is the reflective unit;
a second reflective unit that reflects light from the iris positioned at a first position toward the first reflective unit; and
a third reflective unit that reflects light from the iris positioned at a second position different from the first position toward the first reflective unit, wherein
the rotation control unit, (i) controls the second reflective unit so that when the specified position of the eyes satisfies a predetermined first position condition, the first reflective unit reflects the light from the second reflective unit toward the iris imaging unit, and (ii) controls the third reflective unit so that when the specified position of the eyes satisfies a predetermined second position condition, the first reflective unit reflects the light from the third reflective unit toward the iris imaging unit.

[Supplementary Note 8]
The authentication system according to the supplementary note 7, wherein
the second reflective unit reflects the light from the iris positioned at the first position toward the first reflective unit via a fourth reflective unit, and
the third reflective unit reflects the light from the iris positioned at the second position toward the first reflective unit via the fourth reflective unit.

[Supplementary Note 9]
The authentication system according to any one of the supplementary notes 2 to 8, wherein
the iris imaging unit is a first iris imaging unit capable of capturing an image of the iris positioned at a first position,
the reflective unit is a first reflective unit capable of reflecting light from the iris positioned at the first position toward the first iris imaging unit, and
the authentication system further comprises:
a second iris imaging unit capable of generating the iris image by capturing an image of the iris positioned at a second position different from the first position; and
a second reflective unit capable of reflecting light from the iris positioned at the second position toward the second iris imaging unit,
wherein the rotation control unit (i) specifies a position of the target based on the face image, (ii) controls the first reflective unit when the target is positioned at the first position so that the light from the iris of the target positioned at the first position is reflected toward the first iris imaging unit, and (iii) controls the second reflective unit when the target is positioned at the second position so that the light from the iris of the target positioned at the second position is reflected toward the second iris imaging unit.

[Supplementary Note 10]
The authentication system according to any one of the supplementary notes 7 to 9, wherein the second position is different from the first position with respect to at least one of a vertical direction and a horizontal direction.

[Supplementary Note 11]

The authentication system according to any one of the supplementary notes 2 to 10, wherein
the iris imaging unit captures an image of the iris illuminated with illumination light of a first wavelength band, and
a protective film is formed on the reflective surface, the protective film allowing light of the first wavelength band to go therethrough, attenuating light of a second wavelength band different from the first wavelength band, and capable of protecting the reflective surface.

[Supplementary Note 12]

The authentication system according to any one of the supplementary notes 2 to 11, wherein
the rotation control unit controls the rotation driving unit so that the reflective unit functions as a heat releasing fan by rotating continuously in a same rotational direction.

[Supplementary Note 13]

The authentication system according to any one of the supplementary notes 1 to 12, further comprising an authentication unit that authenticates the target using the iris image, wherein
the imaging unit is disposed on a passage which the target is going through, in a first period when the imaging unit captures an image of the target, and
the imaging unit retracts from the passage in a second period following after the target is authenticated.

[Supplementary Note 14]

The authentication system according to any one of the supplementary notes 1 to 13, further comprising:
a support unit that supports the imaging unit; and
a housing unit that houses the imaging unit supported by the support unit therein,
wherein a part of the support unit is exposed to an outside of the housing unit.

[Supplementary Note 15]

An imaging apparatus comprising:
an imaging unit that is capable of generating an iris image by capturing an image of an iris of an target; and
a display unit that is capable of displaying information related to authentication of the target using the iris image, wherein
at least a part of the imaging unit is disposed in a space adjacent to a back surface of the display unit, the back surface being located opposite a display surface for displaying the information, and
the imaging unit is oriented in a direction different from a direction in which the target is present.

At least a part of the components of each of the above-described example embodiments can be appropriately combined with at least another part of the components of each of the above-described example embodiments. A part of the components of the respective example embodiments described above may not be used. Also, to the extent permitted by law, the disclosure of all documents cited in this disclosure described above (e.g., public publications) shall be incorporated as part of the description of this disclosure.

This disclosure may be modified appropriately in a range which is not inconsistent with this technical idea, which can be acquired by the claims and the entire specification. Authentication systems and imaging apparatus with such modifications are also included in the technical idea of this disclosure.

DESCRIPTION OF REFERENCE SIGNS

1 Imaging Unit
11 Face Camera
12 Iris Camera
121 Optical System
122 Image Pickup Device
13 Rotation Mirror
13d Relay Mirror
131 Reflective Surface
132b Mirror Body
133b Mirror Holder
14 Rotation Motor
141b Stopper
15 Display
16 Distance Sensor
171a Camera Position Adjustment Mechanism
172a Mirror Position Adjustment Mechanism
17g Moving Apparatus
18 Support Plate
19 Housing
2 Control Unit
21 Arithmetic apparatus
211 Iris Authentication Unit
212, 212c Mirror Control Unit
213 Gate Control Unit
3 Gate Unit
31 Guide Wall
32 First Flapper Gate
33 Second Flapper Gate
34 Proximity Sensor
35 Lane
1000 Authentication System
1010 Imaging Apparatus
1020 Display Apparatus
2000 Target
SYS Authentication System
P Target Person
IMG_F Face Image
IMG_I Iris image

What is claimed is:

1. An authentication system comprising:
an imager that is capable of generating an iris image by capturing an image of an iris of a target; and
a display that is capable of displaying information related to authentication of the target using the iris image, wherein
the imager includes an image sensor,
the display includes a display surface on which the information is displayed,
the display surface overlaps with the image sensor as viewed from a direction orthogonal to the display surface,
the image sensor is disposed behind the display, and
the imager is oriented in a direction different from a direction in which the target is present.

2. The authentication system according to claim 1, wherein
the imager is an iris imager, and
the authentication system further comprises:
a reflector that includes a reflective surface capable of reflecting light from the iris toward the iris imager;
a rotation driver that rotates the reflector;
a face imager that is capable of generating a face image by capturing an image of a face of the target;
at least one memory configured to store instructions; and
at least one processor configured to execute the instructions to specify a position of eyes of the target based on the face image, and controls the rotation driver to change an orientation of the reflective surface based on the position of the eyes specified.

3. The authentication system according to claim 2, further comprising at least one of a first position adjuster capable of adjusting a position of the iris imager and a second position adjuster capable of adjusting a position of the reflector.

4. The authentication system according to claim 2, further comprising a rotation limiter that limits a rotation of the reflector by contacting the reflector when the reflector rotates by an allowable upper limit angle from a reference position, wherein the at least one processor is configured to execute the instructions to control the rotation driver so that the reflector rotates until the reflector contacts the rotation limiter, and (ii) calibrate the rotation driver based on a difference between: an actual command signal used for controlling the rotation driver so that the reflector rotates until the reflector contacts the rotation limiter; and an ideal command signal for controlling the rotation driver so that the reflector rotates by the allowable upper limit angle.

5. The authentication system according to claim 2, wherein the at least one processor is configured to execute the instructions to control a deceleration of the reflector when the rotating reflector stops, based on a state of the iris captured in the iris image.

6. The authentication system according to claim 2, wherein
the iris imager generates a plurality of the iris images by capturing an image of the eyes a plurality of times respectively after the rotation driver stops the rotating reflector, and
the at least one processor is configured to execute the instructions to select within the plurality of the iris images, at least one iris image where the iris is captured in a desired position, and authenticates the target using the at least one selected iris image selected.

7. The authentication system according to claim 2 further comprising:
a first reflector that is the reflector;
a second reflector that reflects light from the iris positioned at a first position toward the first reflector; and
a third reflector that reflects light from the iris positioned at a second position different from the first position toward the first reflector, wherein
the at least one processor is configured to execute the instructions to, (i) control the second reflector so that when the specified position of the eyes satisfies a predetermined first position condition, the first reflector reflects the light from the second reflector toward the iris imager, and (ii) control the third reflector so that when the specified position of the eyes satisfies a predetermined second position condition, the first reflector reflects the light from the third reflector toward the iris imager.

8. The authentication system according to claim 7, wherein
the second reflector reflects the light from the iris positioned at the first position toward the first reflector via a fourth reflector, and
the third reflector reflects the light from the iris positioned at the second position toward the first reflector via the fourth reflector.

9. The authentication system according to claim 7, wherein
the second position is different from the first position with respect to at least one of a vertical direction and a horizontal direction.

10. The authentication system according to claim 2, wherein
the iris imager is a first iris imager capable of capturing an image of the iris positioned at a first position,
the reflector is a first reflector capable of reflecting light from the iris positioned at the first position toward the first iris imager, and
the authentication system further comprises:
a second iris imager capable of generating the iris image by capturing an image of the iris positioned at a second position different from the first position; and
a second reflector capable of reflecting light from the iris positioned at the second position toward the second iris imager,
wherein the at least one processor is configured to execute the instructions to (i) specify a position of the target based on the face image, (ii) control the first reflector when the target is positioned at the first position so that the light from the iris of the target positioned at the first position is reflected toward the first iris imager, and (iii) control the second reflector when the target is positioned at the second position so that the light from the iris of the target positioned at the second position is reflected toward the second iris imager.

11. The authentication system according to claim 2, wherein
the iris imager captures an image of the iris illuminated with illumination light of a first wavelength band, and
a protective film is formed on the reflective surface, the protective film allowing light of the first wavelength band to go therethrough, attenuating light of a second wavelength band different from the first wavelength band, and capable of protecting the reflective surface.

12. The authentication system according to claim 2, wherein
the at least one processor is configured to execute the instructions to control the rotation driver so that the reflector functions as a heat releasing fan by rotating continuously in a same rotational direction.

13. The authentication system according to claim 1, wherein the at least one processor is configured to execute the instructions to authenticate the target using the iris image,
the imager is disposed on a passage which the target is going through, in a first period when the imager captures an image of the target, and
the imager retracts from the passage in a second period following after the target is authenticated.

14. The authentication system according to claim 1, further comprising:
a supporter that supports the imager; and
a housing that houses the imager supported by the supporter therein,
wherein a part of the supporter is exposed to an outside of the housing.

15. An imaging apparatus comprising:
an imager that is capable of generating an iris image by capturing an image of an iris of an target; and
a display that is capable of displaying information related to authentication of the target using the iris image, wherein
the imager includes an image sensor,
the display includes a display surface on which the information is displayed,
the display surface overlaps with the image sensor as viewed from a direction orthogonal to the display surface, the image sensor is disposed behind the display, and
the imager is oriented in a direction different from a direction in which the target is present.

* * * * *